US008193328B2

(12) United States Patent
Lu et al.

(10) Patent No.: US 8,193,328 B2
(45) Date of Patent: Jun. 5, 2012

(54) IDENTIFICATION OF MODULATORS OF SERINE PROTEASE INHIBITOR KAZAL AND THEIR USE AS ANTI-CANCER AND ANTI-VIRAL AGENTS

(75) Inventors: Xuanyong Lu, Horsham, PA (US); Timothy Block, Doylestown, PA (US)

(73) Assignee: Philadelphia Health & Education Corporation, Philadelphia, PA (US)

( * ) Notice: Subject to any disclaimer, the term of this patent is extended or adjusted under 35 U.S.C. 154(b) by 593 days.

(21) Appl. No.: 12/065,840

(22) PCT Filed: Sep. 7, 2006

(86) PCT No.: PCT/US2006/034748
§ 371 (c)(1),
(2), (4) Date: Mar. 5, 2008

(87) PCT Pub. No.: WO2007/030560
PCT Pub. Date: Mar. 15, 2007

(65) Prior Publication Data
US 2009/0017457 A1 Jan. 15, 2009

Related U.S. Application Data

(60) Provisional application No. 60/715,333, filed on Sep. 8, 2005.

(51) Int. Cl.
*C12N 15/15* (2006.01)
*C12N 15/11* (2006.01)
*C12N 15/113* (2010.01)
(52) U.S. Cl. ..................... 536/23.5; 536/23.4; 536/24.5
(58) Field of Classification Search ........................ None
See application file for complete search history.

(56) References Cited

U.S. PATENT DOCUMENTS

| | | | |
|---|---|---|---|
| 4,366,241 | A | 12/1982 | Tom et al. |
| 4,376,110 | A | 3/1983 | David et al. |
| 4,517,288 | A | 5/1985 | Giegel et al. |
| 4,683,202 | A | 7/1987 | Mullis |
| 4,745,051 | A | 5/1988 | Smith et al. |
| 4,837,168 | A | 6/1989 | De Jaeger et al. |
| 4,946,778 | A | 8/1990 | Ladner et al. |
| 5,093,246 | A | 3/1992 | Cech et al. |
| 5,530,101 | A | 6/1996 | Queen et al. |
| 5,583,973 | A | 12/1996 | De Lisi |
| 5,612,894 | A | 3/1997 | Wertz |
| 6,974,667 | B2 * | 12/2005 | Horne et al. ............... 435/6 |
| 2002/0142981 | A1 * | 10/2002 | Horne et al. ............... 514/44 |
| 2003/0228570 | A1 * | 12/2003 | Yat Wah Tom et al. ......... 435/5 |

FOREIGN PATENT DOCUMENTS

| | | |
|---|---|---|
| WO | WO 90/07861 A1 | 7/1990 |
| WO | WO 91/10741 A1 | 7/1991 |
| WO | WO 91/17271 A1 | 11/1991 |
| WO | WO 91/18980 A1 | 12/1991 |
| WO | WO 92/01047 A1 | 1/1992 |
| WO | WO 93/06121 A1 | 4/1993 |
| WO | WO 93/12227 A1 | 6/1993 |
| WO | WO 94/08051 A1 | 4/1994 |
| WO | WO 95/12608 A1 | 5/1995 |
| WO | WO 95/30642 A1 | 11/1995 |
| WO | WO 95/35503 A1 | 12/1995 |

OTHER PUBLICATIONS

Lamontagne et al., 2010, "Hepatitis B and hepatitis C virus replication upregulates serine protease inhibitor kazal, resulting in cellular resistance to serine protease-dependent apoptosis", Journal of Virology, vol. 84, No. 2, pp. 907-917.*
Dimasi, N., et al., 1997, "Characterization of engineered hepatitis C virus NS3 protease inhibitors affinity selected from human pancreatic secretory trypsin inhibitor and minibody repertoires", Journal of Virology, vol. 71, No. 10, pp. 7461-7469.*
Sacco, R., et al., 2003, "Antiapoptotic regulation by hepatitis C virus core protein through up-regulation of caspase-activated DNase", Virology, vol. 317, No. 1, pp. 34-35.*
Guo, J.-T., et al., 2004, "Mechanism of the interferon alpha response against hepatitis C virus replicons", Virology, vol. 325, No. 1, pp. 71-81.*
Kamegaya, Y., et al., 2005, "Hepatitis C virus acts as a tumor accelerator by blocking apoptosis in a mouse model of hepatocarcinogenesis", Hepatology, vol. 41, No. 3, pp. 660-667.*
Adrain, C. et al., "Molecular ordering of the caspase activation cascade initiated by the cytotoxic T lymphocyte/natural killer (CTL/NK) protease granzyme B," J Biol Chem 280, 4663-4673 (Feb. 11, 2005).
Ashkenazi, A. et al, "Death receptors: signaling and modulation," Science 281, 1305-1308 (Aug. 28, 1998). Barany, "Genetic disease detection and DNA amplification using cloned thermostable ligase," Proc. Natl. Acad. Sci. USA, 88:189-93 (1991).
Barry, M. et al., "Granzyme B short-circuits the need for caspase 8 activity during granule-mediated cytotoxic T-lymphocyte killing by directly cleaving Bid," Mol Cell Biol 20, 3781-3794 (Jun. 2000).
Beauregard et al., "Proteolytic activation of receptor-bound anthrax protective antigen on macrophages promotes its internalization," Cell. Microbiol. 2: 251-58, 2000.
Bevan et al., "Identifying small-molecule lead compounds: the screening approach to drug discovery," Trends in Biotechnology 13:115-122, 1995.
Brown, J.M. et al., "The role of apoptosis in cancer development and treatment response," Nat Rev Cancer 5, 231-237 (Mar. 2005).
Budihardjo, I. et al., "Biochemical pathways of caspase activation during apoptosis," Annu Rev Cell Dev Biol 15, 269-290 (1999).
Buroker-Kilgore et al., "A Coomassie brilliant blue G-250-based colorimetric assay for measuring activity of calpain and other proteases," Anal. Biochem. 208: 387-92, 1993.

(Continued)

Primary Examiner — Manjunath Rao
Assistant Examiner — William W Moore
(74) Attorney, Agent, or Firm — Woodcock Washburn, LLP

(57) ABSTRACT

This invention describes a relevant etiology of cancer and a novel anti-cancer therapeutic strategy, based on the discovery that a protein named serine protease inhibitor (SPIK/SPINK/PSTI) was up-regulated by hepatitis B and C virus infections consequently suppressing the cell apoptosis. Accordingly, this invention provides an inhibitor of SPIK and/or a technology of suppression of over-expression of SPIK in cells. The inhibitors include: 1) chemical compounds, which can inhibit SPIK transcripts, protein activity, and gene expression, 2) SPIK siRNA (RNAi gene silence or dsRNA of SPIK, 3) DNA anti-sense and anti-SPIK antibody. Further, this invention provides a method of using the inhibitor as an anti-cancer agent to re-instate cancer cell apoptosis (e.g., serine protease dependent cell apoptosis).

2 Claims, 9 Drawing Sheets

OTHER PUBLICATIONS

Butler, J.E., "The Amplified ELISA: Principles of and Applications for the Comparative Quantification of Class and Subclass Antibodies and the Distribution of Antibodies and Antigens in Biochemical Separates," Meth. Enzymol., 73:482-523 (1981).

Cheung et al., "Epitope-specific antibody response to the surface antigen of duck hepatitis B virus in infected ducks," Virology 176:546-552 (1990).

Coolican et al., "The role of subunit autolysis in activation of smooth muscle Ca2+-dependent proteases," J Biol. Chem. 261: 4170-6, 1986.

Cory, S. et al, "The Bcl2 family: regulators of the cellular life-or-death switch," Nat Rev Cancer 2, 647-656 (Sep. 2002).

Current Protocols in Molecular Biology, John Wiley & Sons, N.Y. (1989), 6.3.1-6.3.6.

de Bruin, E.C. et al., "A serine protease is involved in the initiation of DNA damage-induced apoptosis," Cell Death Differ 10, 1204-1212 (Oct. 2003).

Deveraux, Q.L. et al., "Cleavage of human inhibitor of apoptosis protein XIAP results in fragments with distinct specificities for caspases," Embo J, 18, 5242 (Oct. 1, 1999).

Deveraux, Q.L. et al., "IAP family proteins—suppressors of apoptosis," Genes Dev 13, 239 (Feb. 1, 1999).

Deveraux, Q.L. et at, "IAPs block apoptotic events induced by caspase-8 and cytochrome c by direct inhibition of distinct caspases," Embo J, 17, 2215 (Apr. 15, 1998).

Drenth, J.P. et al., "Granzyme A induces caspase-independent mitochondrial damage, a required first step for apoptosis," Gut 50, 687-692 (May 2002).

Ecker et al., "Combinatorial Drug Discovery: Which Methods Will Produce the Greatest Value?" Bio/Technology 13:351-360, 1995.

Egger, L. et al., "Serine proteases mediate apoptosis-like cell death and phagocytosis under caspase-inhibiting conditions," Cell Death Differ 10, 1188-1203 (Oct. 2003).

Endo, T. et al., "Expression of IAP family proteins in colon cancers from patients with different age groups," Cancer Immunol Immunother 53, 770-776 (Sep. 2004).

Fernandes "Technological advances in high-throughput screening," (1998) Curr Opin Chem Biol 2:597-603.

Fire, A., "RNA-triggered gene silencing," Trends Genet 15, 358 (Sep. 1999).

Golstein, P., "Controlling cell death," Science 275, 1081-1082 (Feb. 21, 1997).

Goping, I.S. et al., "Granzyme B-induced apoptosis requires both direct caspase activation and relief of caspase inhibition," Immunity 18, 355 (Mar. 2003).

Green, D.R. et al., "The pathophysiology of mitochondrial cell death," Science 305, 626-629 (2004).

Greene, L.J. et al., "Human pancreatic secretory trypsin inhibitor," Methods Enzymol 45, 813-825 (1976).

Gu, B. et al., "Mapping cooperative activity of the hepatitis C virus RNA-dependent RNA polymerase using genotype 1a-1b chimeras," Biochemical and Biophysical Research Communications 313, 82, 343 (2004).

Guatelli, et al., "Isothermal, in vitro amplification of nucleic acids by a multienzyme reaction modeled after retroviral replication," Proc. Natl Acad. Sci. USA, 87:1874-78 (1990).

Guicciardi, M.E. et al., "Apoptosis: a mechanism of acute and chronic liver injury," Gut 54, 1024-1033 (Jul. 2005).

Guo, J-T. et al., "Effect of alpha interferon on the hepatitis C virus replicon," J. Virol. 75, 8516 (Sep. 15, 2001).

Higashiyama, M. et al., "Expression of pancreatic secretory trypsin inhibitor (PSTI) in colorectal cancer," Br J Cancer 62, 954-958 (Dec. 1990).

Higashiyama, M. et al., "Immunohistochemical study on pancreatic secretory trypsin inhibitor (PSTI) in gastric carcinomas," Am J Clin Pathol 93, 8-13 (Jan. 1990).

Hodgson, "Receptor Screening and the Search for New Pharmaceuticals," Bio/Technology 10:973-980, 1992.

Houghten et al., "Generation and use of synthetic peptide combinatorial libraries for basic research and drug discovery," Nature 354:84-86, 1991.

Igney, F.H. et al., "Death and anti-death: tumour resistance to apoptosis," Nature Reviews Cancer 2, 277-288 (2002).

Kamegaya, Y. et al., "Hepatitis C virus acts as a tumor accelerator by blocking apoptosis in a mouse model of hepatocarcinogenesis," Hepatology 41, 660-667 (Mar. 2005).

Kim et al., "Production and proteolytic assay of lethal factor from *Bacillus anthracis*," Protein Expr Purif., 30(2):293-300, 2003.

Kirkland, T.N. et al., "Analysis of the fine specificity and cross-reactivity of monoclonal anti-lipid A antibodies," J. Immunol. 137:3614-3619 (1986).

Kobayashi, K. et al., "Pancreatic secretory trypsin inhibitor as a diagnostic marker for adult-onset type II citrullinemia," Hepatology 25, 1160-1165 (May. 1997).

Kwoh, et al., "Transcription-based amplification system and detection of amplified human immunodeficiency virus type 1 with a bead-based sandwich hybridization format," Proc. Natl. Acad. Sci. USA, 86:1173-77 (1989).

LaCasse, E.C. et al., "The inhibitors of apoptosis (IAPs) and their emerging role in cancer," Oncogene 17, 3247 (Dec. 24, 1998).

Lam, K.S. et al., "A new type of synthetic peptide library for identifying ligand-binding activity," Nature 354:82-84, 1991.

Liston, P. et al., "The inhibitors of apoptosis: there is more to life than Bcl2," Oncogene 22, 8568 (Nov. 24, 2003).

Lonergan et al., "Improved Calpain Assay Using Fluorescein Isothiocyanate-Labeled Casein," J Food Sci. 60:72-3, 78, 1995.

Lord, S.J. et al., "Granzyme B: a natural born killer," Immunol Rev 193, 31 (Jun. 2003).

Lu, X. and Block, T., "Study of the early steps of the Hepatitis B Virus life cycle," Int J Med Sci 1, 21-33 (2004).

Marasco, et al., "Design, intracellular expression, and activity of a human anti-human immunodeficiency virus type 1 gp120 single-chain antibody," Proc. Natl. Acad. Sci. USA, 90:7889-93 (1993).

Martinon, F., "Inflammatory caspases: linking an intracellular innate immune system to autoinflammatory diseases," Cell 117, 561-574 (2004).

Martinvalet, D. et al, "Granzyme A induces caspase-independent mitochondrial damage, a required first step for apoptosis," Immunity 22, 355-370 (Mar. 2005).

Moldenhauer et al., "Identity of HML-1 antigen on intestinal intraepithelial T cells and of B-ly7 antigen on hairy cell leukaemia," Scand. J. Immunol. 32:77-82 (1990).

Morel et al., "Monoclonal antibodies to bovine serum albumin: affinity and specificity determinations," Mol. Immmnol. 25(1):7-15 (1988).

Mullbacher, A. et al., "Granzyme A is critical for recovery of mice from infection with the natural cytopathic viral pathogen, ectromelia," PNAS 93, 5783-5787 (Jun. 11, 1996).

Murata, A. et al., Release of pancreatic secretory trypsin inhibitor from human hepatoblastoma cells on stimulation with cytokines, Life Sci 43, 1233-1240 (1988).

Nemoto, T. et al., "Expression of IAP family proteins in esophageal cancer," Exp Mol Pathol 76, 253-259 (Jun. 2004).

Ng et al., "A fluorescent oligopeptide energy transfer assay with broad applications for neutral proteases," Anal. Biochem. 183: 50-6, 1989.

Nicholson, D.W. et al, "Caspases: killer proteases," Trends Biochem Sci 22, 299-306 (Aug. 1997).

Notarbartolo, M. et al., "Expression of IAPs and alternative splice variants in hepatocellular carcinoma tissues and cells," Ann NY Acad Sci 1028, 289-293 (Dec. 2004).

Nunez, G. et al., "Caspases: the proteases of the apoptotic pathway," Oncogene 17, 3237-3245 (Dec. 24, 1998).

Ohmachi, Y. et al., "Expression of the pancreatic secretory trypsin inhibitor gene in the liver infected with hepatitis B virus," J Hepatol 21, 1012-1016 (Dec. 1994).

Ohmachi, Y. et al., "Specific expression of the pancreatic-secretory-trypsin-inhibitor (PSTI) gene in hepatocellular carcinoma," Int J Cancer 55, 728-734 (Nov. 11, 1993).

Pardo, J. et al., "Apoptotic pathways are selectively activated by granzyme A and/or granzyme B in CTL-mediated target cell lysis," J Cell Biol 167, 457-468 (Nov. 8, 2004).

Pardo, J. et al., "Granzymes are essential for natural killer cell-mediated and perf-facilitated tumor control," Eur J Immunol 32, 2881-2887 (Oct. 2002).

Pereira, R.A. et al, "Granzyme A, a noncytolytic component of CD8(+) cell granules, restricts the spread of herpes simplex virus in the peripheral nervous systems of experimentally infected mice," J Virol 74, 1029-1032 (Jan. 2000).

Preusser, M. et al., "Survivin expression in intracranial ependymomas and its correlation with tumor cell proliferation and patient outcome," Am J Clin Pathol 124, 543-549 (Oct. 2005).

Queen et al., "A humanized antibody that binds to the interleukin 2 receptor," Proc. Natl. Acad. Sci. USA 86, 10029-10033 (1989).

Rocken, C. et al., "Pathology and pathogenesis of hepatocellular carcinoma," Dig Dis 19, 269 (2001).

Salier, J.P., "Inter-alpha-trypsin inhibitor: emergence of a family within the Kunitz-type protease inhibitor superfamily," Trends Biochem Sci 15, 435 (Nov. 1990).

Schultz "High throughput purification of combinatorial libraries," (1998) Bioorg Med Chem Lett 8:2409-2414.

Shresta, S. et al., "Granzyme A initiates an alternative pathway for granule-mediated apoptosis," T. A. Graubert, D. A. Thomas, S. Z. Raptis, T. J. Ley, Immunity 10, 595 (May 1999).

Sittampalam "High-throughput screening: advances in assay technologies," (1997) Curr Opin Chem Biol 1:384-91.

Songyang, et al., "SH2 domains recognize specific phosphopeptide sequences," Cell, 72:767-78 (1993).

Stahli et al., "Distinction of epitopes by monoclonal antibodies," Methods in Enzymology 9:242-253 (1983).

Tamm, I. et al., Clin Cancer Res 6, 1796 (May 2000).

Tanaka, K. et al., "Expression of survivin and its relationship to loss of apoptosis in breast carcinomas," Clin Cancer Res 6, 127 (Jan. 2000).

Thorburn, J. et al., "Caspase- and serine protease-dependent apoptosis by the death domain of FADD in normal epithelial cells," Mol. Biol. Cell 14, 67-77, (Jan. 1, 2003).

Tomita, N. et al., "Expression of pancreatic secretory trypsin inhibitor gene in human colorectal tumor," Cancer 66, 2144-2149 (Nov. 15, 1990).

Tomlinson, I.P. et al., "The mutation rate and cancer," Proc Natl Acad Sci USA 93,14800 (Dec. 10, 1996).

Tong, Q.S. et al., "Downregulation of XIAP expression induces apoptosis and enhances chemotherapeutic sensitivity in human gastric cancer cells," Cancer Gene Ther 12, 509 (May 2005).

Tong, Q.S. et al., "Selection of optimal antisense accessible sites of survivin and its application in treatment of gastric cancer," World J Gastroenterol 11, 634-640 (Feb. 7, 2005).

Tsuzuki, S. et al., "Purification and identification of a binding protein for pancreatic secretory trypsin inhibitor: a novel role of the inhibitor as an anti-granzyme A," Biochem J 372, 227-233 (May 15, 2003).

Twining, "Fluorescein isothiocyanate-labeled casein assay for proteolytic enzymes," Anal. Biochem. 143: 30-4, 1984.

Van Holde, K. E., "X-Ray Diffraction", Physical Biochemistry, (Prentice-Hall, New Jersey 1971), pp. 221-239.

Voller, A., "The Enzyme Linked Immunosorbent Assay (ELISA)", La Ricerca Clin Lab, 1978, 8, 289-298.

Voller, et al., "Enzyme immunoassays with special reference to ELISA techniques," J. Clin. Pathol., 31:507-20 (1978).

Wadstroem and Smyth, "Zymogram Methods Applied to Thin-Layer Isoelectric Focusing in Polyacrylamide Gel," Sci. Tools 20: 17-21, 1973.

Weller "High throughput analysis and purification in support of automated parallel synthesis," (1997) Mol Divers. 3:61-70.

Yasuda, T. et al., "Identification of the IL-6-responsive element in an acute-phase-responsive human pancreatic secretory trypsin inhibitor-encoding gene," Gene 131, 275-280 (Sep. 15, 1993).

* cited by examiner

S2-3, S2-4: stable cell line expressing SPIK by integrated SPIK gene.
Huh7T : The parental cell of S2-3.

1. Huh7T transfected with HBV DNA
2. Huh7T transfected with Vector

1. G54 cells containing HCV replicon.
2. Parental cell of G54.
3. 913 cells containing HCV replicon (Dr. Guo).
4. Parental cell of 913.

1 & 2: None
3 & 4: 888 (HCV polymerase inhibitor).
5 & 6: INF-a

A. pSilencer™ 1.0-U6 siRNA Expression Vector

Sense      Loop        Antisense
5'-N(19)  TTCAAGAGA   N(19)    TTTTT-3' (53 bases)
3'-CCGG N(19) AAGTTCTCT N(19)  AAAAAATTAA-5' (61 bases)
Apa I                                   EcoR I B. Sequence and inserts of siRNA C. SPIK siRNA D. Selecting the SPIK siRNA

SEQUENCE LISTING

<160> NUMBER OF SEQ ID NOS: 8

<210> SEQ ID NO 1
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 1

```
caggcatctt tcttctcag                                                  19
```

<210> SEQ ID NO 2
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 2

```
gatatatgac cctgtctgt                                                  19
```

<210> SEQ ID NO 3
<211> LENGTH: 340
<212> TYPE: DNA
<213> ORGANISM: Artificial Sequence
<220> FEATURE:
<223> OTHER INFORMATION: SPIK DNA

<400> SEQUENCE: 3

```
gaagagacgt ggtaagtgcg gtgcagtttt caactgacct ctggacgcag aacttcagcc     60
atgaaggtaa caggcatctt tcttctcagt gccttggccc tgttgagtct atctggtaac    120
actggagctg actccctggg aagagaggcc aaatgttaca atgaacttaa tggatgcacc    180
aagatatatg accctgtctg tgggactgat ggaaatactt atcccaatga atgcgtgtta    240
tgttttgaaa atcggaaacg ccagacttct atcctcattc aaaaatctgg gccttgctga    300
gaaccaaggt tttgaaatcc catcaggtca ccgcgaggcc                          340
```

<210> SEQ ID NO 4
<211> LENGTH: 79
<212> TYPE: PRT
<213> ORGANISM: Artificial Sequence
<220> FEATURE:
<223> OTHER INFORMATION: SPIK protein

<400> SEQUENCE: 4

```
Met Lys Val Thr Gly Ile Phe Leu Leu Ser Ala Leu Ala Leu Leu Ser
1               5                   10                  15

Leu Ser Gly Asn Thr Gly Ala Asp Ser Leu Gly Arg Glu Ala Lys Cys
            20                  25                  30

Tyr Asn Glu Leu Asn Gly Cys Thr Lys Ile Tyr Asp Pro Val Cys Gly
        35                  40                  45

Thr Asp Gly Asn Thr Tyr Pro Asn Glu Cys Val Leu Cys Phe Glu Asn
    50                  55                  60

Arg Lys Arg Gln Thr Ser Ile Leu Ile Gln Lys Ser Gly Pro Cys
65                  70                  75
```

<210> SEQ ID NO 5
<211> LENGTH: 9
<212> TYPE: DNA
<213> ORGANISM: Artificial Sequence
<220> FEATURE:
<223> OTHER INFORMATION: Oligonucleotide primer

<400> SEQUENCE: 5

```
ttcaagaga                                                              9
```

<210> SEQ ID NO 6
<211> LENGTH: 9
<212> TYPE: DNA
<213> ORGANISM: Artificial Sequence
<220> FEATURE:
<223> OTHER INFORMATION: Oligonucleotide primer

```
<400> SEQUENCE: 6 aagttctct                                                                9

<210> SEQ ID NO 7
<211> LENGTH: 6
<212> TYPE: DNA
<213> ORGANISM: Artificial Sequence
<220> FEATURE:
<223> OTHER INFORMATION: Oligonucleotide primer

<400> SEQUENCE: 7 tttttt                                                                   6

<210> SEQ ID NO 8
<211> LENGTH: 10
<212> TYPE: DNA
<213> ORGANISM: Artificial Sequence
<220> FEATURE:
<223> OTHER INFORMATION: Oligonucleotide primer

<400> SEQUENCE: 8
aaaaaattaa                                                              10
```

IDENTIFICATION OF MODULATORS OF SERINE PROTEASE INHIBITOR KAZAL AND THEIR USE AS ANTI-CANCER AND ANTI-VIRAL AGENTS

CROSS-REFERENCE TO RELATED APPLICATIONS

This application is the National Stage of International Application No. PCT/US2006/034748, filed Sep. 7, 2006, which claims the benefit of U.S. Provisional Application No. 60/715,333, filed Sep. 8, 2005, the disclosures of which are incorporated herein by reference in their entireties.

BACKGROUND OF THE INVENTION

1. Field of Invention

This invention relates to serine protease inhibitor Kazal (SPIK/SPINK/PSTI) and more specifically, its inhibitors and the use of inhibitors of SPIK as anti-cancer agents and anti-viral agents such as hepatitis B and C virus (HBV and HCV).

2. Description of Related Art

Serine protease inhibitor Kazal (SPIK) is a small protein derived from a gene with 240 base pairs that has been shown to broadly regulate the activity of many cellular proteases, such as the trypsin like proteases and chymotrypsin like proteases (1). SPIK was first discovered in the pancreas behaving as an inhibitor to prevent autoactivation of trypsinogen (2). The expression of SPIK in human liver and in other organs generally is very low. It suggests that the SPIK gene is usually inactivated in these cells. However, the expression of SPIK has been shown to increase under conditions of inflammation and cell carcinogenesis, for example, in hepatitis and the hepatocellular carcinoma (HCC) (3-7).

The reason for the over-expression of SPIK in inflammation and cancer cells is unclear. SPIK is related to cell innate defense response to virus infection. During infection such as HBV and HCV, the viral proteins induce the cell immune-response resulting in release of cytokines such as interleukin 6 (IL6), TNF-α and interferon to trigger inflammation and cell apoptotic death. Because there is an IL6 responsive element existing in the SPIK gene regulation region, the over-expression of SPIK is triggered by cytokines released during the immune response or inflammation (8, 9). SPIK is a secreted protein, which implies that at least part of the function of SPIK might be working as an anti-inflammatory protein. The anti-inflammatory nature of SPIK is supported by the fact that altering the function of SPIK by mutation triggers chronic pancreatitis (10). More importantly, our studies find that the over-expression of SPIK results in resistance to apoptotic cell death. By enhancing SPIK expression, the cells infected by virus will escape the apoptotic death triggered by immune surveillance, such as CTL-induced cell apoptosis. The fact that SPIK can bind Granzyme A, a CTL cell and NK cell released serine protease, which induces serine protease dependent cell apoptosis (SPDCA), suggests this hypothesis is relevant (11-13). As a serine protease inhibitor, SPIK can only prevent serine protease dependent cell apoptosis or SPDCA, not caspase dependent cell apoptosis or CDCA (our observation). Although CDCA is important in the clearance of virus infection, however, SPDCA might play a more important role than CDCA in the clearance of chronic virus infection (14-16), this finding is particularly significant to the ineffective clearance of infected cells during chronic viral infection. Our studies show that in HBV infected cells only SPIK, not other apoptosis inhibitors such as the CDCA inhibitors survivin and XIAP, is dramatically increased.

Since escape from immune surveillance-mediated apoptosis is a condition of cancer progression, it is understandable that active expression of SPIK results in carcinogenesis, for example, in chronic HCV and HBV infection associates closely with liver cancer. The current invention recognizes that suppressing SPIK expression will induce the apoptosis of cancer cells.

Despite the foregoing developments, there is a need in the art for inhibitors of SPIK to be used as anti-cancer agents and anti-viral agents for hepatitis B and C.

All references cited herein are incorporated herein by reference in their entireties.

BRIEF SUMMARY OF THE INVENTION

This invention elucidates a mechanism of cancer development and describes a novel anti-cancer therapeutic strategy, based on the discovery that a protein named serine protease inhibitor (SPIK/SPINK/PTSI) is up-regulated in hepatitis B and C virus infected cells, consequently suppressing the cell apoptosis.

Over-expression of SPIK has been demonstrated in many cancer cells. Our studies suggest that this results in the resistance of these cells to apoptotic death, for example, the apoptosis triggered by immune-surveillance. Therefore, suppressing SPIK expression could induce the apoptosis of cancer cells. For this purpose, any anti-SPIK technologies and compounds will be used as the anti-cancer agents, particularly to Hepatocellular carcinoma.

Current anti-cancer therapies including radio and chemotherapy are mainly based on attacking or killing cancer cells by external agents. Discovery that SPIK was up-regulated in tumor cells suggests that it is possible to find a physiological way (i.e., cell apoptotic death) to kill cancer cells by regulation of cellular protein. It would be more effective, specific and less toxic.

Additionally, it was found recently that the serine protease inhibitor is increased in cancerous cells that are resistant to radio and chemotherapy such as lung cancer. Therefore, the anti-cancer agents developed by this strategy also can be combined with radio and chemotherapies as a powerful tool in cancer treatment.

The invention provides a method for identifying a Serine Protease Inhibitor-Kazal (SPIK) modulatory compound, wherein the modulatory compound modulates SPIK serine protease inhibitory activity, the method comprising: (a) contacting a serine protease with SPIK protein in the presence of a labeled serine protease substrate and measuring a first amount of serine protease activity; (b) contacting a serine protease with SPIK protein in the presence of a labeled serine protease substrate and a test agent and measuring a second amount of serine protease activity; (c) comparing the first amount and second amounts of serine protease activity to identify a compound which modulates SPIK serine protease inhibitory activity, wherein the test agent is selected from the group consisting of small molecules, proteins, nucleic acids, and antibodies. The invention provides a method wherein the label is fluorescent. The invention provides a method wherein the label can be detected by FRET. The invention provides a method wherein the modulation is selected from the group consisting of inhibition and activation. The invention provides a method wherein a plurality of test agents are screened simultaneously. The invention provides a method wherein the SPIK polypeptide consists essentially of a polypeptide encoded by a sequence of nucleotides selected from the group consisting of a sequence of nucleotides that: (a) is set forth in SEQ ID NO. 3; (b) hybridizes under conditions of high stringency to a nucleic acid of SEQ ID NO: 3; (c) hybridizes under conditions of high stringency to a nucleic acid complementary to the nucleic acid of SEQ ID NO: 3; (d) encodes a biologically active variant of the polypeptide of SEQ ID NO: 4; and (e) comprises degenerate codons of the sequences of nucleotides of (a), (b), (c) or (d).

The invention provides a compound which modulates SPIK serine protease inhibitory activity identified by the method above. The invention provides a kit comprising the compound for use in treating a disease selected from the group consisting of HBV infection, HCV infection, hepatitis, cancer, and hepatic cancer, in an animal and a [pharmaceutically acceptable carrier.

The invention provides an siRNA which is a member selected from the group consisting of L71 siRNA comprising sense and anti-sense oligonucleoside with the SPIK sequence of SEQ ID NO: 1, as shown in FIG. 9, and L183 comprising sense and anti-sense oligonucleoside with the SPIK sequence SEQ ID NO: 2, as shown in FIG. 9.

The invention provides a diagnostic kit comprising at least one specific SPIK gene nucleic acid or anti-SPIK antibody reagent to diagnose patients exhibiting disease symptoms or at risk for developing a disease, wherein the disease is a member selected from the group consisting of HBV infection, HCV infection, hepatitis, cancer, and hepatic cancer.

The invention provides an inhibitor of SPIK expression or function used for treatment of a disease which is a member selected from the group consisting of HBV infection, HCV infection, hepatitis, cancer, and hepatic cancer.

The invention provides for the use of a compound identified by the method above for preparing a medicament for enhancing a therapeutic effect of a drug in treating a disease selected from the group consisting of HBV infection, HCV infection, hepatitis, cancer, and hepatic cancer, in an animal.

The invention provides a method of identifying therapeutically effective compounds comprising determining the ability of test agents to modulate SPIK serine protease inhibitory activity in apoptosis sensitive cells expressing SPIK exposed to apoptotic agents, wherein the test agent is a compound determined to have potential therapeutic efficacy if the apoptosis of the cells in response to the agents changes compared to control cells not exposed to the test agent. The invention provides a method wherein the cells are selected from the group consisting of hepatic cells, cancer cells, and hepatic cancer cells.

The invention provides a method for identifying a compound which is an inhibitor of SPIK expression comprising: (a) contacting a test agent in vitro with a cell that expresses SPIK protein; (b) determining the expression level of the SPIK protein in the cell; and (c) determining whether the expression level determined in step (b) is lower than the SPIK protein expression level determined in the absence of the test agent, such lower expression level indicating that the compound is an inhibitor of SPIK expression. The invention provides a method wherein the SPIK protein comprises the amino acid sequence as set forth in SEQ ID NO: 4. The invention provides a method wherein the cell is selected from the group consisting of a liver cell, a cancer cell, and a hepatic cancer cell.

The invention provides a method of screening for a compound that inhibits, diminishes, or modulates anti-apoptotic activity in an eukaryotic cell, said method comprising: (a) introducing into eukaryotic cells an expression vector comprising a polynucleotide encoding a SPIK polypeptide, or fragment thereof, having serine protease inhibitory activity, (b) treating one fraction of said cells with a test agent and leaving a second fraction of said cells untreated as a control, (c) treating both fractions of cells with an agent that induces cell death, and (d) detecting an inhibition, diminution or modulation in anti-apoptotic activity in the fraction of cells treated with the test agent in comparison to the untreated control, thereby screening for a test agent which is a compound that inhibits, diminishes, or modulates anti-apoptotic activity in an eukaryotic cell. The invention provides a method wherein said test agent is selected from the group consisting of small molecules, proteins, nucleic acids, and antibodies. The invention provides a method wherein the SPIK polypeptide consists essentially of a polypeptide encoded by a sequence of nucleotides selected from the group consisting of a sequence of nucleotides that: (a) is set forth in SEQ ID NO. 3; (b) hybridizes under conditions of high stringency to a nucleic acid of SEQ ID NO: 3; (c) hybridizes under conditions of high stringency to a nucleic acid complementary to the nucleic acid of SEQ ID NO: 3; (d) encodes a biologically active variant of the polypeptide of SEQ ID NO: 4; and (e) comprises degenerate codons of the sequences of nucleotides of (a), (b), (c) or (d).

BRIEF DESCRIPTION OF SEVERAL VIEWS OF THE DRAWINGS

The invention will be described in conjunction with the following drawings in which like reference numerals designate like elements and wherein:

FIG. 1A—Northern blot to detect SPIK. Total RNA was isolated from $10^6$ cells seeded in 6 well plates. 10 µg RNA then was resolved in 1% denatured agarose gel, and transferred to the Nylon membrane. After hybridization with $P^{32}$ labeled probes, the bands were visualized by Phosphorimager. The equal loading of the samples was defined by Ethidium bromide (EB) stained ribosome RNAs in each experiments. The SPIK in cells transfected with P3/L158, P3 alone, and vector were shown in Line 1, 2 and 3.

FIG. 1B—the SPDCA was induced via incubation of cells with BFA/CHX/Z-VAD (5 µg/ml/10 µg/ml/100 µM) 24 hours. Apoptosis was examined at phase contrast microscope (up panel) or Hoechst staining (down panel). For Hoechst staining, cells were washed with water briefly, followed with incubation of 100 µg/ml dye at room temperature 5 minutes. After 2 times washing with water, the images were visualized under fluoresce microscope. Typical apoptotic cells and nucleus condensation shown by bright blue florescence were indicated by arrows.

FIG. 2A-Northern blot to detect SPIK. The SPIK in cells transfected with P3 alone, P3/L158 and vector were shown in Line 1, 2 and 3 (duplicate).

FIG. 2B—The SPDCA was induced via incubation of cells with BFA/CHX/Z-VAD 24 hours. The apoptosis was examined at phase contrast microscope (top panel) or Hoechst staining (bottom panel) as before (FIG. 1). Typical apoptotic cells and nucleus condensation were indicated by bright blue florescence.

FIG. 4A. The apoptosis of S2-3 induced by BFA/CHX/Z-VAD treatment. The stable cell line over-expressing SPIK (top panel) and its parental cell Huh7T (bottom panel) were treated with SPDCA inducer (BFA/CHX and Z-VAD). After 24 hours the apoptosis was examined by annexin stain (for apoptosis in early stage) and Hoechst stain after 28 hours (for apoptosis in middle stage).

FIG. 4B. Apoptosis in late stage treatment by DNA fragmentation. S2-3 and Huh7T cells were treated with SPDCA inducer as before. The chromosome DNA was isolated from cells after 24 hours and 70 hours. The ten microgram DNA was resolved in 2% agarose gel. DNA fragmentation was shown by Ethidium bromide.

FIG. 4C. Clonogenic growth study to examine cell apoptosis. S2-3 cell and its parental cell were treated with SPDCA inducer as before. After 48 hours treatment, cells were released by trypsin treatment and re-seeded in 6-well-plate. After one weeks the growth of the cells and its clones were examined. The growth clone of the cell was observed under microscope (Left). The cell viability was determined by WST analysis. The Optical density was measured in chart (Right).

FIG. 5A. S2-3 and Huh7T cells were treated with CDCA inducer 400 µM etoposide. After 40 hours, the cells apoptosis was examined in microscope and stained with annexin. The green fluorescence suggests the apoptosis.

FIG. 5B. The activation of caspase 3 (CDCA) in S2-3 cells treated with etoposide but not BFA/CHX/Z-VAD. The S2-3 cell and its parental cell Huh7T were either treated with SPDCA inducer BFA/CHX/ZVAD or CDCA inducer etoposide. The caspase activity was determined after 48 hours treatment by Caspase 3 detection kit (Biovision, Mountain View, Calif.).

FIG. 6A. SPIK RNA in the Huh7 cells transfected with plasmid containing head to head double HBV genomes was analyzed 6 days after transfection (Line 1, left panel). The Huh7 cells transfected with vector was used as a control (Line 2, left panel). The HBV RNA including pre-genomic RNA and 2.4/2.1 Kb RNAs in transfected cells were examined by hybridization of membrane with HBV specified probe (Right panel).

FIG. 6B—Huh 7 cells were co-transfected with HBV genomes and HBV siRNAs with different dose (from 1-100 ng/well) or targeting at different HBV region. After 6 days, the HBV and SPIK RNAs were analyzed by Northern blot.

FIG. 7A—HCV replicon cells from two laboratories (G54/its parental cell, and 913/its parental cell) were analyzed by Northern blot with labeled SIPK probe. The SPIK RNA was indicated.

FIG. 7B—HCV replicon cells were incubated with HCV polymerase inhibitor 888 (2 mM) 2 days (Lines 3 & 4 duplicate) and $10^5$ IU/ml interferon-a overnight (Lines 5 & 6 duplicate) or left untreated (Line 1 & 2 duplicate). The suppressions of HCV RNA and SPIK RNA then were analyzed by Northern blot as before. The smear detected by HCV probe under the band of HCV RNA probably was the replication form of HCV.

FIG. 8A—$10^5$ HepG2.215 (C & D) and HepG2 cells (A & B) were seeded in the collagen coated 6 well plates until 80% confluent. SPDCA was induced via incubation of cells with BFA/CHX/Z-VAD as before. The apoptosis was examined at phase contrast microscope and Hoechst staining. The typical apoptotic cells and nucleus condensation shown by bright blue Hoechst staining were indicated by arrows.

FIG. 8B—the percentage of apoptotic cell in HepG2.2.15 and HepG2 was calculated by the counting of the apoptotic cells stained by Hoechst. The percentage of apoptotic cell (apoptotic cell/total cell) was averaged from four visions.

FIG. 8C—the resistance of HCV expressing cells to SPDCA determined by annexin staining and Hoechst staining.

FIG. 8D—the DNA fragmentation in HCV expressing cells.

FIG. 9A—The structure of the Vector.

FIG. 9B—The sequence and inserts of siRNA: (TTCAA-GAGA (SEQ ID NO: 5)), (AAGTTCTCT (SEQ ID NO: 6)), (TTTTTT (SEQ ID NO: 7)), (AAAAAATTAA (SEQ ID NO: 8)).

FIG. 9C—the SPIK siRNA.

FIG. 9D—Selecting the SPIK siRNA. G54 cells were transfected with SPIK siRNA L71 or L183. After 3 days, total RNA was isolated from half of the cells, and the suppressions of L71 and L183 were analyzed by Northern blot. The other half of the cells were reseeded; apoptosis was induced by treatment of BFA/CHX/Z-VAD (see Example 2). Cell apoptosis was determined by DNA fragmentation.

DETAILED DESCRIPTION OF THE INVENTION

Figure 1:
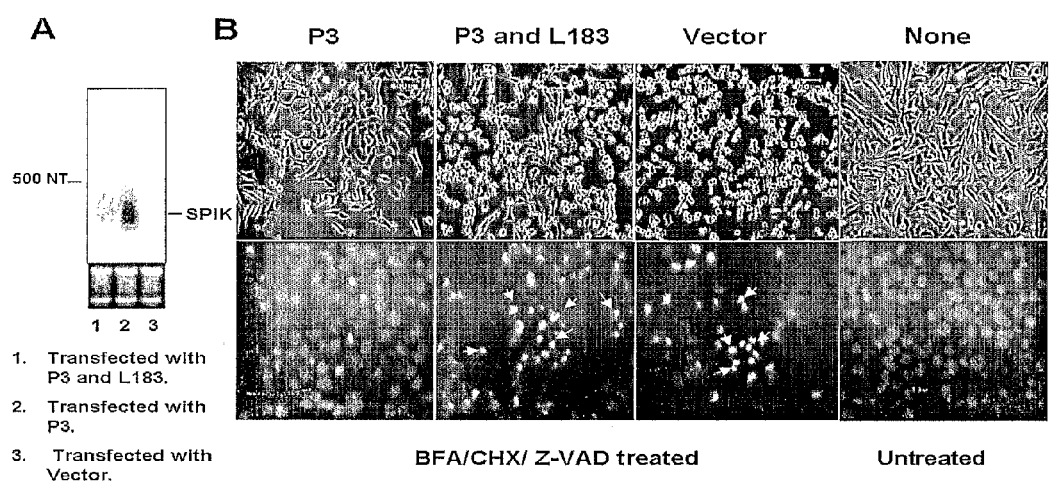
FIGS. 1A-1B. Expression of SPIK suppressing SPDCA in HeLa cells. HeLa cells were seeded in 6 well plates at a density of $1 \times 10^5$ until 80% confluency was reached. Cells were transfected with 2 µg P3 containing the entire SPIK gene under the control of HCMV promoter or vector. For silencing analysis, 1 µg siRNA L183 with U6 promoter was co-transfected with P3. After 3 days, cells were split into two daughter plates by trypsin digestion, and then cultured another 3 days for Northern Blot or SPDCA analysis respectively.

This invention describes a relevant etiology of cancer and a novel anti-cancer therapeutic strategy, based on the discovery that a protein named serine protease inhibitor (SPIK/SPINK/PSTI) was up-regulated by hepatitis B and C virus infections consequently suppressing the cell apoptosis. This is a first report to confirm that serine protease inhibitor (SPIK) is able to suppress caspase independent cell apoptosis. Moreover, the up-regulation of SPIK has been seen in the Hepatitis B virus (HBV) and Hepatitis C virus (HCV) expressing cells. As a result, these cells develop a resistance to the apoptotic death. Because the chronic infection of both HBV and HCV frequently cause liver cancer and the suppression of cell apoptosis is considerably linked to cell carcinogenesis, the biological significance of our findings illustrates the possibility that two very different viruses are using the same mechanism to trigger cancer.

While Hepatitis B and Hepatitis C viruses are very different viruses, their topology and pathogenesis are remarkably similar. The chronic infections of both of these viruses eventually develop into Hepatocellular carcinoma. The mechanisms of carcinogenesis in these two viruses are still unclear. This intention shows that serine protease inhibitor Kazal (SPIK) is up-regulated in the HBV and HCV expressing cells, which consequently suppresses the serine protease dependent cell apoptosis. Because suppression of cell apoptosis results in the escape of body immune surveillance, consequently leading to the cell carcinogenesis, it is likely that the upsurge of SPIK expression leads to cancer in chronic HBV and HCV infections. Since up-regulation of SPIK has been demonstrated in many cancer cells, a novel anti-cancer therapeutic strategy has been developed. By suppressing SPIK expression, the apoptotic cell death could be induced. Based on this strategy, any anti-SPIK technology and compound could develop to an anti-cancer agent, particularly to Hepatocellular carcinoma.

To identify novel modulators of SPIK, test agents can be first screened for ability to bind to SPIK, its fragments, variants or analogs. Agents thus identified can be then further examined for activity in modulating (e.g., inhibiting) the enzymatic activity of SPIK. Alternatively, test agents can be directly subject to screening for ability to modulate proteolysis of a substrate (e.g., a bacterial toxin or a synthetic peptide substrate) by SPIK. Typically, the test agents are screened for ability to inhibit SPIK protease inhibitory activity. However, modulators that enhance the protease inhibitory activity can also be screened for with methods of the present invention. Further, once an agent has been identified to modulate (e.g., inhibit) SPIK protease inhibitory activity, it can be further tested for ability to inhibit infection of the pathogen in a subject, e.g., with an animal model.

Recent studies suggest that the life and death of cells must be balanced if tissue homeostasis is to be maintained, too much growth and too little death can lead to a severe disturbance that might, ultimately, result in cancer (17). Cells have an intrinsic mechanism of self destruction called programmed cell death or apoptosis. In multicellular organisms, many of the mechanisms that control tissue homeostasis are linked to apoptosis. Defects in the apoptosis-inducing pathways can eventually lead to expansion of a population of neoplastic cells. Resistance to apoptosis can also augment the escape of tumor cells from surveillance by the immune system (18). In the chronic HBV/HCV infection, chronic hepatitis and inflammation usually leads to escape of infected cell from the body's immune surveillance including CTL and NK cell induced cell apoptosis, which allows the build up of cells carrying mutated genes, integrated viral DNA, and unregulated proliferation within the infected liver, eventually triggering development of HCC (19). However, the resistance of the cell to apoptosis is achieved through over-expression of proteins known as apoptosis inhibitors. For example, the over expression of apoptosis inhibitors was found in pancreatic, gastric, colon, esophageal and colorectal cancers (3, 6, 20-23). The over expression of apoptosis inhibitor, for example SPIK, was also found in HBV/HCV infected cells and HCC (4, 5, 24-26). Therefore, suppressing over-expressed apoptosis inhibitor is an approach to study the etiology of cancer, and to identify novel anti-cancer mechanisms and compounds.

The invention provides an isolated nucleic acid encoding a SPIK protein. The invention provides a nucleic acid encoding biologically active fragments of a SPIK protein. The invention further provides a nucleic acid encoding biologically active fragments of a SPIK protein wherein the biological activity is inhibition of a serine protease. The invention further provides a nucleic acid encoding biologically active fragments of a SPIK protein wherein the biological activity is inhibition of the protease activity of a serine protease. The invention further provides a nucleic acid encoding the amino acid sequence of SEQ ID NO: 4. The invention further provides a nucleic acid sequence of SEQ ID NO: 1, 2, or 3.

The invention provides an amino acid sequence of a SPIK protein. The invention provides an amino acid sequence which is a biologically active fragment of a SPIK protein. The invention further provides an amino acid sequence which is a biologically active fragment of a SPIK protein, wherein the biological activity is inhibition of a serine protease. The invention further provides an amino acid sequence which is a biologically active fragment of a SPIK protein wherein the biological activity is inhibition of the protease activity of a serine protease. The invention further provides an amino acid sequence of SEQ ID NO: 4. The invention further provides a fragment of an amino acid sequence of SEQ ID NO: 4. The invention further provides a fragment of an amino acid sequence of SEQ ID NO: 4 which is biologically active. The invention further provides a fragment of an amino acid sequence of SEQ ID NO: 4 which is biologically active wherein the biological activity is inhibition of a serine protease. The invention further provides a fragment of an amino acid sequence of SEQ ID NO: 4 which is biologically active wherein the biological activity is inhibition of the protease activity of a serine protease.

The invention provides a method for identifying a compound which modulates SPIK serine protease inhibitory activity, the method comprising: (a) contacting a serine protease with SPIK protein in the presence of a labeled serine protease substrate and measuring the first amount of serine protease activity; (b) contacting a serine protease with SPIK protein in the presence of a labeled serine protease substrate and a test agent and measuring the amount of serine protease activity; (c) comparing the first amount and second amounts of serine protease activity to identify a compound which modulates SPIK serine protease inhibitory activity. The invention further provides a method wherein the compound is selected from the group consisting of chemical compounds, SPIK siNA, dsRNA, DNA anti-sense, and anti-SPIK antibodies. The invention further provides a method wherein the label is fluorescent. The invention further provides a method wherein the label can be detected by FRET. The invention further provides a method wherein the siNA is computer designed an/or from a library. The invention further provides a method wherein the modulation is selected from the group consisting of inhibition or activation. The invention further provides a method, wherein a plurality of the compounds are screened simultaneously.

The invention provides a method for identifying a compound which modulates SPIK serine protease inhibitory activity, wherein the SPIK polypeptide consists essentially of a polypeptide encoded by a sequence of nucleotides selected from the group consisting of a sequence of nucleotides that: (a) is set forth in SEQ ID NO. 4; (b) hybridizes under conditions of high stringency to a nucleic acid complementary to an mRNA transcript present in a mammalian cell that encodes SPIK encoded by (a); (c) encodes a splice variant of (a) or (b); and (d) comprises degenerate codons of the sequences of nucleotides of (a), (b) or (c).

The invention provides a method of identifying agents capable of suppressing SPIK and which have anti-carcinogenic properties.

This invention describes a relevant etiology of cancer and a novel anti-cancer therapeutic strategy, based on the discovery that a protein named serine protease inhibitor (SPIK/SPINK/PSTI) was up-regulated by hepatitis B and C virus infections consequently suppressing the cell apoptosis. This is a first report to confirm that serine protease inhibitor (SPIK) is able to suppress caspase independent cell apoptosis. Moreover, the up-regulation of SPIK has been seen in the Hepatitis B virus (HBV) and Hepatitis C virus (HCV) expressing cells. As a result, these cells develop a resistance to the apoptotic death. Because the chronic infection of both HBV and HCV frequently cause liver cancer and the suppression of cell apoptosis is considerably linked to cell carcinogenesis, the biological significance of our findings illustrates the possibility that two very different viruses are using the same mechanism to trigger cancer.

While Hepatitis B and Hepatitis C viruses are very different viruses, their topology and pathogenesis are remarkably similar. The chronic infections of both of these viruses eventually develop into Hepatocellular carcinoma. The mechanisms of carcinogenesis in these two viruses are still unclear. This intention shows that serine protease inhibitor Kazal (SPIK) is up-regulated in the HBV and HCV expressing cells, which consequently suppresses the serine protease dependent cell apoptosis. Because suppression of cell apoptosis results in the escape of body immune surveillance, consequently leading to the cell carcinogenesis, it is likely that the upsurge of SPIK expression leads to cancer in chronic HBV and HCV infections. Since up-regulation of SPIK has been demonstrated in many cancer cells, a novel anti-cancer therapeutic strategy has been developed. By suppressing SPIK expression, the apoptotic cell death could be induced. Based on this strategy, any anti-SPIK technology and compound could develop to an anti-cancer agent, particularly to Hepatocellular carcinoma.

Accordingly, this invention provides an inhibitor of SPIK and/or a technology of suppression of over-expression of SPIK in cells. The inhibitors include, but are not limited to: 1) chemical compounds, which can inhibit SPIK transcripts, protein activity, and gene expression, 2) SPIK siRNA (RNAi gene silence or dsRNA of SPIK, 3) DNA anti-sense and 4) anti-SPIK antibody. Further, this invention provides a method of using the inhibitor as an anti-cancer agent to re-instate cancer cell apoptosis (e.g., serine protease dependent cell apoptosis). Since our studies shows HBV and HCV infection can up-regulate SPIK expression, therefore, those inhibitors and technology also can use as a therapeutic agent for HBV/HCV infection by reinstatement of the sensitivity of apoptosis of infected cells.

The strategy for discovery of inhibitors includes the following:
(1) screening chemical compounds that are able to inhibit SPIK activity in vitro using a library or a computer designed siRNA; and
(2) examining and selecting chemical compounds and siRNA such that the working agents would be tested in a cell-based system to assess the efficacy (the capability to induce the cell apoptosis) and toxicity. The agents with low toxicity and high efficacy will further be tested in animals and finally, used in for clinical trials.

Figure 9:
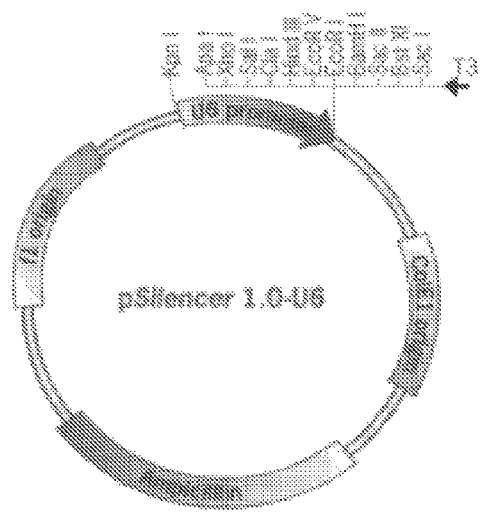
FIG. 9A-9D. siRNA L71 and L183 suppressed SPIK expression in G54 cells and consequently restore the sensitivity of the cells to cell apoptosis.
Figure 9:
Figure 9:
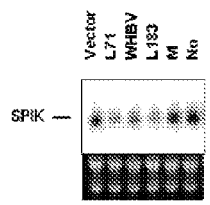
Figure 9:
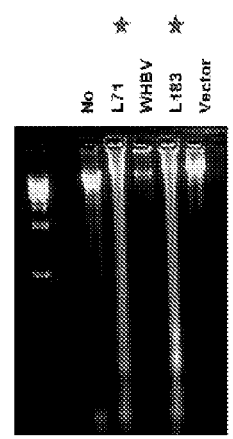

An assay to be used for the above testing includes the following:
a) for discovery of chemical compounds, a high throughput screen system by first expression SPIK in vitro such as yeast, bacteria etc. will be established. Those SPIK inhibitors will then be isolated and purified. Because SPIK is a serine protease inhibitor, which can inhibit trypsin (a serine protease) activity in vitro, therefore, the SPIK activity can be assessed by inhibition of activity of trypsin using the ability to digest fluorescent substrates. Once this system is established, the compound that could restore trypsin activity in our screen system is the compound that can inhibit SPIK activity;
b) for selection of working siRNA and DNA anti-sense, a RNA or DNA SPIK sequence with 19-21 nucleosides would be designed by computer software. SPIK siRNA vector contains siRNA sequences composed of a sense and an anti-sense strands that are complementary to the different parts of the SPIK gene. The sense and anti-sense fragments are linked by a hairpin linker with nine nucleosides (TTCAAGAGA (SEQ ID NO: 5), FIG. 9A). The construct is designed to transcribe the short hairpin RNA utilizing an RNA polymerase III promoter such as U6. A small poly-T structure with six thymidines is added at the 3' terminus of sequence to terminate transcription (FIGS. 9A and B). siRNA sequence is dedicated at the 3' end of the transcript. For example: siRNA L71 and L183. L71 contains sense and anti-sense oligo-nucleoside with the SPIK sequence as: CAG-GCATCTTTCTTCTCAG (SEQ ID NO: 1), starting at 71st base pair just after start codon. L183 contains sense and anti-sense oligo-nucleoside with the SPIK sequence as: GATATATGACCCTGTCTGT (SEQ ID NO: 2), starting at 183rd base pair and ending at 4 nucleosides before the stop codon. Then those siRNA will be transfected into Huh 7 cells, which is hepatoma cell line with over-expressed SPIK. The suppression of SPIK expression can be examined by Northern blot or real time RT-PCR. The inhibition of SPIK expression by L71 and L183 has been confirmed in our laboratory, as shown in FIG. 9, see Example 7.

The working compounds and siRNA would be introduced into cancer cell lines; the apoptosis of these cells will be examined.

The cell lines useful in this invention can be any of the cell lines supplied by ATCC and the stable SPIK expression cell line established by us. Non-limiting examples of cells are liver cancer cell lines: HepG2, Huh 7, Huh 6, Hep3B etc; pancreatic cancer cell line: HPAC, Panc 10.05, Panc 02.13, PL45, Hs 766T etc.; colon cancer cell line: Hs 675.T HS 722 etc.; gastric cancer cell line: N87, SNU, KATO III etc.; skin cancer cell line: Hs 700.5 k; and lung cancer cell line; NCI-H735, H1755.

In certain embodiments, the human hepatoma cell line Huh 7 and HepG2, as well as other cancer cells such as human gastric carcinomas, colorectal tumor, and pancreatic cancer commercially available from ATCC will be used. Those cells are of particular interest because the up-regulation of SPIK expressions was found in these cell lines.

The up-regulation of SPIK in numerous cancer cells as well in hepatoma cell lines has been reported. Those cancer cells include human liver cancer, gastric carcinomas, colorectal tumor and pancreatic cancer etc. The over-expression of SPIK in cancer cells can be examined with Northern Blot with SPIK specific probe or RT-PCR with SPIK primers by comparison with non-cancer cell.

Exemplary libraries include 1) the chemical library with more than 80,000 compounds available from Drexel University, 2) the chemical library from Chemical Diversity (San Diego, Calif.) such as Protein Class Libraries, Pathway/Disease Libraries, etc.

Provided herein are members of the Serine Protease Inhibitor Kazal family, designated herein as SPIK. The full-length protein, and activated forms, and uses thereof are also provided. Proteins encoded by splice variants are also provided.

Assays for identifying effectors, such as small molecules and other conditions, that modulate the activation, expression or activity of SPIK are also provided herein. In exemplary assays, the effects of test compounds on the ability of SPIK to inhibit a serine protease, typically a fluorescently, chromogenically or otherwise detectably labeled substrate, are assessed. SPIK can also be used to produce antibodies.

Nucleic acid molecules encoding the SPIK protein are also provided. The nucleic acid and amino acid sequences of an exemplary full length SPIK are set forth in SEQ ID NOs: 3 and 4. Nucleic acid molecules that encode a catalytically active portion thereof and also those that encode the full-length SPIK are provided. Also provided are nucleic acid molecules that hybridize to such SPIK-encoding nucleic acid along their full length or encode a portion thereof are provided. Hybridization is generally effected under conditions of at least low, generally at least moderate, and often high stringency.

The isolated nucleic acid fragment is DNA, including genomic or cDNA, or is RNA, or can include other components, such as protein nucleic acid. The isolated nucleic acid may include additional components, such as heterologous or native promoters, and other transcriptional and translational regulatory sequences, these genes may be linked to other genes, such as reporter genes or other indicator genes or genes that encode indicators.

Also provided is an isolated nucleic acid molecule that includes the sequence of molecules that is complementary to the nucleotide sequence encoding SPIK or a portion thereof.

Also provided are fragments thereof or oligonucleotides that can be used as probes or primers and that contain at least about 10, 14, 16 nucleotides, generally less than equal to 100, set forth in SEQ ID NO. 3 (or the complement thereof); or contain at least about 30 nucleotides (or the complement thereof) or contain oligonucleotides that hybridize along their full length (or at least about 70, 80 or 90% thereof) to any such fragments or oligonucleotides. The length of the fragments are a function of the purpose for which they are used and/or the complexity of the genome of interest. Generally probes and primers contain less than about 500, 150, 100, 50, 25, 20 nucleotides.

Also provided are peptides that are encoded by such nucleic acid molecules. Included among those polypeptides are SPIK or a polypeptide with amino acid changes such that the specificity and protease inhibitory activity remains substantially unchanged. In particular, a substantially purified mammalian SPIK protein is provided that includes a serine protease inhibitory domain and may additionally include other domains. Also provided is a substantially purified protein including a sequence of amino acids that has at least 60%, 70%, 80%, 90% or about 95%, identity to SPIK where the percentage identity is determined using standard algorithms and gap penalties that maximize the percentage identity. A human SPIK protein is exemplified, although other mammalian SPIK proteins are contemplated. Splice variants of the SPIK, particularly those with a proteolytically active, are contemplated herein.

In other embodiments, substantially purified polypeptides that include a SPIK polypeptide or a catalytically active portion thereof, but that do not include the entire sequence of amino acids set forth in SEQ ID NO. 4 are provided. Among these are polypeptides that include a sequence of amino acids that has at least 60%, 70%, 80%, 85%, 90%, 95% or 100% sequence identity to SEQ ID NO. 4.

In certain embodiments, the SPIK polypeptide is detectable in a body fluid at a level that differs from its level in body fluids in a subject not having a tumor. In other embodiments, the polypeptide is present in a tumor; and a substrate or cofactor for the polypeptide is expressed at levels that differ from its level of expression in a non-tumor cell in the same type of tissue. In other embodiments, the substantially purified the level of expression and/or activity of the SPIK polypeptide in tumor cells differs from its level of expression and/or activity in non-tumor cells. In other embodiments, the SPIK is present in a tumor; and a substrate or cofactor for the SPIK is expressed at levels that differ from its level of expression in a non-tumor cell in the same type of tissue.

In a specific embodiment, a nucleic acid that encodes SPIK is provided. In particular, the nucleic acid includes the sequence of nucleotides set forth in SEQ ID NO. 3 or a portion there of that encodes a polypeptide that inhibits a serine protease.

Also provided are nucleic acid molecules that hybridize under conditions of at least low stringency, generally moderate stringency, more typically high stringency to the SEQ ID NO. 3 or degenerates thereof.

In one embodiment, the isolated nucleic acid fragment hybridizes to a nucleic acid molecule containing the nucleotide sequence set forth in SEQ ID NO: 3 (or degenerates thereof) under high stringency conditions, in one embodiment comprises the sequence of nucleotides set forth in SEQ ID No. 3. A full-length SPIK is set forth in SEQ ID NO. 4 and is encoded by SEQ ID NO. 3 or degenerates thereof.

Also provided are muteins of SPIK particularly muteins in which conservative or non-conservative amino acid substitutions in which inhibitory activity is retained are also contemplated. Hence, provided herein is a serine protease inhibitory—Kazal proteins designated SPIK, and functional domains, especially inhibitory domains thereof, muteins and other derivatives and analogs thereof. Also provided herein are nucleic acids encoding the SPIKs.

Additionally provided herein are antibodies that specifically bind to the SPIK cells, combinations, kits and articles of manufacture that contain the nucleic acid encoding SPIK. Further provided herein are prognostic, diagnostic, therapeutic screening methods using SPIK and the nucleic acids encoding SPIK. Also provided are transgenic non-human animals bearing inactivated genes encoding the SPIK and bearing the genes encoding the SPIK under non-native promoter control are provided. Such animals are useful in animal models of tumor initiation, growth and/or progression models.

Of interest herein are SPIKs that are expressed or are activated in certain tumor or cancer cells such hepatic, lung, prostate, colon and breast cancers. In particular, it is shown herein that SPIK is expressed in hepatic carcinoma, as well as in certain normal cells and tissues. The expression or activation of SPIK in a cell in a subject can be a marker for hepatic, and other cancers.

SPIKs are of interest because they appear to be expressed and/or activated at different levels in tumor cells from normal cells, or have functional activity that is different in tumor cells from normal cells, such as by an alteration in a substrate therefor, or a cofactor. SPIK is of interest because it is expressed or is active in tumor cells. Hence the SPIK provided herein can serve as diagnostic markers for certain tumors. The level of activated SPIK can be diagnostic of hepatic or breast cancer.

Also provided herein are methods of modulating the activity of the SPIK and screening for compounds that modulate, including inhibit, antagonize, agonize or otherwise alter the activity of the SPIK.

SPIK proteins, including, but not limited including splice variants thereof, and nucleic acids encoding SPIKs, and domains, derivatives and analogs thereof are provided herein.

Antibodies that specifically bind to the SPIK, and cells, combinations, kits and articles of manufacture containing the SPIK proteins, domains thereof, or encoding nucleic acids are also provided herein. Transgenic non-human animals bearing inactivated genes encoding SPIK and bearing the genes encoding SPIK, particularly under a non-native promoter control or on an exogenous element, such as a plasmid or artificial chromosome, are additionally provided herein. Also provided are nucleic acid molecules encoding each of SPIK and domains thereof.

Also provided are plasmids containing any of the nucleic acid molecules provided herein. Cells containing the plasmids are also provided. Such cells include, but are not limited to, bacterial cells, yeast cells, fungal cells, plant cells, insect cells and animal cells.

Also provided is a method of producing SPIK by growing the above-described cells under conditions whereby the SPIK is expressed by the cells, and recovering the expressed SPIK protein. Methods for isolating nucleic acid encoding other SPIKs are also provided.

Also provided are cells, generally eukaryotic cells, such as mammalian cells and yeast cells, in which the SPIK protein is expressed on the surface of the cells. Such cells are used in drug screening assays to identify compounds that modulate the activity of the SPIK protein. These assays including in vitro binding assays, and transcription based assays in which signal transduction mediated directly or indirectly, such as via activation of pro-growth factors, by which SPIK is assessed.

Further provided herein are prognostic, diagnostic and therapeutic screening methods using the SPIK protein and the nucleic acids encoding SPIK. In particular, the prognostic, diagnostic and therapeutic screening methods are used for preventing, treating, or for finding agents useful in preventing or treating, tumors or cancers such as hepatic carcinoma.

Also provided are methods for screening for compounds that modulate the activity of SPIK. The compounds are identified by contacting them with the SPIK and a substrate for a serine protease. A change in the amount of substrate cleaved in the presence of the compounds compared to that in the absence of the compound indicates that the compound modulates the activity of the SPIK. Such compounds are selected for further analyses or for use to modulate the activity of the SPIK, such as inhibitors or agonists.

Also provided herein are modulators of the activity of SPIK, especially the modulators obtained according to the screening methods provide herein. Such modulators can have use in treating cancerous conditions, and other neoplastic conditions.

Pharmaceutical composition containing the and/or full-length or other domain of an SPIK protein are provided herein in a pharmaceutically acceptable carrier or excipient are provided herein.

Also provided are articles of manufacture that contain SPIK encoding nucleic acid or protein. The articles contain a) packaging material; b) the polypeptide (or encoding nucleic acid), particularly the single chain thereof; and c) a label indicating that the article is for using ins assays for identifying modulators of the activities of a SPIK protein is provided herein.

Conjugates containing a) a SPIK protein; and b) a targeting agent linked to the SPIK directly or via a linker, wherein the agent facilitates: i) affinity isolation or purification of the conjugate; ii) attachment of the conjugate to a surface; iii) detection of the conjugate; or iv) targeted delivery to a selected tissue or cell, is provided herein. The conjugate can contain a plurality of agents linked thereto. The conjugate can be a chemical conjugate; and it can be a fusion protein.

In yet another embodiment, the targeting agent is a protein or peptide fragment. The protein or peptide fragment can include a protein binding sequence, a nucleic acid binding sequence, a lipid binding sequence, a polysaccharide binding sequence, or a metal binding sequence.

Methods of diagnosing a disease or disorder characterized by detecting an aberrant level of SPIK in a subject is provided. The method can be practiced by measuring the level of the DNA, RNA, protein or functional activity of SPIK. An increase or decrease in the level of the DNA, RNA, protein or functional activity of SPIK, relative to the level of the DNA, RNA, protein or functional activity found in an analogous sample not having the disease or disorder (or other suitable control) is indicative of the presence of the disease or disorder in the subject or other relative any other suitable control.

Combinations are provided herein. The combination can include: a) an inhibitor or activator of the activity of SPIK; and b) an anti-cancer treatment or agent. The SPIK inhibitor or activator and the anti-cancer agent can be formulated in a single pharmaceutical composition or each is formulated in a separate pharmaceutical composition. The SPIK inhibitor or activator can be an antibody or a fragment or binding portion thereof made against the SPIK, such as an antibody that specifically binds to SPIK, or an inhibitor or activator of SPIK activity. Other SPIK inhibitors include, but are not limited to, an antisense nucleic acid or double-stranded RNA (dsRNA), such as RNAi, encoding SPIK, a nucleic acid encoding at least a portion of a gene encoding the SPIK with a heterologous nucleotide sequence inserted therein such that the heterologous sequence inactivates or enhances the biological activity of encoded SPIK or the gene encoding it. For example, the portion of the gene encoding the SPIK can flank the heterologous sequence to promote homologous recombination with a genomic gene encoding the SPIK.

Also, provided are methods for treating or preventing a tumor or cancer in a mammal by administering to a mammal an effective amount of an inhibitor or activator of SPIK, whereby the tumor or cancer is treated or prevented. The SPIK inhibitor used in the treatment or for prophylaxis is administered with a pharmaceutically acceptable carrier or excipient. The mammal treated can be a human. The treatment or prevention method can additionally include administering an anti-cancer treatment or agent simultaneously with or subsequently or before administration of the SPIK inhibitor or activator.

Also provided is a recombinant non-human animal in which an endogenous gene of an SPIK has been deleted or inactivated by homologous recombination or insertional mutagenesis of the animal or an ancestor thereof. A recombinant non-human animal is provided herein, where the gene of an SPIK is under control of a promoter that is not the native promoter of the gene or that is not the native promoter of the gene in the non-human animal or where the nucleic acid encoding the SPIK is heterologous to the non-human animal and the promoter is the native or a non-native promoter or the SPIK is on an extrachromosomal element, such as a plasmid or artificial chromosome.

Also provided are methods of diagnosing the presence of a pre-malignant lesion, a malignancy, or other pathologic condition in a subject, by obtaining a biological sample from the subject; exposing it to a detectable agent that binds to SPIK, where the pathological condition is characterized by the presence or absence of SPIK.

Methods of inhibiting tumor invasion or metastasis or treating a malignant or pre-malignant condition by administering an agent that modulates activity of SPIK. The conditions include, but are not limited to, a condition, such as a tumor, of the breast, cervix, prostate, lung, ovary, liver, or colon.

siNA

This invention comprises compounds, compositions, and methods useful for modulating SPIK gene expression using short interfering nucleic acid (siNA) molecules. This invention also comprises compounds, compositions, and methods useful for modulating the expression and activity of other genes involved in pathways of SPIK gene expression and/or activity by RNA interference (RNAi) using small nucleic acid molecules. In particular, the instant invention features small nucleic acid molecules, such as short interfering nucleic acid (siNA), short interfering RNA (siRNA), double-stranded RNA (dsRNA), micro-RNA (miRNA), and short hairpin RNA (siRNA) molecules and methods used to modulate the expression of SPIK genes A siNA of the invention can be unmodified or chemically-modified. A siNA of the instant invention can be chemically synthesized, expressed from a vector or enzymatically synthesized. The instant invention also features various chemically-modified synthetic short interfering nucleic acid (siNA) molecules capable of modulating SPIK gene expression or activity in cells by RNA interference (RNAi). The use of chemically-modified siNA improves various properties of native siNA molecules through increased resistance to nuclease degradation in vivo and/or through improved cellular uptake. Further, contrary to earlier published studies, siNA having multiple chemical modifications retains its RNAi activity. The siNA molecules of the instant invention provide useful reagents and methods for a variety of therapeutic, diagnostic, target validation, genomic discovery, genetic engineering, and pharmacogenomic applications.

In one embodiment, the invention features a double-stranded short interfering nucleic acid (siNA) molecule that down-regulates expression of SPIK gene, wherein said siNA molecule comprises about 19 to about 21 base pairs.

In one embodiment, the invention features a siNA molecule that down-regulates expression of a SPIK gene, for example, wherein the SPIK gene comprises SPIK encoding sequence. In one embodiment, the invention features a siNA molecule that down-regulates expression of a SPIK gene, for example, wherein the SPIK gene comprises SPIK non-coding sequence or regulatory elements involved in SPIK gene expression.

In one embodiment, the invention features a siNA molecule having RNAi activity against SPIK RNA, wherein the siNA molecule comprises a sequence complementary to any RNA having SPIK encoding sequence. In another embodiment, the invention features a siNA molecule having RNAi activity against SPIK RNA, wherein the siNA molecule comprises a sequence complementary to an RNA having other SPIK encoding sequence, for example other mutant SPIK genes.

In one embodiment, the invention features siNA molecules that inhibit or down regulate expression of genes that encode inhibitors of SPIK. In one embodiment, siNA molecules of the invention are used to down regulate or inhibit the expression of SPIK proteins arising from SPIK haplotype polymorphisms that are associated with a disease or condition, (e.g., cancer). Analysis of SPIK genes, or SPIK protein or RNA levels can be used to identify subjects with such polymorphisms or those subjects who are at risk of developing diseases described herein. These subjects are amenable to treatment, for example, treatment with siNA molecules of the invention and any other composition useful in treating diseases related to SPIK gene expression. As such, analysis of SPIK protein or RNA levels can be used to determine treatment type and the course of therapy in treating a subject. Monitoring of SPIK protein or RNA levels can be used to predict treatment outcome and to determine the efficacy of compounds and compositions that modulate the level and/or activity of certain SPIK proteins associated with disease.

In one embodiment of the invention a siNA molecule comprises an antisense strand comprising a nucleotide sequence that is complementary to a nucleotide sequence or a portion thereof encoding a SPIK protein. The siNA further comprises a sense strand, wherein said sense strand comprises a nucleotide sequence of a SPIK gene or a portion thereof.

In another embodiment, a siNA molecule comprises an antisense region comprising a nucleotide sequence that is complementary to a nucleotide sequence encoding a SPIK protein or a portion thereof. The siNA molecule further comprises a sense region, wherein said sense region comprises a nucleotide sequence of a SPIK gene or a portion thereof.

In another embodiment, the invention features a siNA molecule comprising a nucleotide sequence in the antisense region of the siNA molecule that is complementary to a nucleotide sequence or portion of sequence of a SPIK gene. In another embodiment, the invention features a siNA molecule comprising a region, for example, the antisense region of the siNA construct, complementary to a sequence comprising a SPIK gene sequence or a portion thereof.

In one embodiment, the antisense region of SPIK siNA constructs can comprise a sequence complementary to sequence having any of SEQ ID NOs: 1, 2 or 3. A siNA molecule of the invention can comprise any contiguous SPIK sequence (e.g., about 19 to about 25, or about 18, 19, 20, 21, 22, 23, 24, 25 or 26 contiguous SPIK nucleotides).

In one embodiment of the invention a siNA molecule comprises an antisense strand having about 19 to about 29 (e.g., about 18, 19, 20, 21, 22, 23, 24, 25, 26, 27, 28, 29 or 30) nucleotides, wherein the antisense strand is complementary to a RNA sequence encoding a SPIK protein, and wherein said siNA further comprises a sense strand having about 19 to about 29 (e.g., about 18, 19, 20, 21, 22, 23, 24, 25, 26, 27, 28, 29 or 30) nucleotides, and wherein said sense strand and said antisense strand are distinct nucleotide sequences with at least about 19 complementary nucleotides.

In another embodiment of the invention a siNA molecule of the invention comprises an antisense region having about 19 to about 29 (e.g., about 18, 19, 20, 21, 22, 23, 24, 25, 26, 27, 28, 29 or 30) nucleotides, wherein the antisense region is complementary to a RNA sequence encoding a SPIK protein, and wherein said siNA further comprises a sense region having about 19 to about 29 (e.g., about 18, 19, 20, 21, 22, 23, 24, 25, 26, 27, 28, 29, 30 or more) nucleotides, wherein said sense region and said antisense region comprise a linear molecule with at least about 19 complementary nucleotides.

In one embodiment, a siNA molecule of the invention has RNAi activity that modulates expression of RNA encoded by a SPIK gene. Because SPIK genes can share some degree of sequence homology with each other, siNA molecules can be designed to target a class of SPIK genes or alternately specific SPIK genes (e.g., polymorphic variants) by selecting sequences that are either shared amongst different SPIK targets or alternatively that are unique for a specific SPIK target. Therefore, in one embodiment, the siNA molecule can be designed to target conserved regions of SPIK RNA sequences having homology among several SPIK gene variants so as to target a class of SPIK genes with one siNA molecule. Accordingly, in one embodiment, the siNA molecule of the invention modulates the expression of one or both SPIK alleles in a subject. In another embodiment, the siNA molecule can be designed to target a sequence that is unique to a specific SPIK RNA sequence (e.g., a single SPIK allele or SPIK SNP) due to the high degree of specificity that the siNA molecule requires to mediate RNAi activity.

In one embodiment, nucleic acid molecules of the invention that act as mediators of the RNA interference gene silencing response are double-stranded nucleic acid molecules. In another embodiment, the siNA molecules of the invention consist of duplexes containing about 19 base pairs between oligonucleotides comprising about 19 to about 25 (e.g., about 18, 19, 20, 21, 22, 23, 24, 25 or 26) nucleotides. In yet another embodiment, siNA molecules of the invention comprise duplexes with overhanging ends of about 1 to about 3 (e.g., about 1, 2, or 3) nucleotides, for example, about 21-nucleotide duplexes with about 19 base pairs and 3'-terminal mononucleotide, dinucleotide, or trinucleotide overhangs.

In one embodiment, the invention features one or more chemically-modified siNA constructs having specificity for SPIK expressing nucleic acid molecules, such as RNA encoding a SPIK protein. Non-limiting examples of such chemical modifications include without limitation phosphorothioate internucleotide linkages, 2'-deoxyribonucleotides, 2'-O-methyl ribonucleotides, 2'-deoxy-2'-fluoro ribonucleotides, "universal base" nucleotides, "acyclic" nucleotides, 5-C-methyl nucleotides, and terminal glyceryl and/or inverted deoxy a basic residue incorporation. These chemical modifications, when used in various siNA constructs, are Shown to preserve RNAi activity in cells while at the same time, dramatically increasing the serum stability of these compounds. Furthermore, contrary to the data published by Parrish et al., supra, applicant demonstrates that multiple (greater than one) phosphorothioate substitutions are well-tolerated and confer substantial increases in serum stability for modified siNA constructs.

In one embodiment, a siNA molecule of the invention comprises modified nucleotides while maintaining the ability to mediate RNAi. The modified nucleotides can be used to improve in vitro or in vivo characteristics such as stability, activity, and/or bioavailability. For example, a siNA molecule of the invention can comprise modified nucleotides as a percentage of the total number of nucleotides present in the siNA molecule. As such, a siNA molecule of the invention can generally comprise about 5% to about 100% modified nucleotides (e.g., 5%, 10%, 15%, 20%, 25%, 30%, 35%, 40%, 45%, 50%, 55%, 60%, 65%, 70%, 75%, 80%, 85%, 90%, 95% or 100% modified nucleotides). The actual percentage of modified nucleotides present in a given siNA molecule will depend on the total number of nucleotides present in the siNA. If the siNA molecule is single stranded, the percent modification can be based upon the total number of nucleotides present in the single stranded siNA molecules. Likewise, if the siNA molecule is double stranded, the percent modification can be based upon the total number of nucleotides present in the sense strand, antisense strand, or both the sense and antisense strands.

One aspect of the invention features a double-stranded short interfering nucleic acid (siNA) molecule that down-regulates expression of a SPIK gene. In one embodiment, a double stranded siNA molecule comprises one or more chemical modifications and each strand of the double-stranded siNA is about 21 nucleotides long. In one embodiment, the double-stranded siNA molecule does not contain any ribonucleotides. In another embodiment, the double-stranded siNA molecule comprises one or more ribonucleotides. In one embodiment, each strand of the double-stranded siNA molecule comprises about 19 to about 29 (e.g., about 18, 19, 20, 21, 22, 23, 24, 25, 26, 27, 28, 29, or 30) nucleotides, wherein each strand comprises about 19 nucleotides that are complementary to the nucleotides of the other strand. In one embodiment, one of the strands of the double-stranded siNA molecule comprises a nucleotide sequence that is complementary to a nucleotide sequence or a portion thereof of the SPIK gene, and the second strand of the double-stranded siNA molecule comprises a nucleotide sequence substantially similar to the nucleotide sequence of the SPIK gene or a portion thereof.

In another embodiment, the invention features a double-stranded short interfering nucleic acid (siNA) molecule that down-regulates expression of a SPIK gene comprising an antisense region, wherein the antisense region comprises a nucleotide sequence that is complementary to a nucleotide sequence of the SPIK gene or a portion thereof, and a sense region, wherein the sense region comprises a nucleotide sequence substantially similar to the nucleotide sequence of the SPIK gene or a portion thereof. In one embodiment, the antisense region and the sense region each comprise about 19 to about 23 (e.g. about 18, 19, 20, 21, 22, 23 or 24) nucleotides, wherein the antisense region comprises about 19 nucleotides that are complementary to nucleotides of the sense region.

In another embodiment, the invention features a double-stranded short interfering nucleic acid (siNA) molecule that down-regulates expression of a SPIK gene comprising a sense region and an antisense region, wherein the antisense region comprises a nucleotide sequence that is complementary to a nucleotide sequence of RNA encoded by the SPIK gene or a portion thereof and the sense region comprises a nucleotide sequence that is complementary to the antisense region. In one embodiment, a siNA molecule of the invention comprises blunt ends, i.e., ends that do not include any overhanging nucleotides.

In one embodiment, any siNA molecule of the invention can comprise one or more blunt ends, i.e. where a blunt end does not have any overhanging nucleotides. In a non-limiting example, a blunt ended siNA molecule has a number of base pairs equal to the number of nucleotides present in each strand of the siNA molecule. In another example, a siNA molecule comprises one blunt end, for example wherein the 5'-end of the antisense strand and the 3'-end of the sense strand do not have any overhanging nucleotides. In another example, a siNA molecule comprises one blunt end, for example wherein the 3'-end of the antisense strand and the 5'-end of the sense strand do not have any overhanging nucleotides. In another example, a siNA molecule comprises two blunt ends, for example wherein the 3'-end of the antisense strand and the 5'-end of the sense strand as well as the 5'-end of the antisense strand and 3'-end of the sense strand do not have any overhanging nucleotides. A blunt ended siNA molecule can comprise, for example, from about 18 to about 30 nucleotides (e.g., about 18, 19, 20, 21, 22, 23, 24, 25, 26, 27, 28, 29, or 30 nucleotides). Other nucleotides present in a blunt ended siNA molecule can comprise mismatches, bulges, loops, or wobble base pairs, for example, to modulate the activity of the siNA molecule to mediate RNA interference.

By "blunt ends" is meant symmetric termini or termini of a double stranded siNA molecule having no overhanging nucleotides. The two strands of a double stranded siNA molecule align with each other without over-hanging nucleotides at the termini. For example, a blunt ended siNA construct comprises terminal nucleotides that are complementary between the sense and antisense regions of the siNA molecule.

In one embodiment, the invention features a double-stranded short interfering nucleic acid (siNA) molecule that down-regulates expression of a SPIK gene, wherein the siNA molecule is assembled from two separate oligonucleotide fragments wherein one fragment comprises the sense region and the second fragment comprises the antisense region of the siNA molecule. The sense region can be connected to the antisense region via a linker molecule, such as a polynucleotide linker or a non-nucleotide linker.

In one embodiment, the invention features double-stranded short interfering nucleic acid (siNA) molecule that down-regulates expression of a SPIK gene, wherein the siNA molecule comprises about 19 to about 21 base pairs, and wherein each strand of the siNA molecule comprises one or more chemical modifications. In another embodiment, one of the strands of the double-stranded siNA molecule comprises a nucleotide sequence that is complementary to a nucleotide sequence of a SPIK gene or a portion thereof, and the second strand of the double-stranded siNA molecule comprises a nucleotide sequence substantially similar to the nucleotide sequence or a portion thereof of the SPIK gene. In another embodiment, one of the strands of the double-stranded siNA molecule comprises a nucleotide sequence that is complementary to a nucleotide sequence of a SPIK gene or a portion thereof, and the second strand of the double-stranded siNA molecule comprises a nucleotide sequence substantially similar to the nucleotide sequence or a portion thereof of the SPIK gene. In another embodiment, each strand of the siNA molecule comprises about 19 to about 23 nucleotides, and each strand comprises at least about 19 nucleotides that are complementary to the nucleotides of the other strand. The SPIK gene can comprise, for example, sequence as set forth in SEQ ID NOs: 1, 2, or 3.

In one embodiment, a siNA molecule of the invention comprises no ribonucleotides. In another embodiment, a siNA molecule of the invention comprises ribonucleotides.

In one embodiment, a siNA molecule of the invention comprises an antisense region comprising a nucleotide sequence that is complementary to a nucleotide sequence of a SPIK gene or a portion thereof, and the siNA further comprises a sense region comprising a nucleotide sequence substantially similar to the nucleotide sequence of the SPIK gene or a portion thereof. In another embodiment, the antisense region and the sense region each comprise about 19 to about 23 nucleotides and the antisense region comprises at least about 19 nucleotides that are complementary to nucleotides of the sense region. The SPIK gene can comprise, for example, sequences as set forth in SEQ ID NO: 1, 2, or 3.

In one embodiment, a siNA molecule of the invention comprises a sense region and an antisense region, wherein the antisense region comprises a nucleotide sequence that is complementary to a nucleotide sequence of RNA encoded by a SPIK gene, or a portion thereof, and the sense region comprises a nucleotide sequence that is complementary to the antisense region. In another embodiment, the siNA molecule is assembled from two separate oligonucleotide fragments, wherein one fragment comprises the sense region and the second fragment comprises the antisense region of the siNA molecule. In another embodiment, the sense region is connected to the antisense region via a linker molecule. In another embodiment, the sense region is connected to the antisense region via a linker molecule, such as a nucleotide or non-nucleotide linker. The SPIK gene can comprise, for example, sequences as set forth in SEQ ID NO: 1, 2, or 3.

In one embodiment, the invention features a double-stranded short interfering nucleic acid (siNA) molecule that down-regulates expression of a SPIK gene comprising a sense region and an antisense region, wherein the antisense region comprises a nucleotide sequence that is complementary to a nucleotide sequence of RNA encoded by the SPIK gene or a portion thereof and the sense region comprises a nucleotide sequence that is complementary to the antisense region, and wherein the siNA molecule has one or more modified pyrimidine and/or purine nucleotides. In one embodiment, the pyrimidine nucleotides in the sense region are 2'-O-methylpyrimidine nucleotides or 2'-deoxy-2'-fluoro pyrimidine nucleotides and the purine nucleotides present in the sense region are 2'-deoxy purine nucleotides. In another embodiment, the pyrimidine nucleotides in the sense region are 2'-deoxy-2'-fluoro pyrimidine nucleotides and the purine nucleotides present in the sense region are 2'-O-methyl purine nucleotides. In another embodiment, the pyrimidine nucleotides in the sense region are 2'-deoxy-2'-fluoro pyrimidine nucleotides and the purine nucleotides present in the sense region are 2'-deoxy purine nucleotides. In one embodiment, the pyrimidine nucleotides in the antisense region are 2'-deoxy-2'-fluoro pyrimidine nucleotides and the purine nucleotides present in the antisense region are 2'-O-methyl or 2'-deoxy purine nucleotides. In another embodiment of any of the above-described siNA molecules, any nucleotides present in a non-complementary region of the sense strand (e.g. overhang region) are 2'-deoxy nucleotides.

In one embodiment, the invention features a double-stranded short interfering nucleic acid (siNA) molecule that down-regulates expression of a SPIK gene, wherein the siNA molecule is assembled from two separate oligonucleotide fragments wherein one fragment comprises the sense region and the second fragment comprises the antisense region of the siNA molecule, and wherein the fragment comprising the sense region includes a terminal cap moiety at the 5'-end, the 3'-end, or both of the 5' and 3' ends of the fragment. In another embodiment, the terminal cap moiety is an inverted deoxy abasic moiety or glyceryl moiety. In another embodiment, each of the two fragments of the siNA molecule comprise about 21 nucleotides.

In one embodiment, the invention features a siNA molecule comprising at least one modified nucleotide, wherein the modified nucleotide is a 2'-deoxy-2'-fluoro nucleotide. The siNA can be, for example, of length between about 12 and about 36 nucleotides. In another embodiment, all pyrimidine nucleotides present in the siNA are 2'-deoxy-2'-fluoro pyrimidine nucleotides. In another embodiment, the modified nucleotides in the siNA include at least one 2'-deoxy-2'-fluoro cytidine or 2'-deoxy-2'-fluoro uridine nucleotide. In another embodiment, the modified nucleotides in the siNA include at least one 2'-fluoro cytidine and at least one 2'-deoxy-2'-fluoro uridine nucleotides. In another embodiment, all uridine nucleotides present in the siNA are 2'-deoxy-2'-fluoro uridine nucleotides. In another embodiment, all cytidine nucleotides present in the siNA are 2'-deoxy-2'-fluoro cytidine nucleotides. In another embodiment, all adenosine nucleotides present in the siNA are 2'-deoxy-2'-fluoro adenosine nucleotides. In another embodiment, all guanosine nucleotides present in the siNA are 2'-deoxy-2'-fluoro guanosine nucleotides. The siNA can further comprise at least one modified internucleotidic linkage, such as phosphorothioate linkage. In another embodiment, the 2'-deoxy-2'-fluoronucleotides are present at specifically selected locations in the siNA that are sensitive to cleavage by ribonucleases, such as locations having pyrimidine nucleotides.

In one embodiment, the invention features a method of increasing the stability of a siNA molecule against cleavage by ribonucleases comprising introducing at least one modified nucleotide into the siNA molecule, wherein the modified nucleotide is a 2'-deoxy-2'-fluoro nucleotide. In another embodiment, all pyrimidine nucleotides present in the siNA are 2'-deoxy-2'-fluoro pyrimidine nucleotides. In another embodiment, the modified nucleotides in the siNA include at least one 2'-deoxy-2'-fluoro cytidine or 2'-deoxy-2'-fluoro uridine nucleotide. In another embodiment, the modified nucleotides in the siNA include at least one 2'-fluoro cytidine and at least one 2'-deoxy-2'-fluoro uridine nucleotides. In another embodiment, all uridine nucleotides present in the siNA are 2'-deoxy-2'-fluoro uridine nucleotides. In another embodiment, all cytidine nucleotides present in the siNA are 2'-deoxy-2'-fluoro cytidine nucleotides. In another embodiment, all adenosine nucleotides present in the siNA are 2'-deoxy-2'-fluoro adenosine nucleotides. In another embodiment, all guanosine nucleotides present in the siNA are 2'-deoxy-2'-fluoro guanosine nucleotides. The siNA can further comprise at least one modified internucleotidic linkage, such as phosphorothioate linkage. In another embodiment, the 2'-deoxy-2'-fluoronucleotides are present at specifically selected locations in the siNA that are sensitive to cleavage by ribonucleases, such as locations having pyrimidine nucleotides.

In one embodiment, the invention features a double-stranded short interfering nucleic acid (siNA) molecule that down-regulates expression of a SPIK gene comprising a sense region and an antisense region, wherein the antisense region comprises a nucleotide sequence that is complementary to a nucleotide sequence of RNA encoded by the SPIK gene or a portion thereof and the sense region comprises a nucleotide sequence that is complementary to the antisense region, and wherein the purine nucleotides present in the antisense region comprise 2'-deoxy-purine nucleotides. In an alternative embodiment, the purine nucleotides present in the antisense region comprise 2'-O-methyl purine nucleotides. In either of the above embodiments, the antisense region can comprise a phosphorothioate internucleotide linkage at the 3' end of the antisense region. Alternatively, in either of the above embodiments, the antisense region can comprise a glyceryl modification at the 3' end of the antisense region. In another embodiment of any of the above-described siNA molecules, any nucleotides present in a non-complementary region of the antisense strand (e.g. overhang region) are 2'-deoxy nucleotides.

In one embodiment, the invention features a double-stranded short interfering nucleic acid (siNA) molecule that down-regulates expression of a SPIK gene, wherein the siNA molecule is assembled from two separate oligonucleotide fragments wherein one fragment comprises the sense region and the second fragment comprises the antisense region of the siNA molecule. In another embodiment about 19 nucleotides of each fragment of the siNA molecule are base-paired to the complementary nucleotides of the other fragment of the siNA molecule and wherein at least two 3' terminal nucleotides of each fragment of the siNA molecule are not base-paired to the nucleotides of the other fragment of the siNA molecule. In one embodiment, each of the two 3' terminal nucleotides of each fragment of the siNA molecule is a 2'-deoxy-pyrimidine nucleotide, such as a 2'-deoxy-thymidine. In another embodiment, all 21 nucleotides of each fragment of the siNA molecule are base-paired to the complementary nucleotides of the other fragment of the siNA molecule. In another embodiment, about 19 nucleotides of the antisense region are base-paired to the nucleotide sequence or a portion thereof of the RNA encoded by the SPIK gene. In another embodiment, about 21 nucleotides of the antisense region are base-paired to the nucleotide sequence or a portion thereof of the RNA encoded by the SPIK gene. In any of the above embodiments, the 5'-end of the fragment comprising said antisense region can optionally includes a phosphate group.

In one embodiment, the invention features a chemically synthesized double stranded RNA molecule that directs cleavage of a SPIK RNA via RNA interference, wherein each strand of said RNA molecule is about 21 to about 23 nucleotides in length; one strand of the RNA molecule comprises nucleotide sequence having sufficient complementarity to the SPIK RNA for the RNA molecule to direct cleavage of the SPIK RNA via RNA interference; and wherein at least one strand of the RNA molecule comprises one or more chemically modified nucleotides described herein, such as deoxynucleotides, 2'-O-methyl nucleotides, 2'-deoxy-2'-fluoro nucleotides, 2'-O-methoxyethyl nucleotides etc.

In one embodiment, the invention features a medicament comprising a siNA molecule of the invention.

In one embodiment, the invention features an active ingredient comprising a siNA molecule of the invention.

In one embodiment, the invention features the use of a double-stranded short interfering nucleic acid (siNA) molecule to down-regulate expression of a SPIK gene, wherein the siNA molecule comprises one or more chemical modifications and each strand of the double-stranded siNA is about 18 to about 28 or more (e.g., 17, 18, 19, 20, 21, 22, 23, 24, 25, 26, 27, 28, 29 or more) nucleotides long.

In one embodiment, the invention features the use of a double-stranded short interfering nucleic acid (siNA) molecule that inhibits expression of a SPIK gene, wherein one of the strands of the double-stranded siNA molecule is an antisense strand which comprises nucleotide sequence that is complementary to nucleotide sequence of SPIK RNA or a portion thereof, the other strand is a sense strand which comprises nucleotide sequence that is complementary to a nucleotide sequence of the antisense strand and wherein a majority of the pyrimidine nucleotides present in the double-stranded siNA molecule comprises a sugar modification.

In one embodiment, the invention features a double-stranded short interfering nucleic acid (siNA) molecule that inhibits expression of a SPIK gene, wherein one of the strands of the double-stranded siNA molecule is an antisense strand which comprises nucleotide sequence that is complementary to nucleotide sequence of SPIK RNA or a portion thereof, wherein the other strand is a sense strand which comprises nucleotide sequence that is complementary to a nucleotide sequence of the antisense strand and wherein a majority of the pyrimidine nucleotides present in the double-stranded siNA molecule comprises a sugar modification.

In one embodiment, the invention features a double-stranded short interfering nucleic acid (siNA) molecule that inhibits expression of a SPIK gene, wherein one of the strands of the double-stranded siNA molecule is an antisense strand which comprises nucleotide sequence that is complementary to nucleotide sequence of SPIK RNA that encodes a protein or portion thereof, the other strand is a sense strand which comprises nucleotide sequence that is complementary to a nucleotide sequence of the antisense strand and wherein a majority of the pyrimidine nucleotides present in the double-stranded siNA molecule comprises a sugar modification. In one embodiment, the invention features a double-stranded short interfering nucleic acid (siNA) molecule that inhibits expression of a SPIK gene, wherein one of the strands of the double-stranded siNA molecule is an antisense strand which comprises nucleotide sequence that is complementary to nucleotide sequence of SPIK RNA or a portion thereof, the other strand is a sense strand which comprises nucleotide sequence that is complementary to a nucleotide sequence of the antisense strand and wherein a majority of the pyrimidine nucleotides present in the double-stranded siNA molecule comprises a sugar modification. In one embodiment, each strand of the siNA molecule comprises about 18 to about 29 or more (e.g., about 17, 18, 19, 20, 21, 22, 23, 24, 25, 26, 27, 28, 29, 30 or more) nucleotides, wherein each strand comprises at least about 18 nucleotides that are complementary to the nucleotides of the other strand. In another embodiment, the siNA molecule is assembled from two oligonucleotide fragments, wherein one fragment comprises the nucleotide sequence of the antisense strand of the siNA molecule and a second fragment comprises nucleotide sequence of the sense region of the siNA molecule. In yet another embodiment, the sense strand is connected to the antisense strand via a linker molecule, such as a polynucleotide linker or a non-nucleotide linker. In a further embodiment, the pyrimidine nucleotides present in the sense strand are 2'-deoxy-2'fluoro pyrimidine nucleotides and the purine nucleotides present in the sense region are 2'-deoxy purine nucleotides. In another embodiment, the pyrimidine nucleotides present in the sense strand are 2'-deoxy-2'fluoro pyrimidine nucleotides and the purine nucleotides present in the sense region are 2'-O-methyl purine nucleotides. In still another embodiment, the pyrimidine nucleotides present in the antisense strand are 2'-deoxy-2'-fluoro pyrimidine nucleotides and any purine nucleotides present in the antisense strand are 2'-deoxy purine nucleotides. In another embodiment, the antisense strand comprises one or more 2'-deoxy-2'-fluoro pyrimidine nucleotides and one or more 2'-O-methyl purine nucleotides. In another embodiment, the pyrimidine nucleotides present in the antisense strand are 2'-deoxy-2'-fluoro pyrimidine nucleotides and any purine nucleotides present in the antisense strand are 2'-O-methyl purine nucleotides. In a further embodiment the sense strand comprises a 3'-end and a 5'-end, wherein a terminal cap moiety (e.g., an inverted deoxy abasic moiety or inverted deoxy nucleotide moiety such as inverted thymidine) is present at the 5'-end, the 3'-end, or both of the 5' and 3' ends of the sense strand. In another embodiment, the antisense strand comprises a phosphorothioate internucleotide linkage at the 3' end of the antisense strand. In another embodiment, the antisense strand comprises a glyceryl modification at the 3' end. In another embodiment, the 5'-end of the antisense strand optionally includes a phosphate group.

In one embodiment, the invention features a double-stranded short interfering nucleic acid (siNA) molecule that inhibits expression of a SPIK gene, wherein one of the strands of the double-stranded siNA molecule is an antisense strand which comprises nucleotide sequence that is complementary to nucleotide sequence of SPIK RNA or a portion thereof, wherein the other strand is a sense strand which comprises nucleotide sequence that is complementary to a nucleotide sequence of the antisense strand and wherein a majority of the pyrimidine nucleotides present in the double-stranded siNA molecule comprises a sugar modification, and wherein each of the two strands of the siNA molecule comprises about 21 nucleotides. In one embodiment, about 21 nucleotides of each strand of the siNA molecule are base-paired to the complementary nucleotides of the other strand of the siNA molecule. In another embodiment, about 19 nucleotides of each strand of the siNA molecule are base-paired to the complementary nucleotides of the other strand of the siNA molecule, wherein at least two 3' terminal nucleotides of each strand of the siNA molecule are not base-paired to the nucleotides of the other strand of the siNA molecule. In another embodiment, each of the two 3' terminal nucleotides of each fragment of the siNA molecule is a 2'-deoxy-pyrimidine, such as 2'-deoxy-thymidine. In another embodiment, each strand of the siNA molecule is base-paired to the complementary nucleotides of the other strand of the siNA molecule. In another embodiment, about 19 nucleotides of the antisense strand are base-paired to the nucleotide sequence of the SPIK RNA or a portion thereof. In another embodiment, about 21 nucleotides of the antisense strand are base-paired to the nucleotide sequence of the SPIK RNA or a portion thereof.

In one embodiment, the invention features a double-stranded short interfering nucleic acid (siNA) molecule that inhibits expression of a SPIK gene, wherein one of the strands of the double-stranded siNA molecule is an antisense strand which comprises nucleotide sequence that is complementary to nucleotide sequence of SPIK RNA or a portion thereof, the other strand is a sense strand which comprises nucleotide sequence that is complementary to a nucleotide sequence of the antisense strand and wherein a majority of the pyrimidine nucleotides present in the double-stranded siNA molecule comprises a sugar modification, and wherein the 5'-end of the antisense strand optionally includes a phosphate group.

In one embodiment, the invention features a double-stranded short interfering nucleic acid (siNA) molecule that inhibits expression of a SPIK gene, wherein one of the strands of the double-stranded siNA molecule is an antisense strand which comprises nucleotide sequence that is complementary to nucleotide sequence of SPIK RNA or a portion thereof, the other strand is a sense strand which comprises nucleotide sequence that is complementary to a nucleotide sequence of the antisense strand and wherein a majority of the pyrimidine nucleotides present in the double-stranded siNA molecule comprises a sugar modification, and wherein the nucleotide sequence or a portion thereof of the antisense strand is complementary to a nucleotide sequence of the untranslated region or a portion thereof of the SPIK RNA.

In one embodiment, the invention features a double-stranded short interfering nucleic acid (siNA) molecule that inhibits expression of a SPIK gene, wherein one of the strands of the double-stranded siNA molecule is an antisense strand which comprises nucleotide sequence that is complementary to nucleotide sequence of SPIK RNA or a portion thereof, wherein the other strand is a sense strand which comprises nucleotide sequence that is complementary to a nucleotide sequence of the antisense strand, wherein a majority of the pyrimidine nucleotides present in the double-stranded siNA molecule comprises a sugar modification, and wherein the nucleotide sequence of the antisense strand is complementary to a nucleotide sequence of the SPIK RNA or a portion thereof that is present in the SPIK RNA.

In one embodiment, the invention features a composition comprising a siNA molecule of the invention in a pharmaceutically acceptable carrier or diluent.

In a non-limiting example, the introduction of chemically-modified nucleotides into nucleic acid molecules provides a powerful tool in overcoming potential limitations of in vivo stability and bioavailability inherent to native RNA molecules that are delivered exogenously. For example, the use of chemically-modified nucleic acid molecules can enable a lower dose of a particular nucleic acid molecule for a given therapeutic effect since chemically-modified nucleic acid molecules tend to have a longer half-life in serum. Furthermore, certain chemical modifications can improve the bioavailability of nucleic acid molecules by targeting particular cells or tissues and/or improving cellular uptake of the nucleic acid molecule. Therefore, even if the activity of a chemically-modified nucleic acid molecule is reduced as compared to a native nucleic acid molecule, for example, when compared to an all-RNA nucleic acid molecule, the overall activity of the modified nucleic acid molecule can be greater than that of the native molecule due to improved stability and/or delivery of the molecule. Unlike native unmodified siNA, chemically-modified siNA can also minimize the possibility of activating interferon activity in humans.

In any of the embodiments of siNA molecules described herein, the antisense region of a siNA molecule of the invention can comprise a phosphorothioate internucleotide linkage at the 3'-end of said antisense region. In any of the embodiments of siNA molecules described herein, the antisense region can comprise about one to about five phosphorothioate internucleotide linkages at the 5'-end of said antisense region. In any of the embodiments of siNA molecules described herein, the 3'-terminal nucleotide overhangs of a siNA molecule of the invention can comprise ribonucleotides or deoxyribonucleotides that are chemically-modified at a nucleic acid sugar, base, or backbone. In any of the embodiments of siNA molecules described herein, the 3'-terminal nucleotide overhangs can comprise one or more universal base ribonucleotides. In any of the embodiments of siNA molecules described herein, the 3'-terminal nucleotide overhangs can comprise one or more acyclic nucleotides.

One embodiment of the invention provides an expression vector comprising a nucleic acid sequence encoding at least one siNA molecule of the invention in a manner that allows expression of the nucleic acid molecule. Another embodiment of the invention provides a mammalian cell comprising such an expression vector. The mammalian cell can be a human cell. The siNA molecule of the expression vector can comprise a sense region and an antisense region. The antisense region can comprise sequence complementary to a RNA or DNA sequence encoding SPIK and the sense region can comprise sequence complementary to the antisense region. The siNA molecule can comprise two distinct strands having complementary sense and antisense regions. The siNA molecule can comprise a single strand having complementary sense and antisense regions.

As used herein, the term "hybridizes under low stringency, medium stringency, high stringency, or very high stringency conditions" describes conditions for hybridization and washing. Guidance for performing hybridization reactions can be found in Current Protocols in Molecular Biology, John Wiley & Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6.times.sodium chloride/sodium citrate (SSC) at about 45° C., followed by two washes in 0.2×SSC, 0.1% SDS at least at 50° C. (the temperature of the washes can be increased to 55 C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6.times.SSC at about 45.degree. C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C.

The invention provides a method for treating or preventing a neoplastic disease, in a mammal, comprising administering to a mammal an effective amount of an inhibitor of SPIK expression or activity. The invention further provides a method wherein the inhibitor is an antibody that specifically binds to the polypeptide, or a fragment or derivative of the antibody containing a binding domain thereof, wherein the antibody is a polyclonal antibody or a monoclonal antibody.

The invention provides a method for treating or preventing a neoplastic disease, in a mammal, comprising administering to a mammal an effective amount of an inhibitor of a SPIK polypeptide.

The invention provides a method of inhibiting tumor initiation, growth or progression or treating a malignant or pre-malignant condition, comprising administering an agent that inhibits SPIK inhibition of a serine protease. The invention further provides a method wherein the condition is a condition of the liver or breast. The invention further provides a method wherein the agent is an antisense oligonucleotide, dsRNA, siNA, compound, or an antibody. The invention further provides a method comprising administering another treatment or agent selected from anti-tumor and anti-angiogenic treatments or agents.

The invention provides a method for treating HBV and/or HCV infection, in a mammal, comprising administering to a mammal an effective amount of an inhibitor of SPIK expression or activity. The invention further provides a method wherein the inhibitor is an antibody that specifically binds to the polypeptide, or a fragment or derivative of the antibody containing a binding domain thereof, wherein the antibody is a polyclonal antibody or a monoclonal antibody. The invention further provides a method wherein the agent is an antisense oligonucleotide, dsRNA, siNA, compound, or an antibody. The invention further provides a method further comprising administering another treatment or agent selected from anti-tumor, anti-viral, and anti-angiogenic treatments or agents.

The invention provides a method of detecting neoplastic disease, comprising: detecting a polypeptide that comprises a SPIK polypeptide in a biological sample, wherein the amount detected differs from the amount of polypeptide detected from a subject who does not have neoplastic disease.

The invention further provides a method wherein the biological sample is selected from the group consisting of blood, urine, saliva, tears, synovial fluid, sweat, interstitial fluid, cerebrospinal fluid, ascites fluid, tumor tissue biopsy and circulating tumor cells.

The invention provides a method of identifying potentially therapeutically effective agents comprising determining the ability of the agents to modulates SPIK serine protease inhibitory activity in apoptosis sensitive cells exposed to apoptotic agents, wherein the agent is determined to have potential therapeutic efficacy if the apoptosis of the cells in response to the agents changes compared to control cells not exposed to the agent.

The invention provides a method for determining whether an agent may be an apoptosis inhibitor comprising: (a) contacting the agent in vitro with a cell that expresses a SPIK protein; (b) determining the expression level of the SPIK protein in the cell; and (c) determining whether the expression level determined in step (b) is lower than the SPIK protein expression level determined in the absence of the agent, such lower expression level indicating that the agent may be an apoptosis inhibitor.

The invention provides a method for determining whether an agent may be an apoptosis inducer comprising: (a) contacting the agent in vitro with a cell that expresses a SPIK protein; (b) determining the expression level of the SPIK protein in the cell; and (c) determining whether the expression level determined in step (b) is greater than the SPIK protein expression level determined in the absence of the agent, such greater expression level indicating that the agent may be an apoptosis inducer. The invention further provides a method wherein the SPIK protein comprises the amino acid sequence as set forth in SEQ ID NO: 4. The invention further provides a method wherein the cell is a liver cell.

The invention provides a method of screening for a compound that inhibits, diminishes, or modulates anti-apoptotic activity in an eukaryotic cell, said method comprising: (a) introducing into eukaryotic cells an expression vector comprising a polynucleotide encoding a SPIK polypeptide having anti-apoptotic activity, (b) treating one fraction of said cells with a candidate compound and leaving a second fraction of said cells untreated as a control, (c) treating both fractions of cells with an agent that induces cell death, and (d) detecting an inhibition, diminution or modulation in anti-apoptotic activity in the fraction of cells treated with the candidate compound in comparison to the untreated control, thereby screening for a compound that inhibits, diminishes, or modulates anti-apoptotic activity in an eukaryotic cell.

The invention further provides a method wherein said compound is one or more members selected from the group consisting of a polypeptide, a polynucleotide, an amino acid, a nucleotide, and a chemical. The invention further provides a method wherein said compound is one or more members selected from the group consisting of a modified polypeptide and a modified polynucleotide. The invention further provides a method wherein said compound is a polyclonal antibody or a monoclonal antibody. The invention further provides a method wherein said compound is a non-functional anti-apoptotic polypeptide. The invention further provides a method wherein said compound is a DNA oligonucleotide or a RNA oligonucleotide that is complementary to said polynucleotide.

Apoptosis

Apoptosis is distinguished from necrosis, the other well recognized form of cell death. Sudden anoxia, thermal extremes, or chemical toxicity cause necrosis. Whole areas of tissue die after these injuries and individual cells have indistinct cytological appearances and disrupted membranes. Apoptotic cells, on the other hand, are decreased in size compared to their viable counterparts due to decreased cell water and loss of membrane-bound cytoplasmic blebs.sup.7, 8. The nuclei of apoptotic cells are homogeneously condensed and often fragmented. Internucleosomal double-stranded cleavage of nuclear DNA correlates closely with these nuclear morphological changes of apoptosis.sup.8. Despite nuclear fragmentation and cytoplasmic blebbing, apoptotic cells retain their energy supply for an extended period of time and their plasma membranes remain intact.sup.7,8. In vivo, apoptosis occurs most commonly in individual cells that are scattered among non-apoptotic, normal neighbors. Specific molecules on the surface of the apoptotic cells leads to their prompt recognition and phagocytosis by macrophages.sup.7,8. This rapid removal of individual cells makes apoptosis much less apparent than necrosis, in vivo. Most chemotherapeutic agents used to treat acute leukemia induce apoptosis in vitro in leukemic cells lines and freshly isolated leukemic cells. Apoptosis has been demonstrated in the blood and bone marrow of patients receiving combined chemotherapy for acute leukemia. Thus, the measurement of apoptosis in vitro should provide a means to assay for chemosensitivity of a purified leukemic cell population.

Using a population of cells, apoptosis can be identified by the cleavage of DNA at internucleosomal sites. This procedure requires DNA extraction, processing, separation by size, and a means of quantifying intact and cleaved DNA. By examining individual cells within a population, the morphological appearance of apoptosis can be discerned by decreased cell size with condensed, often fragmented, nuclei.sup.7. A more sensitive morphological test for apoptosis is the terminal deoxynucleotidyl transferase (Tdt)-linked labeling of DNA strand ends which gives an extremely intense signal in apoptotic cells as compared to nonapoptotic ones.sup.19. However, these morphological methods for detecting apoptosis require cytological or histological preparations which must be examined by light microscopy, fluorescence microscopy, or fluorescence-activated cytometry.

Apoptosis is classified as caspase dependent cell apoptosis (CDCA) and serine protease dependent cell apoptosis (SPDCA) (27, 28). The difference between CDCA and SPDCA is that the critical proteases responsible for the apoptotic process are caspases in CDCA, and serine proteases in SPDCA.

CDCA can be triggered by cytotoxic cytokines via the "death receptor" pathway. The end point is activation of a wide variety of intracellular caspases, leading to the proteolysis of cellular constituents, and the activation of endonucleases that ultimately degrade the cell's chromatin (29-31).

The death receptor pathway initiates through the binding of cytokines such as FAS ligand (FASL) and tumor necrosis factor (TNF-α) to their receptor at the plasma membrane. This binding induces the recruitment of several adapter proteins such as FADD (Fas associated death domain protein), TRADD (TNF-R1 associated death domain protein), and proenzymes (procaspase 8/procaspase 10) to form a complex usually referred to as DISC (death inducing signaling complex) (32). The proteolysis of caspase 8 and 10 in the DISC activates the executioner caspases such as caspase-3 and caspase-7, resulting in the degradation of chromosomal DNA and cell death (33, 34). Unlike FASL and TNF-a, Granzyme B induces cell apoptosis via triggering the proteolytic cleavage of Bid (a Bcl-2 family protein), which provokes the release of mitochondrial cytochrome c into the cytosol (35-37). Cytochrome c efflux from mitochondria results in the activation of caspase 9 and 3, leading to apoptosis (38). Granzyme B also can directly activate executioner caspase 3 (39, 40).

CDCA can be blocked by cellular proteins named Inhibitors of Apoptosis (IAP, FIG. 1). The IAP family includes c-IAP1, c-IAP2, XIAP, NIAP, and survivin (41-43). Compared to other agents against CDCA such as Bcl2, IAPs have shown a remarkable ability to block apoptosis induced by a wide spectrum of non-related apoptotic triggers. The significant majority of apoptotic triggers are blocked by at least one IAP with very few exceptions (44). Therefore, IAPs are thought to directly modulate the activities of apoptosis related caspases. All IAPs contain a novel 80 amino acid motif defined as the Baculovirus IAP repeat (BIR) (45). BIR can directly interact with caspase8 and caspase9, thus preventing the proteolytic processing of procaspase-3, procaspase-6, and procaspase-7, consequently interrupting cell apoptosis (43, 46).

SPDCA is a distinct apoptosis pathway reported recently. Even though the study of SPDCA has just started in recent years, its significance in cell transformation and virus infection processes is becoming more and more apparent (47). In 2003, Thorburn et al. found if you infected prostate tumor cells with an adenovirus recombinant that expresses a Fas-associated death domain protein (FADD), the apoptosis induced by FADD was unable to be completely blocked by the pan-caspase inhibitor Z-VAD. However, the FADD induced apoptosis was completely blocked by combining use of Z-VAD and serine protease inhibitor AEBSF (4-2-amino-ethyl-benzenesulfonyl fluoride)(27). This suggests that there exists another apoptotic pathway that is dependent on serine protease, but not on caspases. SPDCA also can be induced by treatment with brefeldin A (BFA) or tunicamycin, combined with cycloheximide (CHX), which prevents the induction of an ER stress response from the toxic overload of misfolded proteins. Egger et al. found that the apoptosis induced by BFA/CHX was unable to be blocked by the pan-caspase inhibitor Z-VAD; however, the BFA/CHX induced apoptosis was blocked by serine protease inhibitor pefabloc (28). The proteases triggering SPDCA are still under investigation. BFA/CHX and cytokine, FASL and TNF-a might trigger SPDCA mean that cellular serine protease(s) involves in SPDCA. Interestingly, SPDCA can also be induced by extra-cellular serine protease. For example, serine protease Granzyme A, a cytokine in the cytotoxic granules of natural killer (NK) cells and cytotoxic T lymphocytes (CTL), is able to directly induce SPDCA (37, 48). Granzyme A is especially important to the challenge of virus infection. Granzyme A deficient mice were compromised in their ability to contain the mousepox virus ectromelia and herpes simplex neuronal infections even though the CTL mediated CDCA was intact (14, 16). This suggests that SPDCA plays an important role in virus clearance.

Proteases

Proteases (also known as proteinases or peptidases) are proteolytic enzymes that catalyze the cleavage of peptide bonds in other proteins. The effect of such cleavage on protein molecules is diverse. In some instances, proteolytic cleavage causes the cleaved protein to become inactive. In other instances, proteolytic cleavage causes a once inactive protein to become activate. In yet other instances, proteolytic cleavage is a mechanism whereby a single polypeptide precursor is cleaved into two or more individual polypeptides.

Proteases, such as, for example, the serine proteases, have been linked to apoptosis (programmed cell death), and are believed to be involved in the development and progression of numerous diseases and disorders, including Alzheimer's and Parkinson's diseases, AIDS and cancer.

Proteases serve to degrade invading organisms, antigen-antibody complexes and certain tissue proteins that are no longer necessary or useful to the organism. In a normally functioning organism, proteases are produced in a limited quantity and are regulated in part through the synthesis of protease inhibitors. A large number of naturally occurring protease inhibitors serve to control the endogenous proteases by limiting their reactions locally and temporally. In addition, the protease inhibitors may inhibit proteases introduced into the body by infective agents. Tissues that are particularly prone to proteolytic attack and infection, e.g., those of the respiratory tract, are rich in protease inhibitors. Protease inhibitors have also become popular as a new class of anti-HIV drugs.

The serine protease inhibitor regulating SPDCA is also unknown. Two kinds of serine protease inhibitors (SPI) have been found in the cell. They are serine protease inhibitor Kazak (SPIK) and serine protease inhibitor Kuntz (SPINT) such as SPINT 2 & 3 (1, 2, 49). These serine protease inhibi-tors inhibit the activity of serine protease, for example, trypsin and chymotrypsin; however, their roles in the SPDCA were unclear.

SPIK is a small protein derived from a gene with 240 base pairs (1). SPIK was first discovered in the pancreas as an inhibitor of autoactivation of trypsinogen (2). SPIK can be secreted from pancreatic cells, as well as from hepatoma cells after transfection [See Figure BBB]. Interestingly, SPIK binds Granzyme A, a SPDCA inducer, suggesting that it probably involves in the regulation of SPDCA (13). Our evidences demonstrates that over-expression of SPIK results in the cell resistant to SPDCA; therefore, SPIK is a SPDCA inhibitor.

In normal human cells, the expression of apoptosis inhibitors, either IAPs or SPIs, is limited. This means that the apoptosis inhibitor genes are inactivated under normal conditions. However, their expression increases dramatically in tumors and tumor cell lines. For example, XIAP and survivin were found to be over-expressed in myeloid leukemias, gastric carcinoma and breast cancers (20, 50-53). Alternatively, SPIK was increased in pancreatic, gastric, and colorectal cancers, as well as HCC and hepatoma cell lines HepG2 and Huh7 (4-7). Since huge biological diversity exists between these different forms of cancer, it is not difficult to understand that the up regulated apoptosis inhibitors differ in the various cancers.

Interestingly, in HCC the increased apoptosis inhibitor is SPIK, not other apoptosis inhibitors such as XIAP and survivin, which has been often considered as the IAPs strongly triggering the cancer (4, 5). By comparison of HCC and normal adjacent liver tissue from same patient, Omachi found that SPIK was dramatically up-regulated in cancer tissue (4). Our recent data also suggest that compared to normal human liver cells SPIK expression was thousands-fold higher in the hepatoma cell lines, especially in the HBV expressing hepatoma cell line HepG2.2.15 and HCV replicon cells (5). In contrast, the other apoptosis inhibitors including XIAP and survivin in these cells either remained unchanged or insignificantly increased (see Figure CCC). The alone distinct increase of SPIK in the HCC and HBV/HCV expressing cells demonstrates that the mechanism of progression of HBV/HCV related HCC differs from other cancers. It may be more dependent on the serine protease dependent cell apoptosis (SPDCA), not caspase dependent cell apoptosis (CDCA). This is supported by the findings that the clearance of virus-infected cells is more dependent on the SPDCA, but not CDCA, as we mentioned before (14-16). The finding of a dramatic increase of SPIK in HCC and HBV/HCV expressing cells is also consistent with our hypothesis that chronic infections of HBV/HCV induce the over expression of SPIK that suppresses the SPDCA, resulting in the infected cell escape of body immune surveillance, and eventually leading to the development of HCC.

SPIK Gene Products

The present invention further contemplates use of the SPIK gene sequence to produce SPIK gene products. SPIK gene products may include proteins that represent functionally equivalent gene products. Such an equivalent gene product may contain deletions, additions or substitutions of amino acid residues within the amino acid sequence encoded by the gene sequences described herein, but which result in a silent change, thus producing a functionally equivalent SPIK gene product. Amino acid substitutions may be made on the basis of similarity in polarity, charge, solubility, hydrophobicity, hydrophilicity, and/or the amphipathic nature of the residues involved.

For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. "Functionally equivalent", as utilized herein, refers to a protein capable of exhibiting a substantially similar in vivo activity as the endogenous gene products encoded by the SPIK gene sequences. Alternatively, when utilized as part of an assay, "functionally equivalent" may refer to peptides capable of interacting with other cellular or extracellular molecules in a manner substantially similar to the way in which the corresponding portion of the endogenous gene product would.

Other protein products useful according to the methods of the invention are peptides derived from or based on the SPIK gene produced by recombinant or synthetic means (derived peptides). SPIK gene products may be produced by recombinant DNA technology using techniques well known in the art. Thus, methods for preparing the gene polypeptides and peptides of the invention by expressing nucleic acid encoding gene sequences are described herein. Methods that are well known to those skilled in the art can be used to construct expression vectors containing gene protein coding sequences and appropriate transcriptional/translational control signals. These methods include, for example, in vitro recombinant DNA techniques, synthetic techniques and in vivo recombination/genetic recombination (57-58). Alternatively, RNA capable of encoding gene protein sequences may be chemically synthesized using, for example, automated synthesizers (59).

A variety of host-expression vector systems may be utilized to express the gene coding sequences of the invention. Such host-expression systems represent vehicles by which the coding sequences of interest may be produced and subsequently purified, but also represent cells that may, when transformed or transfected with the appropriate nucleotide coding sequences, exhibit the gene protein of the invention in situ. These include but are not limited to microorganisms such as bacteria (e.g., *E. coli, B. subtilis*) transformed with recombinant bacteriophage DNA, plasmid DNA or cosmid DNA expression vectors containing gene protein coding sequences; yeast (e.g. *Saccharomyces, Pichia*) transformed with recombinant yeast expression vectors containing the gene protein coding sequences; insect cell systems infected with recombinant virus expression vectors (e.g., baculovirus) containing the gene protein coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing gene protein coding sequences; or mammalian cell systems (e.g. COS, CHO, BHK, 293, 3T3) harboring recombinant expression constructs containing promoters derived from the genome of mammalian cells (e.g., metallothionine promoter) or from mammalian viruses (e.g., the adenovirus late promoter; the vaccinia virus 7.5 K promoter).

In bacterial systems, a number of expression vectors may be advantageously selected depending upon the use intended for the gene protein being expressed. For example, when a large quantity of such a protein is to be produced, for the generation of antibodies or to screen peptide libraries, for example, vectors that direct the expression of high levels of fusion protein products that are readily purified may be desirable. Such vectors include, but are not limited to, the *E. coli* expression vector pUR278, in which the gene protein coding sequence may be ligated individually into the vector in frame with the lac Z coding region so that a fusion protein is produced; pIN vectors and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned SPIK gene protein can be released from the GST moiety.

In a preferred embodiment, full length cDNA sequences are appended with in-frame Bam HI sites at the amino terminus and Eco RI sites at the carboxyl terminus using standard PCR methodologies (Innis, et al. (eds) PCR Protocols: A Guide to Methods and Applications, Academic Press, San Diego (1990)) and ligated into the pGEX-2TK vector (Pharmacia, Uppsala, Sweden). The resulting cDNA construct contains a kinase recognition site at the amino terminus for radioactive labeling and glutathione S-transferase sequences at the carboxyl terminus for affinity purification.

In an insect system, *Autographa californica* nuclear polyhedrosis virus (AcNPV) is used as a vector to express foreign genes. The virus grows in *Spodoptera frugiperda* cells. The gene coding sequence may be cloned individually into non-essential regions (for example the polyhedrin gene) of the virus and placed under control of an AcNPV promoter (for example the polyhedrin promoter). Successful insertion of gene coding sequence will result in inactivation of the polyhedrin gene and production of non-occluded recombinant virus (i.e., virus lacking the proteinaceous coat coded for by the polyhedrin gene). These recombinant viruses are then used to infect *Spocloptera frugiperda* cells in which the inserted gene is expressed (see U.S. Pat. No. 4,745,051).

In mammalian host cells, a number of viral-based expression systems may be utilized. In cases where an adenovirus is used as an expression vector, the gene coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing gene protein in infected hosts. Specific initiation signals may also be required for efficient translation of inserted gene coding sequences. These signals include the ATG initiation codon and adjacent sequences. In cases where an entire gene, including its own initiation codon and adjacent sequences, is inserted into the appropriate expression vector, no additional translational control signals may be needed. However, in cases where only a portion of the gene coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc.

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, W138, etc.

For long-term, high-yield production of recombinant proteins, stable expression is preferred. For example, cell lines that stably express the gene protein may be engineered. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells that stably integrate the plasmid into their chromosomes and grow, to form foci, which in turn can be cloned and expanded into cell lines. This method may advantageously be used to engineer cell lines that express the gene protein. Such engineered cell lines may be particularly useful in screening and evaluation of compounds that affect the endogenous activity of the gene protein.

In a preferred embodiment, timing and/or quantity of expression of the recombinant protein can be controlled using an inducible expression construct. Inducible constructs and systems for inducible expression of recombinant proteins will be well known to those skilled in the art. Examples of such inducible promoters or other gene regulatory elements include, but are not limited to, tetracycline, metallothionine, ecdysone, and other steroid-responsive promoters, rapamycin responsive promoters, and the like. Additional control elements that can be used include promoters requiring specific transcription factors such as viral, particularly HIV, promoters. In one in embodiment, a Tet inducible gene expression system is utilized. Tet Expression Systems are based on two regulatory elements derived from the tetracycline-resistance operon of the *E. coli* Tn10 transposon—the tetracycline repressor protein (TetR) and the tetracycline operator sequence (tetO) to which TetR binds. Using such a system, expression of the recombinant protein is placed under the control of the tetO operator sequence and transfected or transformed into a host cell. In the presence of TetR, which is co-transfected into the host cell, expression of the recombinant protein is repressed due to binding of the TetR protein to the tetO regulatory element. High-level, regulated gene expression can then be induced in response to varying concentrations of tetracycline (Tc) or Tc derivatives such as doxycycline (Dox), which compete with tetO elements for binding to TetR. Constructs and materials for tet inducible gene expression are available commercially from CLONTECH Laboratories, Inc., Palo Alto, Calif.

When used as a component in an assay system, the gene protein may be labeled, either directly or indirectly, to facilitate detection of a complex formed between the gene protein and a test substance. Any of a variety of suitable labeling systems may be used including but not limited to radioisotopes; enzyme labeling systems that generate a detectable calorimetric signal or light when exposed to substrate; and fluorescent labels. Where recombinant DNA technology is used to produce the gene protein for such assay systems, it may be advantageous to engineer fusion proteins that can facilitate labeling, immobilization and/or detection.

Indirect labeling involves the use of a protein, such as a labeled antibody, which specifically binds to the gene product. Such antibodies include but are not limited to polyclonal, monoclonal, chimeric, single chain, Fab fragments and fragments produced by a Fab expression library.

Production of Antibodies

Described herein are methods for the production of antibodies capable of specifically recognizing one or more epitopes. Such antibodies may include, but are not limited to polyclonal antibodies, monoclonal antibodies (mAbs), humanized or chimeric antibodies, single chain antibodies, Fab fragments, F(ab').sub.2 fragments, fragments produced by a Fab expression library, anti-idiotypic (anti-Id) antibodies, and epitope-binding fragments of any of the above. Such antibodies may be used, for example, in the detection of a SPIK gene in a biological sample, or, alternatively, as a method for the inhibition of abnormal SPIK gene activity. Thus, such antibodies may be utilized as part of disease treatment methods, and/or may be used as part of diagnostic techniques whereby patients may be tested for abnormal levels of SPIK gene proteins, or for the presence of abnormal forms of such proteins, see U.S. Pat. No. 5,530,101 (Queen et al.).

For the production of antibodies, various host animals may be immunized by injection with the SPIK gene, its expression product or a portion thereof. Such host animals may include but are not limited to rabbits, mice, rats, goats and chickens, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Polyclonal antibodies are heterogeneous populations of antibody molecules derived from the sera of animals immunized with an antigen, such as SPIK gene product, or an antigenic functional derivative thereof. For the production of polyclonal antibodies, host animals such as those described above, may be immunized by injection with gene product supplemented with adjuvants as also described above.

Monoclonal antibodies, which are homogeneous populations of antibodies to a particular antigen, may be obtained by any technique that provides for the production of antibody molecules by continuous cell lines in culture see U.S. Pat. No. 4,376,110, the human B-cell hybridoma technique, and the EBV-hybridoma technique. Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies U.S. Pat. No. 4,946,778 can be adapted to produce gene-single chain antibodies. Single chain antibodies are typically formed by linking the heavy and light chain fragments of the Fv region via an amino acid bridge, resulting in a single chain polypeptide.

Antibody fragments that recognize specific epitopes may be generated by known techniques. For example, such fragments include but are not limited to: the F(ab').sub.2 fragments that can be produced by pepsin digestion of the antibody molecule and the Fab fragments that can be generated by reducing the disulfide bridges of the F(ab').sub.2 fragments. Alternatively, Fab expression libraries may be constructed to allow rapid and easy identification of monoclonal Fab fragments with the desired specificity.

Screening Methods

The present invention may be employed in a process for screening for agents such as agonists, i.e. agents that bind to and activate SPIK polypeptides, or antagonists, i.e. inhibit the activity or interaction of SPIK polypeptides with its ligand. Thus, polypeptides of the invention may also be used to assess the binding of small molecule substrates and ligands in, for example, cells, cell-free preparations, chemical libraries, and natural product mixtures as known in the art. Any methods routinely used to identify and screen for agents that can modulate receptors may be used in accordance with the present invention.

The present invention provides methods for identifying and screening for agents that modulate SPIK expression or function. More particularly, cells that contain and express SPIK gene sequences may be used to screen for therapeutic agents. Such cells may include non-recombinant monocyte cell lines, such as U937 (ATCC# CRL-1593), THP-1 (ATCC# TIB-202), and P388D1 (ATCC# TIB-63); endothelial cells such as HUVEC's and bovine aortic endothelial cells (BAEC's); as well as generic mammalian cell lines such as HeLa cells and COS cells, e.g., COS-7 (ATCC# CRL-1651). Further, such cells may include recombinant, transgenic cell lines. For example, the transgenic mice of the invention may be used to generate cell lines, containing one or more cell types involved in a disease, that can be used as cell culture models for that disorder. While cells, tissues, and primary cultures derived from the disease transgenic animals of the invention may be utilized, the generation of continuous cell lines is preferred. SPIK gene sequences may be introduced into, and overexpressed in, the genome of the cell of interest. In order to overexpress a SPIK gene sequence, the coding portion of the SPIK gene sequence may be ligated to a regulatory sequence that is capable of driving gene expression in the cell type of interest. Such regulatory regions will be well known to those of skill in the art, and may be utilized in the absence of undue experimentation. SPIK gene sequences may also be disrupted or underexpressed. Cells having SPIK gene disruptions or underexpressed SPIK gene sequences may be used, for example, to screen for agents capable of affecting alternative pathways that compensate for any loss of function attributable to the disruption or underexpression.

In vitro systems may be designed to identify compounds capable of binding the SPIK gene products. Such compounds may include, but are not limited to, peptides made of D- and/or L-configuration amino acids (in, for example, the form of random peptide libraries; (60), phosphopeptides (in, for example, the form of random or partially degenerate, directed phosphopeptide libraries; (61), antibodies, and small organic or inorganic molecules. Compounds identified may be useful, for example, in modulating the activity of SPIK gene proteins, preferably mutant SPIK gene proteins; elaborating the biological function of the SPIK gene protein; or screening for compounds that disrupt normal SPIK gene interactions or themselves disrupt such interactions.

The principle of the assays used to identify compounds that bind to the SPIK gene protein involves preparing a reaction mixture of the SPIK gene protein and the test compound under conditions and for a time sufficient to allow the two components to interact and bind, thus forming a complex that can be removed and/or detected in the reaction mixture. These assays can be conducted in a variety of ways. For example, one method to conduct such an assay would involve anchoring the SPIK gene protein or the test substance onto a solid phase and detecting target protein/test substance complexes anchored on the solid phase at the end of the reaction. In one embodiment of such a method, the SPIK gene protein may be anchored onto a solid surface, and the test compound, which is not anchored, may be labeled, either directly or indirectly.

In practice, microtitre plates are conveniently utilized. The anchored component may be immobilized by non-covalent or covalent attachments. Non-covalent attachment may be accomplished simply by coating the solid surface with a solution of the protein and drying. Alternatively, an immobilized antibody, preferably a monoclonal antibody, specific for the protein may be used to anchor the protein to the solid surface. The surfaces may be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for SPIK gene product or the test compound to anchor any complexes formed in solution, and a labeled antibody specific for the other component of the possible complex to detect anchored complexes.

Compounds that are shown to bind to a particular SPIK gene product through one of the methods described above can be further tested for their ability to elicit a biochemical response from the SPIK gene protein. Agonists, antagonists and/or inhibitors of the expression product can be identified utilizing assays well known in the art.

Antisense, Ribozymes, and Antibodies

Other agents that may be used as therapeutics include the SPIK gene, its expression product(s) and functional fragments thereof. Additionally, agents that reduce or inhibit mutant SPIK gene activity may be used to ameliorate disease symptoms. Such agents include antisense, ribozyme, and triple helix molecules. Techniques for the production and use of such molecules are well known to those of skill in the art.

Anti-sense RNA and DNA molecules act to directly block the translation of mRNA by hybridizing to targeted mRNA and preventing protein translation. With respect to antisense DNA, oligodeoxyribonucleotides derived from the translation initiation site, e.g., between the −10 and +10 regions of the SPIK gene nucleotide sequence of interest, are preferred.

Ribozymes are enzymatic RNA molecules capable of catalyzing the specific cleavage of RNA. The mechanism of ribozyme action involves sequence-specific hybridization of the ribozyme molecule to complementary target RNA, followed by an endonucleolytic cleavage. The composition of ribozyme molecules must include one or more sequences complementary to the SPIK gene mRNA, and must include the well known catalytic sequence responsible for mRNA cleavage. For this sequence, see U.S. Pat. No. 5,093,246, which is incorporated by reference herein in its entirety. As such within the scope of the invention are engineered hammerhead motif ribozyme molecules that specifically and efficiently catalyze endonucleolytic cleavage of RNA sequences encoding SPIK gene proteins.

Specific ribozyme cleavage sites within any potential RNA target are initially identified by scanning the molecule of interest for ribozyme cleavage sites that include the following sequences, GUA, GUU and GUC. Once identified, short RNA sequences of between 15 and 20 ribonucleotides corresponding to the region of the SPIK gene containing the cleavage site may be evaluated for predicted structural features, such as secondary structure, that may render the oligonucleotide sequence unsuitable. The suitability of candidate sequences may also be evaluated by testing their accessibility to hybridization with complementary oligonucleotides, using ribonuclease protection assays.

Nucleic acid molecules to be used in triple helix formation for the inhibition of transcription should be single stranded and composed of deoxyribonucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'-3',3'-5' manner, such that they base pair with first one strand of a duplex and then the other, eliminating the necessity for a sizeable stretch of either purines or pyrimidines to be present on one strand of a duplex.

It is possible that the antisense, ribozyme, and/or triple helix molecules described herein may reduce or inhibit the transcription (triple helix) and/or translation (antisense, ribozyme) of mRNA produced by both normal and mutant SPIK gene alleles. In order to ensure that substantially normal levels of SPIK gene activity are maintained, nucleic acid molecules that encode and express SPIK gene polypeptides exhibiting normal activity may be introduced into cells that do not contain sequences susceptible to whatever antisense, ribozyme, or triple helix treatments are being utilized. Alternatively, it may be preferable to coadminister normal SPIK gene protein into the cell or tissue in order to maintain the requisite level of cellular or tissue SPIK gene activity.

Anti-sense RNA and DNA, ribozyme, and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various well-known modifications to the DNA molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2'O-methyl rather than phosphodiesterase linkages within the oligodeoxyribonucleotide backbone.

Antibodies that are both specific for SPIK gene protein, and in particular, mutant gene protein, and interfere with its activity may be used to inhibit mutant SPIK gene function. Such antibodies may be generated against the proteins themselves or against peptides corresponding to portions of the proteins using standard techniques known in the art and as also described herein. Such antibodies include but are not limited to polyclonal, monoclonal, Fab fragments, single chain antibodies, chimeric antibodies, etc.

In instances where the SPIK gene protein is intracellular and whole antibodies are used, internalizing antibodies may be preferred. However, lipofectin liposomes may be used to deliver the antibody or a fragment of the Fab region that binds to the SPIK gene epitope into cells. Where fragments of the antibody are used, the smallest inhibitory fragment that binds to the target or expanded target protein's binding domain is preferred. For example, peptides having an amino acid sequence corresponding to the domain of the variable region of the antibody that binds to the SPIK gene protein may be used. Such peptides may be synthesized chemically or produced via recombinant DNA technology using methods well known in the art (62-63). Alternatively, single chain neutralizing antibodies that bind to intracellular SPIK gene epitopes may also be administered. Such single chain antibodies may be administered, for example, by expressing nucleotide sequences encoding single-chain antibodies within the target cell population by utilizing, for example, techniques such as those described in (64).

RNA sequences encoding SPIK gene protein may be directly administered to a patient exhibiting disease symptoms, at a concentration sufficient to produce a level of SPIK gene protein such that disease symptoms are ameliorated. Patients may be treated by gene replacement therapy. One or more copies of a normal SPIK gene, or a portion of the gene that directs the production of a normal SPIK gene protein with SPIK gene function, may be inserted into cells using vectors that include, but are not limited to adenovirus, adeno-associated virus, and retrovirus vectors, in addition to other particles that introduce DNA into cells, such as liposomes. Additionally, techniques such as those described above may be utilized for the introduction of normal SPIK gene sequences into human cells.

Cells, preferably, autologous cells, containing normal SPIK gene expressing gene sequences may then be introduced or reintroduced into the patient at positions that allow for the amelioration of disease symptoms.

Pharmaceutical Compositions, Effective Dosages, and Routes of Administration

The identified compounds can be administered to a patient at therapeutically effective doses to treat or ameliorate a disease or condition. A therapeutically effective dose refers to that amount of the compound sufficient to result in amelioration of symptoms of the disease.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

Pharmaceutical compositions for use in accordance with the present invention may be formulated in conventional manner using one or more physiologically acceptable carriers or excipients. Thus, the compounds and their physiologically acceptable salts and solvates may be formulated for administration by inhalation or insufflation (either through the mouth or the nose) or oral, buccal, parenteral, topical, subcutaneous, intraperitoneal, intraveneous, intrapleural, intraoccular, intraarterial, or rectal administration. It is also contemplated that pharmaceutical compositions may be administered with other products that potentiate the activity of the compound and optionally, may include other therapeutic ingredients.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides. Oral ingestion is possibly the easiest method of taking any medication. Such a route of administration, is generally simple and straightforward and is frequently the least inconvenient or unpleasant route of administration from the patient's point of view. However, this involves passing the material through the stomach, which is a hostile environment for many materials, including proteins and other biologically active compositions. As the acidic, hydrolytic and proteolytic environment of the stomach has evolved efficiently to digest proteinaceous materials into amino acids and oligopeptides for subsequent anabolism, it is hardly surprising that very little or any of a wide variety of biologically active proteinaceous material, if simply taken orally, would survive its passage through the stomach to be taken up by the body in the small intestine. The result, is that many proteinaceous medicaments must be taken in through another method, such as parenterally, often by subcutaneous, intramuscular or intravenous injection.

Pharmaceutical compositions may also include various buffers (e.g., Tris, acetate, phosphate), solubilizers (e.g., Tween, Polysorbate), carriers such as human serum albumin, preservatives (thimerosol, benzyl alcohol) and anti-oxidants such as ascorbic acid in order to stabilize pharmaceutical activity. The stabilizing agent may be a detergent, such as tween-20, tween-80, NP-40 or Triton X-100. EBP may also be incorporated into particulate preparations of polymeric compounds for controlled delivery to a patient over an extended period of time. A more extensive survey of components in pharmaceutical compositions is found in Remington's Pharmaceutical Sciences, 18th ed., A. R. Gennaro, ed., Mack Publishing, Easton, Pa. (1990).

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration.

The identified compounds can be administered to a patient at therapeutically effective doses to treat or ameliorate a disease or condition. Non-limiting examples of genetic disorders that can be diagnosed and treated using this method and compounds include hereditary diseases such as cystic fibrosis, Tay-Sachs disease, Lesch-Nyhan Syndrome, sickle cell anemia, hemophelia, atherosclerosis, diabetes, and obesity. Such hereditary diseases may include degenerative and non-degenerative neurological diseases such as Alzheimer's disease, Parkinson's disease, amyotrophic lateral sclerosis, Huntington's disease, Wilson's disease, spinal cerebellar ataxia, Friedreich's ataxia and other ataxias, prion diseases including Creutzfeldt-Jakob disease, dentatorubral pallidoluysian atrophy, spongiform encephalopathies, myotonic dystrophy, depression, schizophrenia, and epilepsy. Hereditary diseases may also include metabolic diseases such as, for example, hypoglycemia or phenylketonuria. Cardiovascular diseases and conditions are also included, non-limiting examples of which include atherosclerosis, myocardial infarction, and high blood pressure. The invention can further be used for detection and diagnosis of Lyme disease, tuberculosis, and sexually transmitted diseases.

The identified compounds are further useful for diagnosis and treatment of disorders of clinical interest. Non-limiting examples of target disorders of clinical interest include asthma, arthritis, psoriasis, excema, allergies, drug resistance, drug toxicity, and cancers such as, but not limited to, human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g. acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myclona, Waldenstrom's macroglobulinemia, and heavy chain disease.

The identified compounds are further useful for diagnosis and treatment of patients with autoimmune diseases, including but not limited to, insulin dependent diabetes mellitus, multiple sclerosis, systemic lupus erythematosus, Sjogren's syndrome, scleroderma, polymyositis, chronic active hepatitis, mixed connective tissue disease, primary biliary cirrhosis, pernicious anemia, autoimmune thyroiditis, idiopathic Addison's disease, vitiligo, gluten-sensitive enteropathy, Graves' disease, myasthenia gravis, autoimmune neutropenia, idiopathic thrombocytopenia purpura, rheumatoid arthritis, cirrhosis, pemphigus vulgaris, autoimmune infertility, Goodpasture's disease, bullous pemphigoid, discoid lupus, ulcerative colitis, and dense deposit disease.

It is appreciated that the methods described herein will be useful in diagnosing and treating diseases of other mammals, for example, farm animals including cattle, horses, sheep, goat, and pigs, household pets including cats and dogs, and plants including agriculturally important plants and garden plants.

Diagnostics

A variety of methods may be employed to diagnose disease conditions associated with the SPIK gene. Specifically, reagents may be used, for example, for the detection of the presence of SPIK gene mutations, or the detection of either over or under expression of SPIK gene mRNA.

According to the diagnostic and prognostic method of the present invention, alteration of the wild-type SPIK gene locus is detected. In addition, the method can be performed by detecting the wild-type SPIK gene locus and confirming the lack of a predisposition or neoplasia. "Alteration of a wild-type gene" encompasses all forms of mutations including deletions, insertions and point mutations in the coding and noncoding regions. Deletions may be of the entire gene or only a portion of the gene. Point mutations may result in stop codons, frameshift mutations or amino acid substitutions. Somatic mutations are those that occur only in certain tissues, e.g., in tumor tissue, and are not inherited in the germline. Germline mutations can be found in any of a body's tissues and are inherited. If only a single allele is somatically mutated, an early neoplastic state may be indicated. However, if both alleles are mutated, then a late neoplastic state may be indicated. The finding of gene mutations thus provides both diagnostic and prognostic information. A SPIK gene allele that is not deleted (e.g., that found on the sister chromosome to a chromosome carrying a SPIK gene deletion) can be screened for other mutations, such as insertions, small deletions, and point mutations. Mutations found in tumor tissues may be linked to decreased expression of the SPIK gene product. However, mutations leading to non-functional gene products may also be linked to a cancerous state. Point mutational events may occur in regulatory regions, such as in the promoter of the gene, leading to loss or diminution of expression of the mRNA. Point mutations may also abolish proper RNA processing, leading to loss of expression of the SPIK gene product, or a decrease in mRNA stability or translation efficiency.

One test available for detecting mutations in a candidate locus is to directly compare genomic target sequences from cancer patients with those from a control population. Alternatively, one could sequence messenger RNA after amplification, e.g., by PCR, thereby eliminating the necessity of determining the exon structure of the candidate gene. Mutations from cancer patients falling outside the coding region of the SPIK gene can be detected by examining the non-coding regions, such as introns and regulatory sequences near or within the SPIK gene. An early indication that mutations in noncoding regions are important may come from Northern blot experiments that reveal messenger RNA molecules of abnormal size or abundance in cancer patients as compared to control individuals.

The methods described herein may be performed, for example, by utilizing pre-packaged diagnostic kits comprising at least one specific gene nucleic acid or anti-gene antibody reagent described herein, which may be conveniently used, e.g., in clinical settings, to diagnose patients exhibiting disease symptoms or at risk for developing disease.

Any cell type or tissue, preferably platelets, neutrophils or lymphocytes, in which the gene is expressed may be utilized in the diagnostics described below.

DNA or RNA from the cell type or tissue to be analyzed may easily be isolated using procedures that are well known to those in the art. Diagnostic procedures may also be performed in situ directly upon tissue sections (fixed and/or frozen) of patient tissue obtained from biopsies or resections, such that no nucleic acid purification is necessary. Nucleic acid reagents may be used as probes and/or primers for such in situ procedures (see, for example, (65)).

Gene nucleotide sequences, either RNA or DNA, may, for example, be used in hybridization or amplification assays of biological samples to detect disease-related gene structures and expression. Such assays may include, but are not limited to, Southern or Northern analyses, restriction fragment length polymorphism assays, single stranded conformational polymorphism analyses, in situ hybridization assays, and polymerase chain reaction analyses. Such analyses may reveal both quantitative aspects of the expression pattern of the gene, and qualitative aspects of the gene expression and/or gene composition. That is, such aspects may include, for example, point mutations, insertions, deletions, chromosomal rearrangements, and/or activation or inactivation of gene expression.

Preferred diagnostic methods for the detection of gene-specific nucleic acid molecules may involve for example, contacting and incubating nucleic acids, derived from the cell type or tissue being analyzed, with one or more labeled nucleic acid reagents under conditions favorable for the specific annealing of these reagents to their complementary sequences within the nucleic acid molecule of interest. Preferably, the lengths of these nucleic acid reagents are at least 9 to 30 nucleotides. After incubation, all non-annealed nucleic acids are removed from the nucleic acid:fingerprint molecule hybrid. The presence of nucleic acids from the fingerprint tissue that have hybridized, if any such molecules exist, is then detected. Using such a detection scheme, the nucleic acid from the tissue or cell type of interest may be immobilized, for example, to a solid support such as a membrane, or a plastic surface such as that on a microtitre plate or polystyrene beads. In this case, after incubation, non-annealed, labeled nucleic acid reagents are easily removed. Detection of the remaining, annealed, labeled nucleic acid reagents is accomplished using standard techniques well-known to those in the art.

Alternative diagnostic methods for the detection of gene-specific nucleic acid molecules may involve their amplification, e.g., by PCR (the experimental embodiment set forth in Mullis U.S. Pat. No. 4,683,202, ligase chain reaction (66), self sustained sequence replication (67), transcriptional amplification system (68) or any other nucleic acid amplification method, followed by the detection of the amplified molecules using techniques well known to those of skill in the art. These detection schemes are especially useful for the detection of nucleic acid molecules if such molecules are present in very low numbers.

In one embodiment of such a detection scheme, a cDNA molecule is obtained from an RNA molecule of interest (e.g., by reverse transcription of the RNA molecule into cDNA). Cell types or tissues from which such RNA may be isolated include any tissue in which wild type fingerprint gene is known to be expressed, including, but not limited, to platelets, neutrophils and lymphocytes. A sequence within the cDNA is then used as the template for a nucleic acid amplification reaction, such as a PCR amplification reaction, or the like. The nucleic acid reagents used as synthesis initiation reagents (e.g., primers) in the reverse transcription and nucleic acid amplification steps of this method may be chosen from among the gene nucleic acid reagents described herein. The preferred lengths of such nucleic acid reagents are at least 15-30 nucleotides. For detection of the amplified product, the nucleic acid amplification may be performed using radioactively or non-radioactively labeled nucleotides. Alternatively, enough amplified product may be made such that the product may be visualized by standard ethidium bromide staining or by utilizing any other suitable nucleic acid staining method.

Antibodies directed against wild type or mutant gene peptides may also be used as disease diagnostics and prognostics. Such diagnostic methods, may be used to detect abnormalities in the level of gene protein expression, or abnormalities in the structure and/or tissue, cellular, or subcellular location of fingerprint gene protein. Structural differences may include, for example, differences in the size, electronegativity, or antigenicity of the mutant fingerprint gene protein relative to the normal fingerprint gene protein.

Protein from the tissue or cell type to be analyzed may easily be detected or isolated using techniques that are well known to those of skill in the art, including but not limited to western blot analysis. For a detailed explanation of methods for carrying out western blot analysis, (69). The protein detection and isolation methods employed herein may also be such as those described in Harlow and Lane, for example, (70).

Preferred diagnostic methods for the detection of wild type or mutant gene peptide molecules may involve, for example, immunoassays wherein fingerprint gene peptides are detected by their interaction with an anti-fingerprint gene-specific peptide antibody.

For example, antibodies, or fragments of antibodies useful in the present invention may be used to quantitatively or qualitatively detect the presence of wild type or mutant gene peptides. This can be accomplished, for example, by immunofluorescence techniques employing a fluorescently labeled antibody (see below) coupled with light microscopic, flow cytometric, or fluorimetric detection. Such techniques are especially preferred if the fingerprint gene peptides are expressed on the cell surface.

The antibodies (or fragments thereof) useful in the present invention may, additionally, be employed histologically, as in immunofluorescence or immunoelectron microscopy, for in situ detection of fingerprint gene peptides. In situ detection may be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the fingerprint gene peptides, but also their distribution in the examined tissue. Using the present invention, those of ordinary skill will readily perceive that any of a wide variety of histological methods (such as staining procedures) can be modified in order to achieve such in situ detection.

Immunoassays for wild type, mutant, or expanded fingerprint gene peptides typically comprise incubating a biological sample, such as a biological fluid, a tissue extract, freshly harvested cells, or cells that have been incubated in tissue culture, in the presence of a detectably labeled antibody capable of identifying fingerprint gene peptides, and detecting the bound antibody by any of a number of techniques well known in the art.

The biological sample may be brought in contact with and immobilized onto a solid phase support or carrier such as nitrocellulose, or other solid support that is capable of immobilizing cells, cell particles or soluble proteins. The support may then be washed with suitable buffers followed by treatment with the detectably labeled gene-specific antibody. The solid phase support may then be washed with the buffer a second time to remove unbound antibody. The amount of bound label on solid support may then be detected by conventional means.

The terms "solid phase support or carrier" are intended to encompass any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of anti-wild type or -mutant fingerprint gene peptide antibody may be determined according to well known methods. Those skilled in the art will be able to determine operative and optimal assay conditions for each determination by employing routine experimentation.

One of the ways in which the gene peptide-specific antibody can be detectably labeled is by linking the same to an enzyme and using it in an enzyme immunoassay (EIA) (71-75). The enzyme that is bound to the antibody will react with an appropriate substrate, preferably a chromogenic substrate, in such a manner as to produce a chemical moiety that can be detected, for example, by spectrophotometric, fluorimetric or by visual means. Enzymes that can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by calorimetric methods that employ a cluomogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect fingerprint gene wild type, mutant, or expanded peptides through the use of a radioimmunoassay (RIA) (see, e.g., Weintraub, B., Principles of Radioimmunoassays, Seventh Training Course on Radioligand Assay Techniques, The Endocrine Society, March, 1986). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals. These metals can be attached to the antibody using such metal chelating groups as diethylenetriaminepentacetic acid (DTPA) or ethylenediamine-tetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction, Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Throughout this application, various publications, patents and published patent applications are referred to by an identifying citation. The disclosures of these publications, patents and published patent specifications referenced in this application are hereby incorporated by reference into the present disclosure to more fully describe the state of the art to which this invention pertains.

Screening for SPIK-Inhibiting Agents

Utilizing SPIK polynucleotides and polypeptides as well as the substrates described above, the present invention provides methods of screening for novel modulators of SPIK. Various biochemical and molecular biological techniques or assays well known in the art can be employed to practice the present invention. Such techniques are described in, e.g., (76-77).

Several screen schemes can be employed to screen for novel modulators of SPIK. In some embodiments, test agents are first screened for binding to SPIK. Agents thus identified are further tested for ability to modulate protease activity of the enzyme. In some other embodiments, test agents are directly screened for ability to alter proteolysis activity of a substrate serine protease by SPIK. In these methods, test agents are first screened for ability to bind to SPIK and/or ability to inhibit serine protease activity of the target enzyme. Agents that have been identified to inhibit SPIK inhibition of serine protease activity are then further examined for ability to inhibit carcinogenesis.

Test Agents

Test agents that can be screened with methods of the present invention include polypeptides, beta-turn mimetics, polysaccharides, phospholipids, hormones, prostaglandins, steroids, aromatic compounds, heterocyclic compounds, benzodiazepines, oligomeric N-substituted glycines, oligocarbamates, polypeptides, saccharides, fatty acids, steroids, purines, pyrimidines, derivatives, small molecules, siNA, siRNA, dsRNA, dsDNA, anti-senseDNA, nucleic acids, antibodies, polyclonal antibodies, monoclonal antibodies, structural analogs or combinations thereof. Some test agents are synthetic molecules, and others natural molecules.

Test agents are obtained from a wide variety of sources including libraries of synthetic or natural compounds. Combinatorial libraries can be produced for many types of compound that can be synthesized in a step-by-step fashion. Examples of peptide libraries have been described in, (78-80) Large combinatorial libraries, of compounds can be constructed by the encoded synthetic libraries (ESL) method described in WO 95/12608, WO 93/06121, WO 94/08051, WO 95/35503 and WO 95/30642. Peptide libraries can also be generated by phage display methods (see, e.g., Devlin, WO 91/18980). Libraries of natural compounds in the form of bacterial, fungal, plant and animal extracts can be obtained from commercial sources or collected in the field. Known pharmacological agents can be subject to directed or random chemical modifications, such as acylation, alkylation, esterification, amidification to produce structural analogs.

Combinatorial libraries of peptides or other compounds can be fully randomized, with no sequence preferences or constants at any position. Alternatively, the library can be biased, i.e., some positions within the sequence are either held constant, or are selected from a limited number of possibilities. For example, in some cases, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, or to purines.

The test agents can be natural occurring proteins or their fragments. Such test agents can be obtained from a natural source, e.g., a cell or tissue lysate. Libraries of polypeptide agents can also be prepared, e.g., from a cDNA library commercially available or generated with routine methods. The test agents can also be peptides, e.g., peptides of from about 5 to about 30 amino acids, with from about 5 to about 20 amino acids being preferred, and from about 7 to about 15 being particularly preferred. The peptides can be digests of naturally occurring proteins, random peptides, or "biased" random peptides. In some methods, the test agents are polypeptides or proteins.

The test agents can also be nucleic acids. Nucleic acid test agents can be naturally occurring nucleic acids, random nucleic acids, or "biased" random nucleic acids. For example, digests of prokaryotic or eukaryotic genomes can be similarly used as described above for proteins.

In some preferred methods, the test agents are small molecules (e.g., molecules with a molecular weight of not more than about 1,000). Preferably, high throughput assays are adapted and used to screen for such small molecules. In some methods, combinatorial libraries of small molecule test agents as described above can be readily employed to screen for small molecule modulators of SPIK. A number of assays are available for such screening, (81-84).

Libraries of test agents to be screened with the claimed methods can also be generated based on structural studies of SPIK or its fragments. Such structural studies allow the identification of test agents that are more likely to bind to SPIK. The three-dimensional structure of SPIK or its fragments (e.g., its catalytic domain) can be studied in a number of ways, e.g., crystal structure and molecular modeling. Methods of studying protein structures using x-ray crystallography are well known in the literature. See Physical Bio-chemistry, (85-86). Computer modeling of a target protein (e.g., SPIK) provides another means for designing test agents for screening modulators of the target protein. Methods of molecular modeling have been described in the literature, e.g., U.S. Pat. No. 5,612,894 entitled "System and method for molecular modeling utilizing a sensitivity factor", and U.S. Pat. No. 5,583,973 entitled "Molecular modeling method and system". In addition, protein structures can also be determined by neutron diffraction and nuclear magnetic resonance (NMR)(87-88).

Modulators of the present invention also include antibodies that specifically bind to SPIK. Such antibodies can be monoclonal or polyclonal. Such antibodies can be generated using methods well known in the art. For example, the production of non-human monoclonal antibodies, e.g., murine or rat, can be accomplished by, for example, immunizing the animal with SPIK or its fragment (89). Such an immunogen can be obtained from a natural source, by peptides synthesis or by recombinant expression.

Humanized forms of mouse antibodies can be generated by linking the CDR regions of non-human antibodies to human constant regions by recombinant DNA techniques. e(90) and WO 90/07861. Human antibodies can be obtained using phage-display methods. See, e.g., Dower et al., WO 91/17271; McCafferty et al., WO 92/01047. In these methods, libraries of phage are produced in which members display different antibodies on their outer surfaces, Antibodies are usually displayed as Fv or Fab fragments. Phage displaying antibodies with a desired specificity are selected by affinity enrichment to SPIK.

Human antibodies against SPIK can also be produced from non-human transgenic mammals having transgenes encoding at least a segment of the human immunoglobulin locus and an inactivated endogenous immunoglobulin locus. See, e.g., Lonberg et al., WO93/12227 (1993); Kucherlapati, WO 91/10741 (1991). Human antibodies can be selected by competitive binding experiments, or otherwise, to have the same epitope specificity as a particular mouse antibody. Such antibodies are particularly likely to share the useful functional properties of the mouse antibodies. Human polyclonal antibodies can also be provided in the form of serum from humans immunized with an immunogenic agent. Optionally, such polyclonal antibodies can be concentrated by affinity purification using SPIK or its fragment.

Screening for Agents that Bind to SPIK

In some methods, test agents are first screened for ability to bind to SPIK. Typically, purified SPIK, an enzymatic fragment, or an appropriate variant or analog is used in high-throughput screens to assay test agents for the ability to bind to the protease. Binding of test agents to SPIK can be assayed by a number of methods including e.g., labeled in vitro protein-protein binding assays, electrophoretic mobility shift assays, immunoassays for protein binding, functional assays (phosphorylation assays, etc.), and the like. See, e.g., U.S. Pat. Nos. 4,366,241; 4,376,110; 4,517,288; and 4,837,168; (91-93). Agents that bind to SPIK can be identified by detecting a direct binding to SPIK, e.g., co-immunoprecipitation with SPIK by an antibody directed to SPIK. They can also be identified by detecting a signal that indicates that the agent binds to SPIK, e.g., fluorescence quenching or FRET.

Competition assays provide a suitable format for identifying test agents that specifically bind to SPIK. In such formats, test agents are screened in competition with a compound already known to bind to SPIK. The known binding compound can be a synthetic compound. It can also be an antibody that specifically recognizes SPIK, e.g., a monoclonal antibody directed against SPIK. If the test agent inhibits binding of the compound known to bind SPIK, then the test agent is also likely to bind SPIK.

Numerous types of competitive binding assays are known, for example: solid phase direct or indirect radioimmunoassay (RIA), solid phase direct or indirect enzyme immunoassay (EIA), sandwich competition assay; solid phase direct biotin-avidin EIA; solid phase direct labeled assay, solid phase direct labeled sandwich assay (see); solid phase direct label RIA using sup.125I label; solid phase direct biotin-avidin EIA; and direct labeled RIA (94-99). Typically, such an assay involves the use of purified polypeptide bound to a solid surface or cells bearing either of these, an unlabelled test agent and a labeled reference compound. Competitive inhibition is measured by determining the amount of label bound to the solid surface or cells in the presence of the test agent. Usually the test agent is present in excess. Modulating agents identified by competition assay include agents binding to the same epitope as the reference compound and agents binding to an adjacent epitope sufficiently proximal to the epitope bound by the reference compound for steric hindrance to occur. Usually, when a competing agent is present in excess, it will inhibit specific binding of a reference compound to a common target polypeptide by at least 50 or 75%.

The screening assays can be either in insoluble or soluble formats. One example of the insoluble assays is to immobilize SPIK or its fragment onto a solid phase matrix. The solid phase matrix is then put in contact with test agents, for an interval sufficient to allow the test agents to bind. After washing away any unbound material from the solid phase matrix, the presence of the agent bound to the solid phase allows identification of the agent. The methods can further include the step of eluting the bound agent from the solid phase matrix, thereby isolating the agent. Alternatively, other than immobilizing SPIK, the test agents are bound to the solid matrix and SPIK molecule is then added.

Soluble assays include some of the combinatory libraries screening methods described above. Under the soluble assay formats, neither the test agents nor SPIK are bound to a solid support. Binding of SPIK or fragment thereof to a test agent can be determined by, e.g., changes in fluorescence of either SPIK or the test agents, or both. Fluorescence may be intrinsic or conferred by labeling either component with a fluorophor.

In some binding assays, either SPIK, the test agent, or a third molecule (e.g., an antibody against SPIK) can be provided as labeled entities, i.e., covalently attached or linked to a detectable label or group, or cross-linkable group, to facilitate identification, detection and quantification of the polypeptide in a given situation. These detectable groups can comprise a detectable polypeptide group, e.g., an assayable enzyme or antibody epitope. Alternatively, the detectable group can be selected from a variety of other detectable groups or labels, such as radiolabels or a chemiluminescent or fluorescent group.

Binding of a test agent to SPIK provides an indication that the agent could be a modulator of the enzyme. A test agent that binds to SPIK can be further examined to determine its activity on the protease activity of the enzyme. The existence, nature, and extent of such activity can be tested by an activity assay as detailed below. Such an activity assay can confirm that the test agent binding to SPIK indeed has a modulatory activity on SPIK. More often, as detailed below, such activity assays can be used independently to identify test agents that modulate activities of SPIK (i.e., without first assaying their ability to bind to SPIK).

Screening for Agents that Modulate SPIK Inhibition of Serine Protease Activity

In some methods, test agents are directly screened for ability to modulate the inhibition of serine proteolysis of a substrate by SPIK action upon a serine protease. In some embodiments, the substrate is a synthetic peptide. Various assays can be employed to monitor effects of test agents on the inhibition of serine proteolysis of a substrate by SPIK action upon a serine protease. Preferably, test agents are screened with a high-through screening format. Test agents that modulate protease inhibition activity of SPIK can be identified with both cell-based or cell-free assay systems. Cell-based systems can be native, i.e., cells that normally express the protease, e.g., endothelial cells. Cell-based assays may involve recombinant host cells expressing the protease protein.

More often, cell-free systems are employed to screen for agents that alter (e.g., inhibit) the inhibitory activity of SPIK. Typically, the assay system contains SPIK or an SPIK fragment as described above, a labeled or un-labeled substrate, a serine protease, as well as other reagents necessary for the enzymatic reaction (as exemplified in the Examples below). The enzyme is contacted with test agents prior to or concurrently with incubation with the substrate. Effect of the test agents on the protease activity is monitored by comparing digestion of the substrate in the reaction to that of a control reaction in which no test agent is present.

Methods for monitoring serine protease activity are well known in the art, e.g., as described in Sambrook et al. and Ausubel et al., supra. For example, proteolysis of *Bacillus anthracis* protective antigen can be assayed as described (100-101). Specific methods are also disclosed in the art and in the present invention. In some methods, non-labeled substrates can be used. Inhibition of proteolysis of a bacterial toxin by a serine protease in the presence of SPIK can be monitored by electrophoresis followed by visualization of the reaction products. In some methods, proteolysis of an un-labeled substrate is monitored by zymography following SDS polyacrylamide gel electrophoresis (102).

In other methods, a labeled substrate is used. Labeled substrates suitable for the screening include, e.g., substrates that are radio-labeled; fluorometric; or calorimetric (103-106). Effect of a test agent on digestion of the labeled substrate (e.g., a bacterial toxin) by the enzyme can be monitored by a number of means. In some preferred embodiments, the substrate is fluorescently labeled, and fluorescence signal due to the proteolysis is typically detected continuously, at multiple time points in the course of the enzymatic reaction, or at a single time point at or near the end of the reaction. By continually monitoring the fluorescence for each test agent, kinetic data can also optionally be obtained. For example, proteolysis of a fluorescently labeled substrate can be assayed as described in the Examples below. Briefly, a peptide substrate is labeled with the fluorophore 7-amino-4-carbamoyl-methylcoumarin (acc). Protease activity of the purified serine protease in the presence of SPIK polypeptide on the substrate can be monitored by quantifying accumulation of the fluorescent signal due to the cleavage of the substrate.

In some other methods, fluorescent resonance energy transfer (FRET)-based methods (107) can be employed in screening for agents that modulate SPIK protease inhibitory activity. In some embodiments, FRET is used to detect cleavage of a labeled substrate. FRET is a distance dependent excited state interaction in which emission of one fluorophore is coupled to the excitation of another fluorophore which is in proximity, e.g., close enough for an observable change in emissions to occur. Typically, a FRET pair (a donor and an acceptor) are attached to the substrate on the two sides of the cleavage site. Once the substrate is cleaved, the donor and acceptor are no longer held in close proximity and the acceptor no longer quenches the donor signal. As a result, the donor then emits a signal that is observed by a detector. The detection can be monitored continuously or at multiple time points.

The following examples are intended only to illustrate the present invention and should in no way be construed as limiting the subject invention.

EXAMPLES

Example 1

High throughput screen system. SPIK will be made through recombinant technology and purified by HPLC. The fluorescence substrate for trypsin, a casein derivative that is heavily labeled with the pH-insensitive, red-fluorescent BODIPY® TR-X dye (excitation/emission ~589/617 nm), is brought from Invitrogen (Carlsbad Calif.) and solved in the reaction buffer for use. The high-throughput screen is carried out in 96-well formats. The procedure is as:

1. 10 μl tested compounds are added to the 96 well plate, each well containing one compound, at the concentration started with 0.5 μM.
2. 40 μl recombinant SPIK and trypsin mixture are added to the wells, at the ratio that just completely inhibits the trypsin activity (pre-determined). Plate is incubated at 37 C, room temperature for 30 minutes. The 3 wells without compound serve as negative controls and 3 wells without compound and SPIK serve as positive controls for trypsin activity.
3. 100 μL1 reaction buffer containing the fluorescence substrates for trypsin digestion is added in the plate, and plate then is incubated at 370 C, room temperature 30-60 minutes in dark.
4. Measure the fluorescence with a fluorescence Microplate-reader equipped with appropriate filters.
5. The capability of compounds to inhibit SPIK is quantified by the activation of trypsin digestion or leased fluorescence. Higher fluorescence means higher activity of compound to inhibit SPIK.

Example 2

SPIK is a SPDCA inhibitor. The first evidence to suggest SPIK is an apoptosis inhibitor is from transfection of SPIK into HeLa cells. The reason for using HeLa cells for transfection is that SPIK expression in this cell line is constitutively at undetectable levels and hence creates no ambient background [FIG. 1A, lane 3].

HeLa cells were seeded into a 6 well plate at a density of $1 \times 10^5$, and then transfected with the plasmid P3 that contains the entire SPIK gene under the control of HCMV promoter. After 3 days, the transfected cells were split into two daughter 6 well plates. Cells were then cultured another 3 days. SPIK RNA in one of two daughter plates was examined by Northern blot. At the same time cell apoptotic death was induced in a control plate by treatment of cultured cells with BFA/CHX (5 mg/ml/10 mg/ml). Although Egger et al. reported BFA/CHX generally induces SPDCA, in order to ensure that CDCA is blocked, 100 mM Z-AVD was added. Z-VAD is a pan-caspase inhibitor, presentation of Z-VAD at 100 mM, all the caspases involved in CDCA including of the key caspases: 3, 7 and 8 are inhibited (28). Therefore, at this condition it is possible to study the role of SPIK in SPDCA.

The expression of SPIK was examined by Northern Blot. Briefly; ten micrograms of total RNA isolated from transfected cells was resolved in 1% agarose gel, and then transferred to a Nylon membrane. This was followed by hybridization with a SPIK specific probe derived from the SPIK gene. The result shows that the transfection of plasmid P3 resulted in substantial expression of SPIK RNA in HeLa cells [FIG. 1A, lane 2]. This SPIK expression can be silenced using RNAi technology (54). Co-transfection of siRNA L183 with P3 reduced the amount of SPIK RNA expression by more than 70% compared with cells transfected with P3 alone [FIG. 1A, lane 1 & 2]. The suppression of SPIK by L183 was specific. The expression of green fluorescent protein (GFP) in HeLa cells was not affected by co-transfection of L183 (Unpublished observation). The reduction of SPIK RNA was also not due to the unequal loading. Ethidium Bromide (EB) staining of ribosome RNA indicated the equivalence of the samples loaded [FIG. 1A, bottom panel].

Notably, the cells transfected with P3 appeared more resistant to the BFA/CHX/Z-VAD induced cell apoptosis. After a one-day treatment, around 25% of cells expressing SPIK progressed to apoptosis, characterized by cell shrinkage, membrane blebbing, growth arrestment and detachment from culture plate [FIG. 1B, P3, up panel]. In contrast, more than 70% of control cells transfected with P3 vector were found to be apoptotic [FIG. 1B, Vector, up panel]. Considering the transfection efficiency was around 60% in our experiment (determined by expression of GFP, unpublished data), cells expressing SPIK thus were generally resistant to apoptotic death. Once the SPIK expression has been suppressed via co-transfection with siRNA L183, apoptotic cell levels clearly increased nearly up to the control level [FIG. 1B, P3 & L187, up panel].

Figure 2:
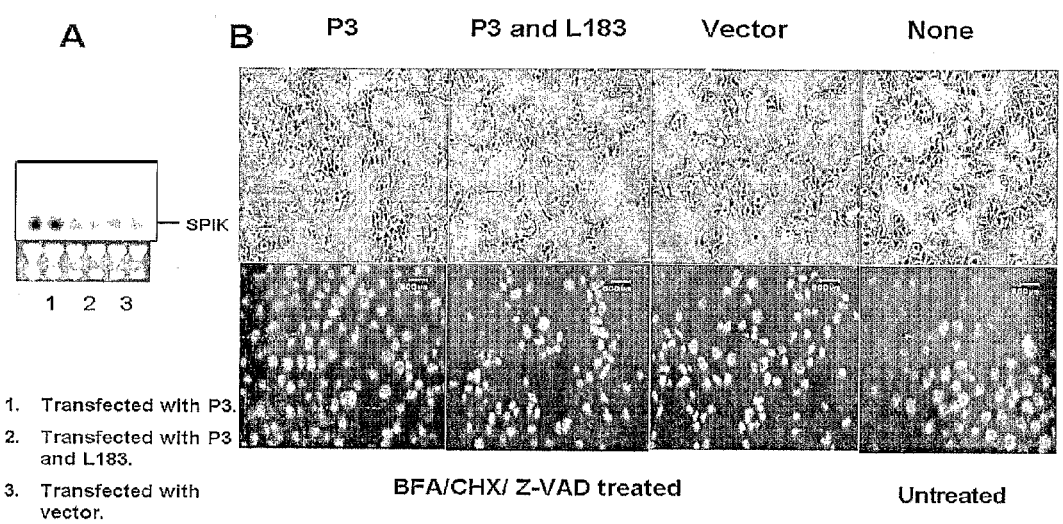
FIG. 2A-2B. Expression of SPIK suppressing SPDCA in hepatoma cell line Huh7T. Huh7T cells were seeded in 6 well plates at a density of $1 \times 10^5$, until 80% confluency was reached. Cells were transfected with 2 µg P3 containing entire SPIK gene under the control of HCMV promoter or vector. For silencing analysis, 1 µg siRNA L183 with U6 promoter was co-transfected with P3. After 3 days, cells were split into two daughter plates by trypsin digestion, and then cultured another 3 days for Northern Blot or SPDCA analysis respectively.

The resistance of SPIK expressing cells to apoptosis was confirmed by Hoechst staining, another method used to examine cell apoptosis. The results show that the bright blue staining of condensed nucleus that often occurs in the cells undergoing apoptosis did not appear in the cells transfected with P3, while strong apoptotic nuclear condensation appeared in the cells transfected with the vector [FIG. 2B, Hoechst stain, arrows, bottom panel]. As expected, in the case where SPIK expression was suppressed by co-transfection with L183, the number of detected apoptotic cells increased considerably, almost returning to the level of control cells [FIG. 1B, Hoechst stain, bottom panel]. Altogether, these results demonstrate that SPIK expression suppresses cell apoptosis i.e. SPIK is an inhibitor of SPDCA.

Figure 3:
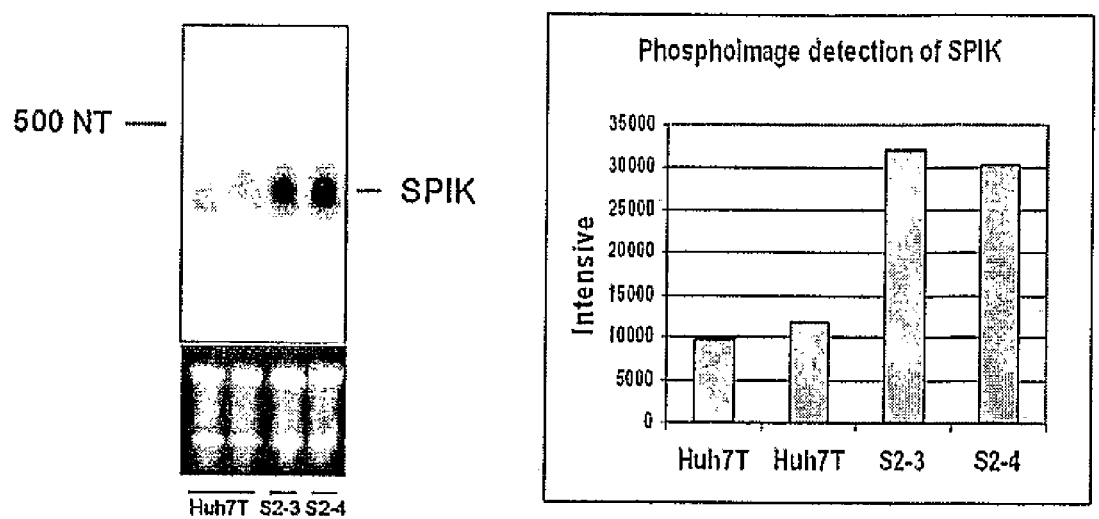
FIG. 3. higher expression of SPIK in the stable cell lines S2-3 and S2-4 via insertion of SPIK gene into chromosome DNA of Huh7T cells. Huh7T cell was transfected with the plasmid containing SPIK gene with selection marker Neo gene. After 3 days, cells were treated with 1 mg/ml G418. The survived cells were reseeded and colonized. Cell clones were picked up, and continually cultured and amplified in G418 medium about 2 months. The SPIK expression in those colony cells was then analyzed by Northern Blot with probe specified for SPIK and quantified by Phosphateimage.

The same results were attained from transfection Huh7 cell. Huh7 cells are originally derived from HCC, thus it is more suitable to our study. Huh7 T cells were seeded at a density of $1 \times 10^5$, in 60 mm dish. Cells were transfected with P3 and L187 as before. After 3 days transfection, cells was split in to two daughter dishes as described before, and then apoptosis was induced in one of dish, and the cells in another dish were collected for Northern blot analysis. Since Huh7T cell is a HCC derived cell line, compared with normal human liver cell, the SPIK has been over-expressed in this cell line [FIG. 2A lane 3] (5). However, even if SPIK gene was activated in Huh7 cell, transfected with P3 containing SPIK still noticeably increased the SPIK expression, and in contrast, co-transfection of siRNA L187 abrogated this increase [FIG. 2A, lane 1&2]. As observed in HeLa cells, treatment with BFA/CHX/Z-VAD induced the apoptosis represented by cell shrinkage and membrane blebbibg in the cells transfected with P3/L183 or vector; in the other hand, there was few cells was going to apoptosis in the cells transfected with P3 alone [FIG. 3B, phase contrast]. This implies that the resistance to SPDCA also occurs in Huh7 cells over-expressing SPIK. Hoechst stain also shows that Huh7T cells that expresses more SPIK appeared more resistant to apoptotic death, alternatively, the cell co-transfected with L183 or vector were apoptosis sensitive [FIG. 3B, Hoechst].

Altogether these results demonstrate that 1). Over-expressing SPIK can prevent SPDCA; therefore, SPIK is a SPCDA inhibitor. 2). The suppression of apoptosis by SPIK is not cell type dependent.

Example 3

Figure 5:
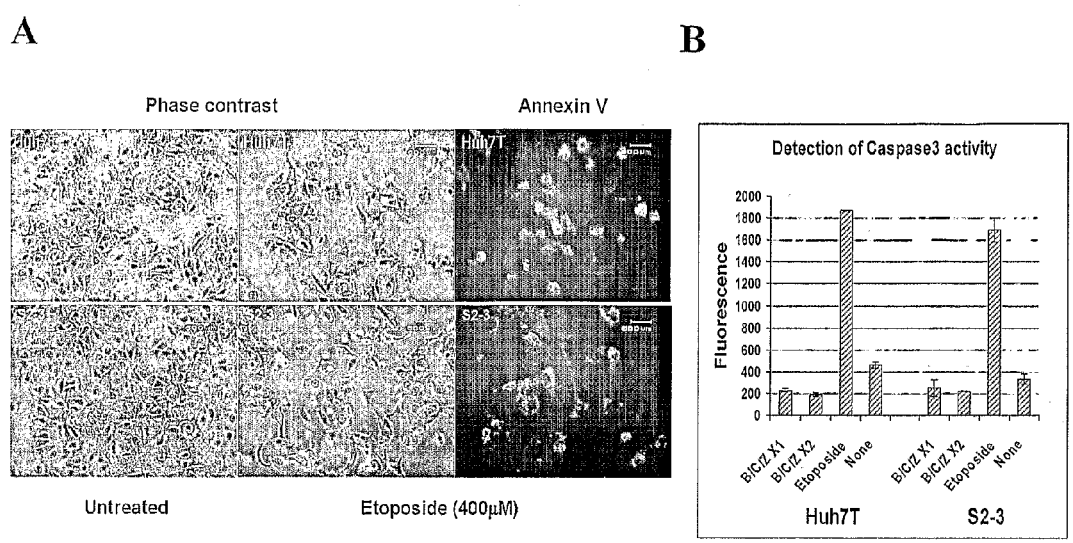
FIG. 5A-5B. SPIK only prevents SPDCA, not CDCA.

Stable cell line over-expressing SPIK is more resistant to SPDCA. A stable cell line producing higher amounts of SPIK was constructed. Huh7T cells were transfected with the plasmid containing the SPIK coding sequence with the selection marker Neo gene. After 3 days, cells were treated with 1 mg/ml G418. Surviving cells were reseeded and colonized. Finally eight G418 resistant cell clones were selected, and continually cultured and amplified in G418 medium about 2 months. The SPIK expression in those colony cells was then analyzed by Northern Blot with probe specified for SPIK. No difference, either in morphology and growth, was found between these clones with its parental Huh7T cell [FIG. 5 untreated]. This suggests that those cells fundamentally are same as parental cell. Two of eight: S2-3 and S2-4 produced very high amount of SPIK were further studied in apoptosis analysis. Compared with parental Huh7T cell, both S2-3 and S2-4 produces 3 fold more SPIK based on Northern Blot quantification with PhosphorImager [FIG. 3]. Since our apoptosis studies indicate that there was no difference between S2-3 and S2-4, therefore, only the data from S2-3 was presented here.

Figure 4:
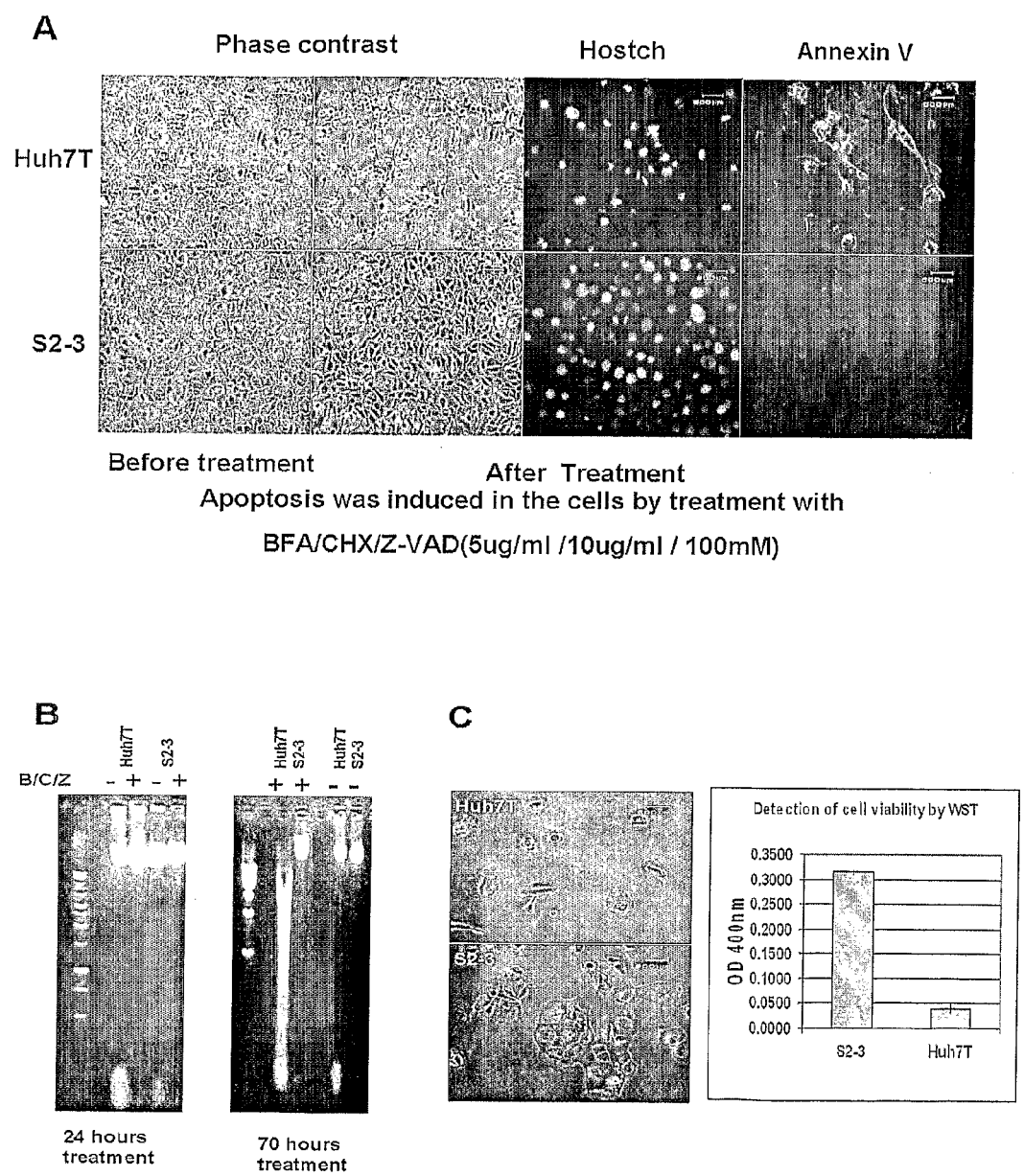
FIG. 4A-4C. The stable cell line S2-3 over-expresses SPIK and is more resistant to SPDCA. SPDCA was induced in S2-3 and its parental Huh7T cell by BFA/CHX and Z-VAD as before. The cell apoptosis in early, middle and late stage were examined by morphological change (contrast phase), annexin stain, Hoechst stain and DNA fragmentation. The apoptosis also was examined by Clonogenic growth study.

To analyze the resistance of S2-3 cell to SPDCA, $10^5$ S2-3 cells and its parental Huh7T cells were seeded in 60 mm dishes. SPDCA were induced by BFA/CHX/Z-VAD as before. The apoptosis in different stages, for example early, middle and late stage, which are represented by cell morphological change/Annexin stain, Hoechst stain and DNA fragmentation respectively, was studied. FIG. 4A shows that after treatment with BFA/CHX/Z-VAD 24 hours, the cell shrinkage, and membrane blebbing were obviously initiated in nearly all Huh7T cells. At the same time, the morphology of S2-3 cells only slight changed or kept unchanged [FIG. 4A, phase contrast]. The initiation of cell apoptosis in Huh7T cells was also indicated by annexin staining. As we mentioned before, annexin is an early apoptosis indictor. In situ stain of apoptosis cell with fluorescence labeled annexin allows identification of cell surface changes that occur early during the apoptotic process. Incubation of cells treated with BFA/CHX/Z-VAD with annexin, the strong fluorescence was only found in Huh7T cell, while very little S2-3 cell was stained [FIG. 4A, annexin]. This suggests that S2-3 is more resistant to BFA/CHX/Z-VAD induced SPDCA. Nuclei condensation often occurs in the middle of apoptosis process, which can be identified by pro-nuclei fluorescent dye Hoechst stain. Nuclei condensation indicated by blight blue fluorescence occurred in the Huh7T cells after longer treatment (28 hours), but not in S2-3 cells [FIG. 4A Hoechst]. No nucleus condensation was in the S2-3 cell further supports that S2-3 is more resistant to SPDCA. Chromosome DNA fragmentation appears at the late stage of apoptosis. In order to analyze DNA fragmentation, total DNA was isolated from S2-3 and Huh7T cells treated with BHA/CHX/Z-VAD in different time. Ten microgram DNA was then resolved in 1.5% agarose gel and stained with Ethidium bromide. Twenty-four hours treatment of BHA/CHX/Z-VAD only induced a slight chromosome DNA fragmentation in Huh7T cells. This was agreement with DNA fragmentation occurring at late stage of apoptosis. As expected, there was not any DNA fragmentation occurring in the S2-3 cell as well as in the untreated cells [FIG. 4B]. However, 70 hours treatment induced clear DNA fragmentation in the Huh7T cell, but not in the S2-3 cells and untreated cells [FIG. 4B]. The resistance of S2-3 cell to apoptosis in different stages implies that SPIK is a SPDCA inhibitor.

Another evidence to support that S2-3 cells are more resistant to apoptotic death is from cell clonogenic study. When cell progresses the apoptotic death, it loses the capacity to divide and grow; therefore, they can not form the growth clone after reseeding. In contrast, the non-apoptotic cells can retain their growth, and then a clone forms. S2-3 cell and Huh7T cell were treated with BFA/CHX/Z-VAD, after 28 hours, the cells were signalized and released by trypsin, and then 100 cells were reseeded in 24-well-plate. After 7 days growth, the clones only appeared from S2-3 cell, in contrast, no clones were formed from Huh7T cells [FIG. 4C]. The cell viability based on a calorimetric assay (WST-1, Roche, USA) shows that after 7 days the amount of S2-3 cells was 10 times more than Huh7T cell [FIG. 4C], despite the initiated cell was same. In fact the treatment of Huh7T cell with BFA/CHX/Z-VAD prevents its growth and proliferation at all.

Because the only difference between S2-3 and Huh7T cell is that S2-3 produces more SPIK, all together these results indicate that SPIK is a SPDCA inhibitor.

Example 4

SPIK did not prevent the CDCA. After demonstration of SPIK expression associates with cell resistance to SPDCA, we are interested whether SPIK also can inhibit CDCA.

$10^5$ S2-3 and Huh7T cells were seeded in 60 mm dishes. When the cell reached 90% confluent, CDCA inducer etoposide was added. After 28-40 hours, the cell shrinkage, blebbing and detachment from culture was found in both cell lines. At the same time, the strong fluorescence stain by annexin was also observed in both cell lines [FIG. 5A]. The amount of apoptotic cells in two cell lines was very similar. Around 62% S2-3 cell was stained by annexin, while 58% of Huh7T cell was stained after 40 hours treatment [data not shown]. This suggests that the apoptosis occurs in these cell lines is at the same level. Etoposide can induce the apoptosis in SPIK expressing cell suggests that SPIK is not a CDCA inhibitor.

Figure 6:
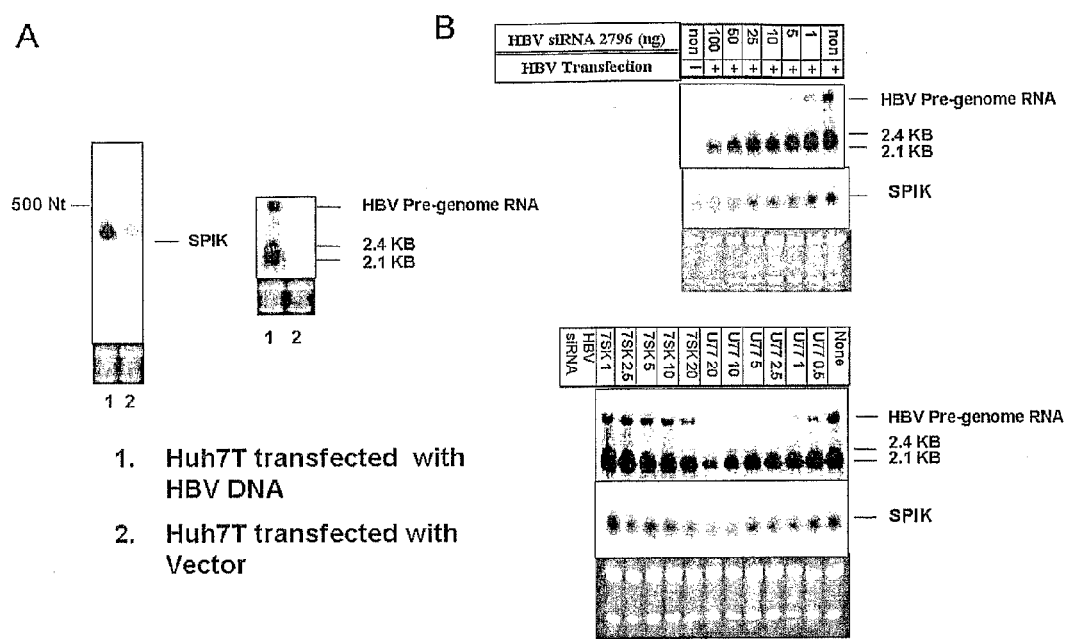
FIG. 6A-6B. Up-regulation of SPIK in the HBV expressing cells. SPIK RNA and HBV RNA in the HBV expressing cells were examined by Northern blot with specific probe for SPIK and HBV.

The same level of apoptosis induced by etoposide in S2-3 cell and Huh7T cell was confirmed by the examination of caspase 3 activity in these cells. After 40 hours treatment, all cells were lysed in 200 ml lysis buffer. 40 ml lysate of each sample was analyzed for caspase 3 activity test using caspase 3 detected kits [Biovision, Mountain View, Calif.]. FIG. 6B shows that despite S2-3 produced 3 folds more SPIK than Huh7T cell [FIG. 3], the increased activity of caspase 3 via etoposide treatment was at the same level in both cells. In contrast, the caspase 3 activity of untreated cells or the pan-caspase inhibitor Z-VAD treated cells kept unchanged [FIG. 5B]. This result implies that SPIK can not suppress caspase3 represented CDCA. Additionally, the activity of caspase3 was not increased in the cells, in which SPDCA was induced by BFA/CHX, even by double doses [FIG. 5B, B/C/ZX2]. This also suggests that the apoptosis induced by BFA/CHX/Z-VAD is SPDCA.

Etoposide can induce same level of CDCA in S2-3 and its parental Huh7T cell is consistent with our observation that there is no fundamental difference between these two cell lines.

Example 5

Hepatitis B and Hepatitis C virus replication activate SPIK expression. Since SPIK is up-regulated in HCC(4), therefore, after we demonstrate SPIK is a SPDCA inhibitor, we are interested in the relationship of it and chronic HBV/HCV infection. HBV or HCV infection usually triggers the chronic liver inflammation (Hepatitis). It is believed that the SPIK is activated by the inflammatory (9). Therefore, HBV or HCV replication and SPIK expression is studied.

Consequently, Huh/7T cells were transfected in vitro with plasmid containing a head-to-head dimer of HBV genome. After 6 days, the RNA was isolated and analyzed by Northern blot with HBV and SPIK specific probes. HBV RNA species, characteristic of HBV replication, including pre-genomic and 2.4/2.1 Kb RNA, were observed in the transfected cells but not in control cells [FIG. 6A, right panel]. Most importantly, hybridization with a SPIK specific probe shows that the SPIK RNA in HBV expressing cells was substantially greater than in the non-expressing cells [FIG. 6A, left panel].

Figure 7:
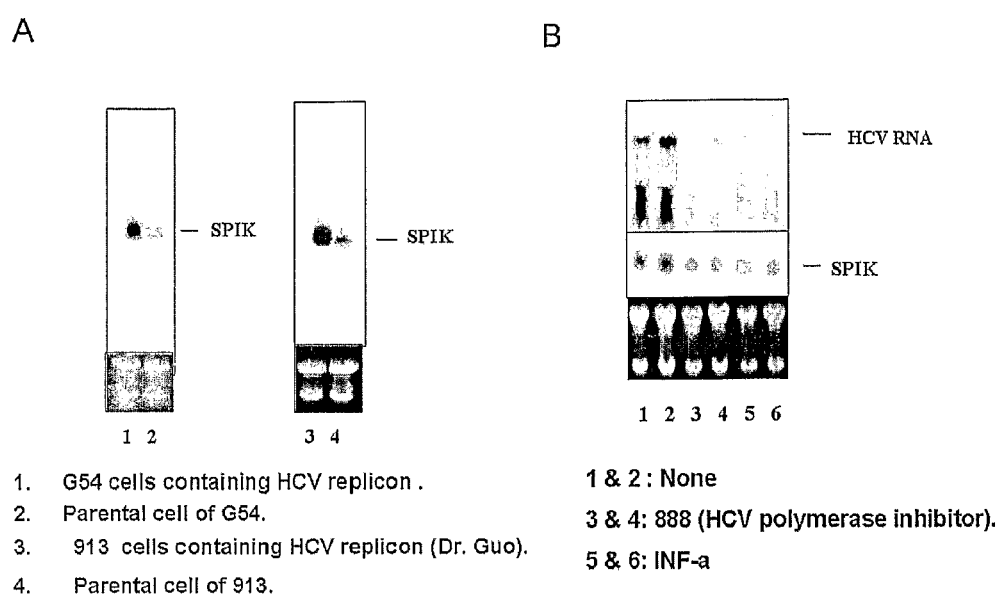
FIG. 7A-7B. SPIK in the HCV expressing cells. SPIK RNA was detected in the cells with/without HCV replicon as before. HCV RNA was defined by the hybridization of membrane with radio-labeled probe specified HCV. The equal loading of the samples was defined by EB stained ribosome RNAs.

The up-regulation of the SPIK level in HBV expressing cells is a consequence of viral replication. This was confirmed by RNAi gene silencing technology. HBV was expressed in the Huh7T cells via transfection; the replication of HBV in transfected cells was controlled by co-transfection of HBV siRNA 2796 at different doses from 1 ng to 100 ng. Six days after transfection, the total RNA was isolated from the cells. The HBV replicational forms such as pre-genomic and 2.4/2.1 Kb RNA and SPIK RNA then were examined by Northern blot with HBV or SPIK specific probes. The co-transfection of HBV siRNA resulted in a dose dependent decrease of HBV RNA [FIG. 6B, upper panel]. More interestingly, SPIK RNA also decreased with HBV RNA proportionally [FIG. 7B, upper panel]. The decrease of SPIK expression was not due to side-silence of HBV siRNA. Using of HBV siRNA U77 and 7SK that target the different HBV sequence gave the same results. When HBV replication forms were down, the SPIK expression was also down proportionally [FIG. 7B, bottom panel]. Ethidium bromide staining of ribosomal RNA suggests the sample's equal loading [FIG. 6B]. All these results imply that HBV replication is closely linked with SPIK expression.

Figure 8:
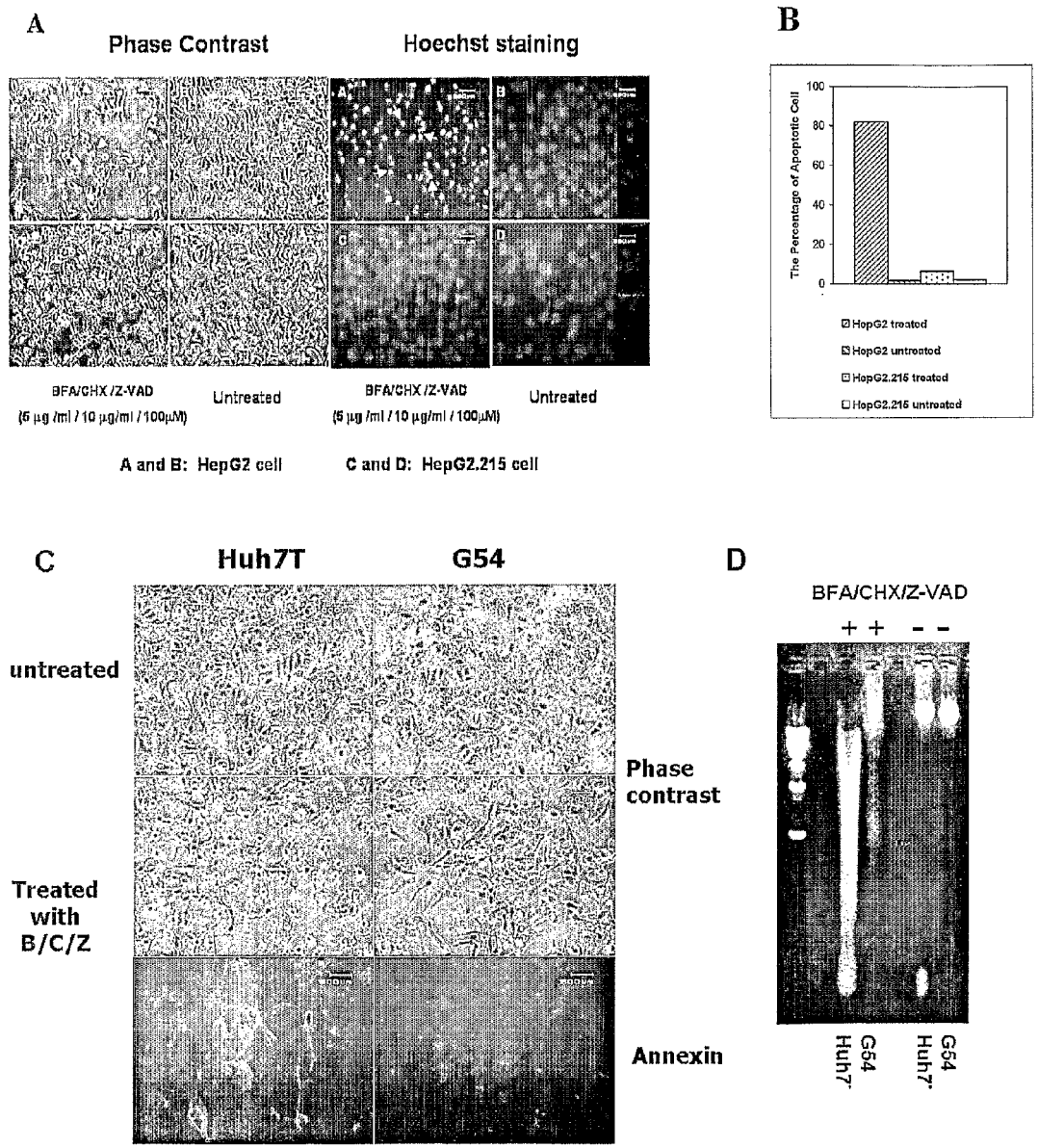
FIGS. 8A-8D. HBV and HCV expressing cells were resistant to SPDCA.

In the HCV study, G54 cell line and its parental cell line were used. G54 is a cell line derived from the Huh7 T, which contains the HCV entire genome as a replicon and constitutively produces HCV. Total RNA was isolated from G54 and Huh7T cells, and then SPIK expression was compared by Northern Blot with a SPIK specific probe as before The results show that the up-regulation of SPIK also occurred in the HCV expressing cells. After hybridization with the SPIK probe, the SPIK RNA in G54 cells was notably greater than in its parent Huh7T cells [FIG. 7A, lane 1 & 2]. Considering the possible differences between HCV replicon cells from different laboratories, cells with or without HCV replicon from another source were examined for SPIK RNA. As shown in FIG. 8A, SPIK RNA levels were also substantially increased in HCV replicon expressing cells 913 provided by Dr. J. Guo [FIG. 8A, lane 3 & 4].

Over-expression of SPIK RNA in G54 cells can be abrogated by inhibition of HCV replication. Treatment of HCV replicon cells with either 2 mM of the HCV polymerase inhibitor 888 for two days or $10^5$ IU/ml interferon-a overnight has reduced HCV replication by approximately 90% [FIG. 7B, lane 3-6]. This is consistent with previous reports of these antiviral agents (55, 56). Interestingly, the suppression of HCV replication also has abrogated the up-regulation of SPIK expression. The SPIK level in G54 cells correspondingly decreased with HCV RNA after treatments of HCV polymerase inhibitor and interferon-a [FIG. 7B, lane 3-6].

Altogether, the results presented strongly support the hypothesis that HBV and HCV replications up-regulate SPIK expression.

Example 6

HBV/HCV expressing cells are more resistant to the SPDCA. The resistance of HBV or HCV expressing cells to SPDCA was examined by inducing SPDCA in the stable cell lines expressing HBV (HepG2.2.15) and HCV (G54), via treatment with BFA/CHX/Z-VAD.

HepG2.2.15 cells expressing HBV and its parent HepG2 cells were seeded in a 6 well plate. To minimize the growth difference between these two cell lines, the plates were coated with collagen. SPDCA was induced by treatment of cultured cells with BFA/CHX/Z-VAD as before (28). After a one-day treatment, HepG2.2.15 cells appeared to be more resistant to SPDCA than HepG2 cells, despite the fact that the cell viability was somehow affected by drug treatment. Less than 10% of the HepG2.2.15 cells were found to be apoptotic [FIGS. 8A, C&D]. In contrast, BFA/CHX/Z-VAD treatment resulted in nearly 80% of the cultured HepG2 displaying progress towards apoptosis [FIGS. 8A, A&B, 8B]. Hoechst staining shows that nucleus condensation was evidently visible in the HepG2 cells after treatment, while only a few were seen in HepG2.2.15 cells at the same condition [FIG. 9A, Hoechst]. Thus, although there are probably many differences between HepG2 and HepG2.2.15 cells other than HBV expression, the difference in sensitivity to apoptosis induction was dramatic.

To study the influence of HCV replication upon SPDCA, G54 and Huh7T cells (its parent cell) were seeded in a 60 mm dish. SPDCA was induced by BFA/CHX/Z-VAD. FIG. 8C shows that most of G54 cells containing HCV replicon did not appear apoptotic morphological change, while more than 90% of the Huh7T cells did [FIG. 8C, phase contrast]. The insensitivity of HCV replicon cell to SPDCA was also seen subsequently by annexin staining. Compared to the parental cells, much fewer HCV expressing cells were stained by annexin after being treated with SPDCA inducers BFA/CHX/Z-VAD [FIG. 8C, Annexin]. DNA fragmentation study also support that the HCV expressing cells were more resistant to apoptosis. 70 hours treatment of BFA/CHX/Z-VAD obviously triggered the DNA fragmentation in Huh7T cell, but not in G54 cells [FIG. 8D]. These data support that over-expression of SPIK in HBV/HCV replication cells results in the cell resistance to SPDCA. In contrast, both HepG2.215 and G54 are sensitive to CDCA induced by etoposide [data not shown].

Example 7

Inhibition of SPIK expression by L71 and L183 siRNAs. SPIK siRNA contain siRNA sequences composed of a sense and an anti-sense strands that are complementary to the different parts of the SPIK gene. The sense and anti-sense fragments are linked by a hairpin linker with nine nucleosides (TTCAAGAGA (SEQ ID NO: 5), FIG. 9A). siRNA sequence is dedicated at the 3' end of the transcript. Our observations and of others suggest that at this position the RNAi effects were maximal (unpublished data). After transcription, the hairpin structure forces the anti-sense fragment linking to the sense fragment to form the siRNA [FIG. 9C]. The inhibition of SPIK expression by both L71 and L183 is shown in FIG. 9D. G54 cells were transfected with SPIK siRNA L71 or L183. After 3 days, total RNA was isolated from half of cells, and the suppressions of L71 and L183 were analyzed by Northern blot. The other half cells were reseeded; the apoptosis was induced by treatment of BFA/CHX/Z-VAD as above. Cell apoptosis was determined by DNA fragmentation.

All together, the evidences presented here support our hypothesis that HBV/HCV replication results in over-expression of apoptosis inhibitor SPIK, consequently, triggering the cell resistance to the apoptotic death. This resistance to apoptosis might lead the infected cell escape from immune surveillance characterized by CTL/NK cell induced apoptotic killing, finally resulting in the development of cancer.

In this study, we have demonstrated that the serine protease inhibitor Kazal (SPIK) is able to inhibit serine protease dependent cell apoptosis (SPDCA), and the infections of two different but with remarkable similarity in their pathogenesis viruses, HBV and HCV, up-regulated SPIK expression, consequently suppressing SPDCA. The significances of these findings are: it is first time to demonstrate SPIK regulating the serine protease related cell apoptotic death. Secondly, these findings have provided the vital evidences that different non-cytopathogenetic viruses such as HBV and HCV infections can prevent SPDCA via the same way of stimulation of its regulator SPIK. Furthermore, because the over-expression of SPIK was found in numerous human cancer cells (4, 5, 6), these findings have given the critical evidences to support the hypothesis that the unlimited growth of the cells, in which the apoptosis has been blocked by SPIK, could finally develop to cancer.

Unlike CDCA rapidly triggering cell death, SPDCA such as apoptosis triggered by Granzyme A rather slowly acts (9). This slow progressing apoptosis is more significant to the development of cancer, particularly to HCC induced by HBV and HCV infections, which often happens after long time chronic infection of the viruses.

How HBV and HCV to activate the SPIK and prevent SPDCA remain unsolved. HBV X protein (HBx) and HCV core protein, NS3 and NS5 definitely are the mostly possible viral proteins that are involved in. Recent studies suggest that HBx, and HCV core protein, NS3 and NS5 play an important role in the CDCA. Unfortunately, the results are controversial. For example, HBx blocked TNF, Fas mediated caspase cascade, suppressing the apoptosis of the target cell (19). HBx protein also abrogated p53-Blc induced apoptosis (20). Additionally, HBx has prevented cell death when expressed in the hepatocyte of mice (21), and HBx has caused over-expression of cyclin D1 and developed breast cancer in transgenic mice (22). Those studies support the anti-apoptosis activity of HBx. In contrast, HBx has been shown to induce mitochondrial aggregation and cytochrome c release, which is indicative of induction of apoptosis through mitochondrial dysfunction (23). HBx also was reported to activate transcription factor NF-kB, sensitizing cell apoptotic death (24).

As with HBx, transfection of HCV core protein can suppress cell apoptosis through up-regulation of inhibitor of caspase-activated DNase (25). In contrast, HCV core protein can induce apoptosis in mature dendritic cells via activation of caspase 8 (26). Expressions of NS3 and NS5 in mature dendritic cells have provoked cell apoptosis (27). However, the Huh7 cells expressing HCV NS3 and NS5 replicon have failed to promote apoptotic cell death (28).

While the invention has been described in detail and with reference to specific examples thereof, it will be apparent to one skilled in the art that various changes and modifications can be made therein without departing from the spirit and scope thereof.

REFERENCES

1. K. Kobayashi, M. Horiuchi, T. Saheki, *Hepatology* 25, 1160 (May, 1997).
2. L. J. Greene, M. H. Pubols, D. C. Bartelt, *Methods Enzymol* 45, 813 (1976).
3. N. Tomita et al., *Cancer* 66, 2144 (Nov. 15, 1990).
4. Y. Ohmachi et al., *Int J Cancer* 55, 728 (Nov. 11, 1993).
5. X. Lu, T. Block, *Int J Med Sci* 1, 21 (2004).
6. M. Higashiyama et al., *Am J Clin Pathol* 93, 8 (January, 1990).
7. M. Higashiyama et al., *Br J Cancer* 62, 954 (December, 1990).
8. A. Murata et al., *Life Sci* 43, 1233 (1988).
9. T. Yasuda et al., *Gene* 131, 275 (Sep. 15, 1993).
10. J. P. Drenth, R. te Morsche, J. B. Jansen, *Gut* 50, 687 (May, 2002).
11. D. Martinvalet, P. Zhu, J. Lieberman, *Immunity* 22, 355 (March, 2005).
12. J. Pardo et al., *J Cell Biol* 167, 457 (Nov. 8, 2004).
13. S. Tsuzuki et al., *Biochem J* 372, 227 (May 15, 2003),
14. R. A. Pereira, M. M. Simon, A. Simmons, *J Virol* 74, 1029 (January, 2000).
15. J. Pardo, S. Balkow, A. Anel, M. M. Simon, *Eur J Immunol* 32, 2881 (October, 2002).
16. A. Mullbacher et al., *PNAS* 93, 5783 (Jun. 11, 1996, 1996).
17. F. H. Igney, P. H. Krammer, *Nature Reviews Cancer* 2, 277 (2002).
18. J. M. Brown, L. D. Attardi, *Nat Rev Cancer* 5, 231 (March, 2005).
19. M. E. Guicciardi, G. J. Gores, *Gut* 54, 1024 (July, 2005).
20. M. Preusser et al., *Am J Clin Pathol* 124, 543 (October, 2005).
21. Q. S. Tong et al., *World J Gastroenterol* 11, 634 (Feb. 7, 2005).
22. T. Endo et al., *Cancer in Immunol Immunother* 53, 770 (September, 2004).
23. T. Nemoto et al., *Exp Mol Pathol* 76, 253 (June, 2004).
24. Y. Kamegaya et al., *Hepatology* 41, 660 (March, 2005).
25. M. Notarbartolo et al., *Ann N Y Acad Sci* 1028, 289 (December, 2004).
26. Y. Ohmachi et al., *J Hepatol* 21, 1012 (December, 1994).
27. J. Thorburn, L. M. Bender, M. J. Morgan, A. Thorburn, *Mol. Biol. Cell* 14, 67 (Jan. 1, 2003, 2003).
28. L. Egger et al., *Cell Death Differ* 10, 1188 (October, 2003).
29. A. Ashkenazi, V. M. Dixit, *Science* 281, 1305 (Aug. 28, 1998).
30. P. Golstein, *Science* 275, 1081 (Feb. 21, 1997).
31. D. R. Green, G. Kroemer, *Science* 305, 626 (2004).
32. I. Budihardjo, H. Oliver, M. Lutter, X. Luo, X. Wang, *Annu Rev Cell Dev Biol* 15, 269 (1999).
33. D. W. Nicholson, N. A. Thornberry, *Trends Biochem Sci* 22, 299 (August, 1997).
34. G. Nunez, M. A. Benedict, Y. Hu, N. Inohara, *Oncogene* 17, 3237 (Dec. 24, 1998).
35. M. Barry et al., *Mol Cell Biol* 20, 3781 (June, 2000).
36. S. Cory, J. M. Adams, *Nat Rev Cancer* 2, 647 (September, 2002).
37. F. Martinon, J. Tschopp, *Cell* 117, 561 (2004).
38. C. Adrain, B. M. Murphy, S. J. Martin, *J Biol Chem* 280, 4663 (Feb. 11, 2005).
39. S. J. Lord, R. V. Rajotte, G. S. Korbutt, R. C. Bleackley, *Immunol Rev* 193, 31 (June, 2003).
40. I. S. Goping et al., Immunity 18, 355 (March, 2003).
41. Q. L. Deveraux et al., *Embo J* 18, 5242 (Oct. 1, 1999).

42. Q. L. Deveraux, J. C. Reed, *Genes Dev* 13, 239 (Feb. 1, 1999).
43. Q. L. Deveraux et al., *Embo J* 17, 2215 (Apr. 15, 1998).
44. E. C. LaCasse, S. Baird, R. G. Korneluk, A. E. MacKenzie, *Oncogene* 17, 3247 (Dec. 24, 1998).
45. P. Liston, W. G. Fong, R. G. Korneluk, *Oncogene* 22, 8568 (Nov. 24, 2003).
46. C. Rocken, S. Carl-McGrath, *Dig Dis* 19, 269 (2001).
47. E. C. de Bruin et al., *Cell Death Differ* 10, 1204 (October, 2003).
48. S. Shresta, T. A. Graubert, D. A. Thomas, S. Z. Raptis, T. J. Ley, *Immunity* 10, 595 (May, 1999).
49. J. P. Salier, *Trends Biochem Sci* 15, 435 (November, 1990).
50. I. Tamm et al., *Clin Cancer Res* 6, 1796 (May, 2000).
51. K. Tanaka et al., *Clin Cancer Res* 6, 127 (January, 2000).
52. I. P. Tomlinson, M. R. Novelli, W. F. Bodmer, *Proc Natl Acad Sci USA* 93, 14800 (Dec. 10, 1996).
53. Q. S. Tong et al., *Cancer Gene Ther* 12, 509 (May, 2005).
54. A. Fire, *Trends Genet.* 15, 358 (September, 1999).
55. B. Gu et al., *Biochemical and Biophysical Research Communications* 313, 343 (2004).
56. J.-T. Guo, V. V. Bichko, C. Seeger, *J. Virol.* 75, 8516 (Sep. 15, 2001, 2001).
57. Sambrook et al., Molecular Cloning: A Laboratory Manual, Cold Spring Harbor Press, N.Y., 3.sup.rd Ed (2000),
58. Ausubel et al., Current Protocols in Molecular Biology, John Wiley & Sons, Inc., New York (1999)
59. Oligonucleotide Synthesis: A Practical Approach, Gait, M. J. ed., IRL Press, Oxford (1984))
60. Lam, et al., Nature, 354:82-4 (1991)
61. Songyang, et al., Cell, 72:767-78 (1993)
62. Creighton, Proteins: Structures and Molecular Principles (1984) W.H. Freeman, New York 1983
63. Sambrook, et al., 1989
64. Marasco, et al., Proc. Natl. Acad. Sci. USA, 90:7889-93 (1993)
65. Nuovo, PCR In Situ Hybridization: Protocols and Applications, Raven Press, N.Y. (1992)
66. Barany, Proc. Natl. Acad. Sci. USA, 88:189-93 (1991)
67. Guatelli, et al., Proc. Natl. Acad. Sci. USA, 87:1874-78 (1990)
68. Kwoh, et al., Proc. Natl. Acad. Sci. USA, 86:1173-77 (1989)
69. Sambrook et al., Molecular Cloning: A Laboratory Manual, Cold Spring Harbor Press, N.Y., 3.sup.rd Ed (2000)
70. Antibodies: A Laboratory Manual, Cold Spring Harbor Laboratory Press, Cold Spring Harbor, N.Y. (1988)
71. Voller, Ric Clin Lab, 8:289-98 (1978) ["The Enzyme Linked Immunosorbent Assay (ELISA)", Diagnostic Horizons 2:1-7, 1978, Microbiological Associates Quarterly Publication, Walkersville, Md.
72. Voller, et al., J. Clin. Pathol., 31:507-20 (1978)
73. Butler, Meth. Enzymol., 73:482-523 (1981)
74. Maggio (ed.), Enzyme Immunoassay, CRC Press, Boca Raton, Fla. (1980)
75. Ishikawa, et al., (eds.) Enzyme Immunoassay, Igaku-Shoin, Tokyo (1981)
76. Sambrook et al., Molecular Cloning: A Laboratory Manual, Cold Spring Harbor Press, N.Y., 3.sup.rd Ed (2000)
77. Ausubel et al., Current Protocols in Molecular Biology, John Wiley & Sons, Inc., New York (1999)
78. Lam et al., Nature 354:82-84, 1991
79. Houghten et al., Nature 354:84-86, 1991
80. Songyang et al., Cell 72:767-778, 1993
81. Schultz (1998) Bioorg Med Chem Lett 8:2409-2414
82. Weller (1997) Mol. Divers. 3:61-70;
83. Fernandes (1998) Curr Opin Chem Biol 2:597-603
84. Sittampalam (1997) Curr Opin Chem Biol 1:384-91
85. Van Holde, K. E. (Prentice-Hall, New Jersey 1971), pp. 221-239
86. Physical Chemistry with Applications to the Life Sciences, D. Eisenberg & D. C. Crothers (Benjamin Cummings, Menlo Park 1979)
87. Physical Chemistry, 4th Ed. Moore, W. J. (Prentice-Hall, New Jersey 1972
88. NMR of Proteins and Nucleic Acids, K. Wuthrich (Wiley-Interscience, New York 1986)
89. Harlow & Lane, Antibodies, A Laboratory Manual, Cold Spring Harbor Laboratory Press, Cold Spring Harbor N.Y.
90. Queen et al., Proc. Natl. Acad. Sci. USA 86, 10029-10033 (1989)
91. Bevan et al., Trends in Biotechnology 13:115-122, 1995
92. Ecker et al., Bio/Technology 13:351-360, 1995
93. Hodgson, Bio/Technology 10:973-980, 1992
94. Stahli et al., Methods in Enzymology 9:242-253 (1983)
95. Kirkland et al., J. Immunol. 137:3614-3619 (1986)
96. Harlow and Lane, "Antibodies, A Laboratory Manual," Cold Spring Harbor Press (1988)
97. Morel et al., Mol. Immunol. 25(1):7-15 (1988)
98. Cheung et al., Virology 176:546-552 (1990)
99. Moldenhauer et al., Scand. J. Immunol. 32:77-82 (1990)
100. Beauregard et al., Cell. Microbiol. 2: 251-58, 2000
101. Kim et al., Protein Expr Purif. 30(2):293-300, 2003
102. Wadstroem and Smyth, Sci. Tools 20: 17-21, 1973
103. Coolican et al., J. Biol. Chem. 261: 4170-6, 1986
104. Lonergan et al., J Food Sci. 60:72-3, 78, 1995
105. Twining, Anal. Biochem. 143: 30-4, 1984
106. Buroker-Kilgore et al., Anal. Biochem. 208: 387-92, 1993
107. Ng et al., Anal. Biochem, 183: 50-6, 1989

The invention claimed is:

1. A diagnostic kit for hepatitis C virus infection comprising
   (i) a polynucleotide consisting of the nucleic acid sequence set forth in SEQ ID NO:2, or
   (ii) an oligonucleotide consisting of the nucleic acid sequence set forth in SEQ ID NO:3, or
   (iii) both of the nucleic acid molecules of (i) and (ii),
   to diagnose patients exhibiting hepatitis C virus infection symptoms or at risk for developing hepatitis C virus infection symptoms.

2. The kit according to claim 1 comprising both a polynucleotide consisting of the nucleic acid sequence set forth in SEQ ID NO:2 and an oligonucleotide consisting of the nucleic acid sequence set forth in SEQ ID NO:3.

* * * * *